(12) United States Patent
Bellin et al.

(10) Patent No.: US 7,917,376 B2
(45) Date of Patent: *Mar. 29, 2011

(54) SYSTEM AND METHOD FOR MONITORING PATIENT CARE

(75) Inventors: Eran Bellin, Teaneck, NJ (US); David Fletcher, New York, NY (US); Noah Geberer, Asloria, NY (US)

(73) Assignee: Montefiore Medical Center, Bronx, NY (US)

( * ) Notice: Subject to any disclaimer, the term of this patent is extended or adjusted under 35 U.S.C. 154(b) by 432 days.

This patent is subject to a terminal disclaimer.

(21) Appl. No.: 12/209,434

(22) Filed: Sep. 12, 2008

(65) Prior Publication Data

US 2009/0076845 A1 Mar. 19, 2009

Related U.S. Application Data

(63) Continuation-in-part of application No. 11/023,994, filed on Dec. 28, 2004, now Pat. No. 7,737,477.

(60) Provisional application No. 60/533,030, filed on Dec. 29, 2003, provisional application No. 60/535,041, filed on Jan. 8, 2004.

(51) Int. Cl.
G06Q 10/00 (2006.01)
G06Q 50/00 (2006.01)

(52) U.S. Cl. .......................................................... 705/2

(58) Field of Classification Search .................. 705/2, 3, 705/4; 707/104.1
See application file for complete search history.

(56) References Cited

U.S. PATENT DOCUMENTS

| | | |
|---|---|---|
| 5,324,077 A | 6/1994 | Kessler |
| 5,508,912 A | 4/1996 | Schneiderman |
| 5,732,709 A | 3/1998 | Tacklind |
| 6,277,072 B1 | 8/2001 | Bardy |
| 6,280,380 B1 | 8/2001 | Bardy |
| 6,551,243 B2 | 4/2003 | Bocionek |
| 6,887,201 B2 | 5/2005 | Bardy |
| 6,956,572 B2 | 10/2005 | Zaleski |
| 2001/0020229 A1 | 9/2001 | Lash |
| 2001/0032099 A1 | 10/2001 | Joao |
| 2002/0038378 A1 | 3/2002 | Simmon |
| 2003/0028082 A1 | 2/2003 | Thompson |
| 2003/0050794 A1 | 3/2003 | Keck |
| 2003/0216938 A1 | 11/2003 | Shour |
| 2007/0050187 A1 | 3/2007 | Cox |

*Primary Examiner* — Gerald J. O'Connor
*Assistant Examiner* — John A Pauls
(74) *Attorney, Agent, or Firm* — Wiggin and Dana LLP

(57) ABSTRACT

Systems and methods are provided for facilitating management of health care in medical facilities such as hospitals, clinics, emergency rooms, etc., for example by monitoring and assessing the quality of patient care. Data is collected and operated on relating to medical conditions, treatment, cost, care, events, outcomes and results of treatments, and data representing the collective experience of similar patients is mined to discover opportunities to improve the quality of health care. Statistical and comparative data and reports including such and other information indicate a quality of care and provide epidemiologically cogent information. Quality of care may be considered as achieving desired or expected norms of performance, including success, in a timely fashion, and can be judged not just by what functionally happens during a patient instigated encounter, but also by long term outcomes evidenced by the patient's passage through the health care delivery system.

20 Claims, 86 Drawing Sheets

Length Of Stay
Results

Overview:
What is the distribution in length of stay for discharges with specified diagnoses and other restrictions?

Method:

This analytic considers inpatient discharges with the specified diagnoses and other analytic restrictions listed under "Criteria". If the study is based on a stored cohort, only patients from that cohort are included and only if they meet other study criteria. Some cohorts have dates associated with the patient MRN's. If the "utilize cohort dates" option is also selected, the enrolling inpatient admission occurs after the patient's cohort date.

The distribution of LOS is presented as both a percentile and a cumulative percent curve. Two group comparisons also have a p-value (log-rank Mantel-Haenszel) to test for difference in each group's curve.

Mortality Results

Criteria | Method | Demographics | Outcomes

Criteria:
Header
Name: chf05v00mort
Last Changed: 11/21/2008 9:09:13 AM
User: Geberer, Noah

Date Range And Risk
Interval to study: From admission to death | From admission to death
Source of death data: SSA matches: SSN only | SSA matches: SSN only
Inpatient Date Range: 1/1/05 | 1/1/00
to: 12/31/05 | 12/31/00
Risk Window: 365 | 365
Times to show % of cohort w/outcome: 30,60,270,365 | 30,60,270,365

Discharge Details
*Diagnosis*
Diagnosis: CHF Primary only | CHF Primary only
*Insurance*
Line of Business: MEDICARE | MEDICARE

Demographics
Age: Age >= 65 | Age >= 65

Display
Group Name: yr05 | yr00

Group 1 Sensitivity: yr05
You have chosen to use death as reported by the Social Security Administration using the match criteria of : SSA matches: SSN only.

For this study there were 140 in-hospital deaths documented. To give you a sense of the accuracy of the SSA match, 132 of the 140 documented deaths were also found in the match to SSA data. This gives a sensitivity of 94.3% (89.1,97.5)

Group 2 Sensitivity: yr00
You have chosen to use death as reported by the Social Security Administration using the match criteria of : SSA matches: SSN only.

For this study there were 140 in-hospital deaths documented. To give you a sense of the accuracy of the SSA match, 125 of the 140 documented deaths were also found in the match to SSA data. This gives a sensitivity of 89.3% (82.9,93.9)

Modify Criteria | Print All Tabs | Patient List | Save Criteria...

Criteria:
Header
- Name: aaaaer
- Last Changed: 11/19/2008 9:01:50 AM
- User: Geberer, Noah

Visit Date Range
- Interval to study: Triage to ER Discharge / Triage to ER Discharge
- Time Range: 1/1/04 to 1/10/04 / 1/1/04 to 1/10/04

Visit Details
- *Diagnosis*
- Diagnosis: Asthma Primary or Secondary / Asthma Primary or Secondary
- *Responsible Entity*
- Facility: MMC Moses Division / MMC Albert Einstein Division

Display
- Group Name: moses / einstein

Time To Event Results

Criteria:
Header:
- Name: gatifloxacin glucose 250-1000
- Last Changed: 11/19/2008 9:22:34 AM
- User: Geberer, Noah

Patients/Cohort
- Cohort: USR: gatifloxacin 66 and up outpat [U]
  - ⊞ Details...
- Not in other group: USR: macrolides 66 and up outpat [U]
  - ⊞ Details...
  - Checked

Time / Risk
- Before or After: after
- Blackout period: 2
- Risk Window: 30

Outcome Event
*Labs*
- Lab Set/Test 1: GLUCOSE
- Value Low (Lab/Set 1): 250
- Value High (Lab/Set 1): 1000

Display
- Choose units for time: Days
- Group Label: gatifloxacin — macrolide control
- Times to show % of cohort with outcome: 3,5,10,15,20,25,30

Cohort: Cohort Name — 6600

Earliest of Group 1: DX DATE

(

All of EV1: Clinic Visit with — 6601
[ ICD9 = "DiabMel no c" ]
WHEN IN Duration1: QDR with [ Date > 12/31/1996 ]

OR

All of EV2: Lab with — 6602
[ Lab Test = "HBA1C" AND Lab Value > 7 ]
WHEN IN Duration1: QDR with [ Date > 12/31/1996 ]

OR

All of EV3: Problem List with — 6603
[ Problem Type = Diabetes AND End Point = "Start Date" ]
WHEN IN Duration1: QDR with [ Date > 12/31/1996 ]

6604
)

AND

All of EV4: Lab with
[ Lab Set = LDL CHOLESTEROL AND Lab Value > 130 ]
WITHIN 0 TO 30 days after Group 1: DX DATE
6608
6605

AND

NONE of EV5: Finding with
[ Finding Set = EYE EXAMS ]
WHEN IN Duration 2: QDR with [ Date BETWEEN 4/1/06 AND 4/1/07 ]
6606  6607
6609

```
┌─────────────────────────────────────────────────────────────────┐
│ ▐Edit Selected▌  ☐ Save As  [⊡][⇨×][×]                          │
│   Name: │morbidly obese admits│                             +   │
│                                                                 │
│ ▐Event Canvas▌                          ╭─7902                  │
│ ⊟─[ C ][B] morbidly obese admits: [ Earliest of Any (And) ]     │
│      ▦♟ admits 07: [ All of [admission : InpatientAdmissionDate] WHEN IN [2007] ] │
└─────────────────────────────────────────────────────────────────┘
  └7901
```

FIG. 79A

```
┌─────────────────────────────────────────────────────────────────┐
│ ☐NOT │Findings Type ▾│ = ▾│       │BODY MASS INDEX          ▾│ │
│ ▐ Update ▌ ▐ Update and Close ▌ ▐ Close ▌                       │
└─────────────────────────────────────────────────────────────────┘
```

FIG. 79B

```
┌─────────────────────────────────────────────────────────────────┐
│ ☐NOT │Findings Value ▾│ > ▾│       │35                         │ │
│ ▐ Update ▌ ▐ Update and Close ▌ ▐ Close ▌                       │
└─────────────────────────────────────────────────────────────────┘
```

FIG. 79C

SYSTEM AND METHOD FOR MONITORING PATIENT CARE

CROSS-REFERENCE TO RELATED APPLICATIONS

This application is a continuation-in-part of U.S. application Ser. No. 11/023,994, filed Dec. 28, 2004, now U.S. Pat. No. 7,737,477, which claims the benefit of U.S. provisional Application No. 60/533,030 filed Dec. 29, 2003, and U.S. provisional Application No. 60/535,041 filed Jan. 8, 2004, both of which provisional applications are incorporated herein by reference.

BACKGROUND OF THE DISCLOSURE

The present invention relates to facilitating management of patient care, including monitoring and assessing the quality of patient care, and provides data, reports, analytics, etc. related thereto.

SUMMARY OF THE DISCLOSURE

The invention provides embodiments of systems and methods which facilitate management of health care provided by a facility, e.g., a hospital, clinic or emergency room. Embodiments of the invention provide for monitoring or accessing (meant in a broad sense, e.g., including analyzing) patient care and the quality of patient care, and for providing information related thereto. Embodiments of the invention may also include collecting data relating to treatment, outcomes, cost, quality of care, results of treatments, among other things. Embodiments of the invention provide, among other things, software that may be considered to express the philosophic notion that an Information Technology aware health care delivery system can help provide safe and effective health care for all its patients, and that the collective experience of similar patients may be mined continuously to discover opportunities to improve efficiency, safety, and effectiveness of health care.

Embodiments of the invention can assist individual practitioners in delivering quality care that satisfies patient needs and expectations. Quality, as a notion, may be considered as achieving desired or expected norms of performance, including success, in a timely fashion. Quality care can be judged not just by what functionally happens during a patient instigated encounter, but also by long term outcomes evidenced by the patient's passage through the health care delivery system. Outcome, as used herein includes any outcome associated with a medical condition, such as full recovery, death, an event, laboratory test value, or other result of a medical condition. Event, as used herein includes events such as encounters, e.g., a hospital admission or discharge, emergency room visit or triage, clinic visit, laboratory test result, mortality or other outcome or event.

According to an embodiment of the invention, a system is provided for facilitating management of health care provided by a facility. This may be accomplished using data stored in a database including patient event related data and data related to health related care provided by the facility. The system comprises computer readable memory that stores a database, e.g., the database referred to above, including data described herein, e.g., relating to patients treated by the facility, data relating to events occurring with respect to patients treated by the facility and data related to health related care provided by the facility to patients. The system also includes at least one computer which receives data entered by an input device, e.g., a keyboard and/or a pointing device such as a mouse, via a user interface displayed on a display device. The user interface receives data identifying at least one event, data identifying at least one calendar time period and data identifying a cohort including a plurality of patients and the at least one computer accesses the memory in response to received data entered by the input device and provides statistical data that is presented on the display device usable for managing health care provided by the facility. The statistical data provided by the at least one computer is related to at least one elapsed time period ending with an occurrence of the at least one event for each of the patients in the cohort and providing an indication of the quality of the health related care provided by the facility which is usable by the facility to manage health care provided by the facility.

In an embodiment, the system described above may be provided to operate over a network. In this embodiment, at least one network computer and at least one other computer are provided. The at least one network computer is capable of accessing the memory and providing the statistical data. The at least one other computer provides information to the at least one network computer and receives statistical data from the at least one network computer via the network. The user interface is provided at the at least one computer for receiving the data entered by the input device, the display device is provided at the at least one computer and the at least one network computer provides the statistical data via the network to the at least one computer.

According to an embodiment of the invention, a computerized method is provided for facilitating management of health care provided by a facility. The method comprises receiving in at least one computer the data referred to above identifying at least one event, data identifying at least one calendar time period and data identifying a cohort including a plurality of patients, and the at least one computer accesses a database, e.g., the database described above, and provides the statistical data referred to above.

According to another embodiment, a computerized method for monitoring patient care is provided which comprises receiving data relating to a medical condition of a plurality of patients, associating the received data with data relating to care of each of the plurality of patients and data relating to an outcome for each of the plurality of patients, and providing at least one indication of quality of care for the medical condition based on the data relating to the medical condition, the data relating to the care, and the data relating to the outcome for each of the plurality of patients. In this embodiment, the data relating to the medical condition, the data relating to the care and the data relating to the outcome in association with personal information of each of the plurality of patients is stored in the database. Personal information may comprise demographics information. Preferably access is restricted to the personal information of each of the plurality of patients associated with the data relating to the medical condition, the data relating to the care and the data relating to the outcome.

According to another embodiment, a computerized method is provided for providing an indication of the quality of patient care which comprises receiving data relating to a first medical condition for a first patient, querying a database, e.g., the database described above, that includes data relating to at least the first medical condition for a plurality of patients, data relating to care provided to each of the plurality of patients and data relating to an outcome for each of the plurality of patients. Based on the database query, the data relating to the first medical condition, the data relating to care provided to each of the plurality of patients, and the data relating to the outcome for each of the plurality of patients are correlated, e.g., provided on a comparative basis, which provides at least one indication of quality of care.

According to another embodiment, a computerized method is provided for providing an indication of the quality of patient care, which comprises receiving data relating to a first patient, correlating, e.g., on a comparative basis, the received data to data relating to at least one medical condition, data relating to care relating to the at least one medical condition, and data relating to an associated outcome of the at least one medical condition for each of a plurality of patients, which provides an indication of a quality of care provided to the first patient.

Correlated or comparative data may indicate a deviation of care, and embodiments that provide such correlated or comparative data, may also provide a deviation of care based on such data.

As described herein, examples of the at least one event and a related at least one elapsed time period include: admission of patients in the cohort to and discharge of the patients in the cohort from the facility and the at least one elapsed time period comprises length of stay in the facility of the patients in the cohort; discharge of patients in the cohort from and readmissions of the patients in the cohort to the facility and the at least one elapsed time period comprises length of time to readmission to the facility of the patients in the cohort; admission of patients in the cohort to the facility and death of patients in the cohort, and the at least one elapsed time period comprises length of time from admission to death of the patients in the cohort; discharge of patients in the cohort from the facility and death of patients in the cohort, and the at least one elapsed time period comprises length of time from discharge to death of the patients in the cohort; one or more laboratory tests performed with respect to patients in the cohort that reach a target outcome, and the at least one elapsed time period comprises a length of time from a start time to reaching the target outcome; one or more laboratory tests performed with respect to patients in the cohort that maintain a target outcome, and the at least one elapsed time period comprises a length of time from a start time that the target outcome is maintained.

Facility is used herein in a broad sense and encompasses a medical center, hospital, clinic, emergency room, etc. The entered data may include data identifying a medical condition and patient demographic data, and the statistical data may include patient demographic data.

In an embodiment, patient care is monitored or assessed by monitoring patient outcomes, e.g., by tracking patient health from the beginning of treatment, e.g. from triage, through a treatment period and beyond, for example, after a patient is discharged from a treatment facility. In one embodiment, the invention can correlate treatment, resulting outcomes, e.g., long-term effect or other outcome, or other epidemiology data, and provide, preferably on a real time basis, data, analytics, reports (in various forms and formats, e.g., text, charts, lists, graphs, etc.), etc. which assess the efficiency and quality of care provided. Healthcare practitioners can query the database and obtain data and/or analytics, e.g., in reports, related to quality of care. In one embodiment of the invention, data, analytics, reports, e.g., real time reports and/or fixed reporting period reports such as monthly, quarterly, etc., may provide indications of quality of care. Care as used herein is used to describe patient care, such as treatment, including for example, medication, surgical procedures, laboratory tests, hospital or clinic visits.

In an embodiment, data relating, e.g., to conditions, medical treatment, events, encounters and/or outcomes is stored in a database in one or more associations and preferably in association also with patient data, e.g., patient identification and demographics. Such data may include, for example, statistics related to clinical data, administrative data, financial data, medical provider, condition, outcomes, encounters, process of care data (anything involved in the process of tracking or providing care along the total health care continuum, which includes care provided in hospital, ambulatory, home health, or nursing home) and results or other data related to patient care. Patient care data is preferably stored in association with data identifying the patient, e.g., social security number, medical record number or demographic information. Data stored in the database may be used in, e.g., statistical models and analytics, which provide epidemiologically cogent display technology and output graphs and analytics indicating quality of care, e.g., quality of the outcome of care efforts as well as the quality of the process of care itself.

Target outcomes may be identified, for example, desired or normal outcomes, and associated with medical conditions. For example, a desired range of cholesterol levels for LDL (low-density lipoprotein), or blood sugar levels measured by hemoglobin A1c (HbA1c) for diabetics may be identified. The target outcomes may be associated with a medical condition, e.g. congestive heart failure (CHF) or other condition. The outcome data and condition data is preferably stored in association in a database. In one embodiment, the target outcomes are identified and associated with analytics, further described herein.

In an embodiment, a system user inputs, e.g., via a user interface such as a browser, e.g., a standard web browser such as Microsoft Internet Explorer, or a thin client interface, or other user interface, values or parameters to focus the analysis in an area of interest. An embodiment of the inventive system queries data records in a database, preferably in real time, to obtain the records and other data associated with patients falling within the user specified values or parameters, which are provided to the user, e.g., in a selectable or pre-set data representation format. In an embodiment of the invention, reports in the form of summaries are provided including clinical, administrative and financial data. In embodiments of the invention: patient care process and outcome information is provided, e.g., outcome failures, or a list of patients who failed to achieve target outcomes or intermediate endpoints; monitoring strategies are provided to indicate when a patient is deviating from a process of care performance from norms or desired targets; reports are provided related to the analytic results; patient groups and/or individuals who deviate from desired targets are identified for further study; health care is identified for which intervention will have the greatest success in achieving a specified target outcome; information is provided to authorized users only, in accordance with HIPAA requirements.

In an embodiment, a system incorporating the invention comprises a database capable of storing data of the type disclosed herein which can be accessed by one or more computers and/or electronic devices via a network, e.g., a LAN, WAN, intranet or the Internet. A server or host or other computer or computers may be provided to manage and/or control the database, and/or run analytics and/or algorithms with respect to data stored in the database and/or provide data to a computer or electronic device which accesses the network, e.g., on pull and push bases. Some analytics provided by embodiments of the invention include: Length of Stay (LOS), Readmission, Mortality, Laboratory Outcomes, Quality Duration Calculator, Emergency Room (ER) Patient Flow Time and Time to Event. Some of these analytics are also referred to herein, or include, events as that term is used herein.

According to another embodiment, a computerized method for facilitating management of patient care comprises defining a set of events relating to a query, where each event in the set is applicable to a plurality of patient records; composing a logical expression including the events; specifying at least one calendar time period relating to at least one event, evaluating the logical expression for each of the patient records; identifying a set of patient records consistent with the logical expression; labeling that set of patient records as a cohort or an event collection; performing the query on patient data for the cohort or event collection to yield a query result; and generating a report including the result of the query. The event definition is performed via a first portion of a user interface affording a user access to data for defining the events; the calendar time period is specified via a second portion of the user interface; and the label of the cohort or event collection is displayed on a third portion of the user interface, affording the user access to a definition of the cohort or event collection. An event collection includes all patient records consistent with the logical expression, while a cohort includes, for a given patient, only one patient record consistent with the logical expression. The calendar time period is a limiting condition on the logical expression.

According to another embodiment, a user interface for organizing a query related to patient care includes a first portion for defining a set of events relating to the query and applicable to a plurality of patient records, and for composing a logical expression including the events; a second portion for specifying at least one calendar time period relating to an event; and a third portion for listing a label of at least one set of patient records, the label indicating that the set is either a cohort or an event collection.

According to another embodiment, a system for evaluating patient care comprises a user input device and display; a database of patient data; and a server. The server is configured to provide a user interface accessible by the user at the user input device. The user interface has a first portion for defining a set of events relating to a query and applicable to a plurality of patient records, and for composing a logical expression including the events; a second portion for specifying at least one calendar time period relating to an event; and a third portion for listing a label of at least one set of patient records, the label indicating that the set is either a cohort or an event collection. The server is also configured to access the database of patient data, perform the query on the patient data for the cohort or event collection to yield a query result, and generate a report including the result of the query, in accordance with a request from the user.

Length of Stay

Length of Stay provides the measure of hospital care efficiency, e.g., how rapidly patients with the same diagnosis are cared for and brought to a state of readiness for discharge from the hospital. Length of Stay can be used as a measure of efficiency in processing patients. The analytic can be used to provide a list of patients with specific diagnoses for chart review of process of care quality, ultimate outcomes, and satisfaction follow up studies. Disposition studies, e.g., death, nursing home, rehabilitation or other outcome, can be performed comparing those patients in one category with the others to see if a particular intervention might have been appropriate. Studies of timeliness of service, e.g., inpatient care or coordination of discharge service needs can be performed in charts identified by the analytic. Examples of comparisons can be: age, gender, clinics, years, managed care status, diagnose, primary payer, hospital, or other parameter. In one aspect, the quality of care can be assessed by whether a particular length of stay, such as a short length of stay, causes a readmission to the hospital.

Readmission

Readmission provides the measure to evaluate quality of care by determining the likelihood and speed of rehospitalization. The analytic provides a measure of success in treating patients effectively. Longer intervals to readmission indicate greater success in patient care or treatment. The analytic can be used to provide a list of patients with specific readmission times and diagnoses for review of process of care quality, ultimate outcomes, and satisfaction follow up studies. The studies could include assessment of in hospital planning for discharge, appropriate medications at discharge, and follow up in the community. Data sources for the analytic can include hospital chart data, front end review of hospitalization, last medications given in hospital, clinic charts, social service notes, or other data. Hospital residents or other inpatients can be involved in the process of assessing the quality of services provided.

Mortality

Mortality indicates the time to death from hospital admission or live discharge for a user-selected cohort. A cohort, as used herein, refers to a group, such as a statistical group of patients, or patients having certain characteristics. One embodiment of the invention provides a cohort builder, e.g., to establish parameters to select certain patients on which to run an analytic, e.g., to assess particular outcomes. The information provided by the analytic can provide an indication of a correlation of care or treatment and an outcome such as death.

Laboratory Outcome

Laboratory Outcomes indicates a quality measure allowing the user to define laboratory and time parameters for success, evaluate proportionate success, and create a work list to support targeted remediation so that patients identified as failures can be followed up with by a clinic. An example of an application of the Laboratory Outcome analytic is a clinic using failure rates and indications of patients who failed to follow up as prospective targets for specific interventions to bring outcome measures under control in the future. In addition, the analytic provides a list of patients with specific diagnoses for a review of process of care quality, ultimate outcomes and satisfaction follow up studies.

Quality Duration

Good clinical care results in a patient achieving and maintaining certain laboratory test values for a period of time after an event. To assess a facility's quality of care or quality of outcome achieved, patients are identified with a therapeutic need and the time to reach the target laboratory test values is obtained. The time period over which a patient maintains the target laboratory test value is also obtained. Quality Duration Calculator evaluates the time period for a patient to achieve and maintain a particular condition, e.g., lab value or other health indicator.

Emergency Room Patient Flow

Emergency Room Patient Flow is a summary measure of interval time from which can be used to derive efficiency comparisons between hospitals or time periods, or both. The intervals can be used as a measure of efficiency in processing patients. The Emergency Room Patient Flow analytic can be used to identify patients received in an emergency room with a specific diagnosis for a review of process of care quality, outcomes, satisfaction follow up studies and other indications of quality of care. In addition, the analytic provides tracking of timeliness of consultants, procedures and completion of required tasks.

Time to Event

Time to Event indicates the summary of time to events, e.g., encounters, certain result, mortality or other event. For example, the analytic provides information relating to the incidence for achieving an outcome, e.g., an encounter such as a hospital admission, hospital discharge, emergency room visit, clinic visit, a laboratory test result, mortality or other outcome, over time, the incidence density of events with relative risk and risk difference comparisons between groups or a cohort, or other event related information.

Among other inventions, the system and method described herein provides the ability to obtain data and analyses of facility care in a clinically and epidemiologically cogent manner, preferably by interrogating a user through the use of drop down menus and requiring a user to answer questions necessary to create an epidemiologically cogent cohort of patients for study. Software implementing the method described herein offers a metric of a clinical outcome be it efficiency, effectiveness, efficacy, quality, or safety taking into considerations the vagaries of clinical practice. For example, the software creators know that often unnecessary lab tests are drawn too early to be meaningful in assessment of the desired clinical endpoint and therefore must be filtered from consideration in the evaluation of any relevant outcome. For example, the blackout period in the laboratory analytic or the mortality censorship hidden in the readmission or laboratory analytic. When a cohort is evaluated for success or failure, the result can be provided to the responsible clinic/MD/dept for appropriate action. One purpose of the analysis is to identify the locus of control of the care so that appropriate interventions can be taken. The analysis provides a user the ability to drill down within the cohort and identify an individual patient who is failing to achieve targeted goals to permit the health care delivery system to target those patients for specific efforts at remediation. The system and method is preferably fully self documenting for its methods, criteria, and output, and is available both online and in a pdf output. The system and method provides intermediate data summaries that make the analyses tractable for the end user to evaluate on a case by case basis, e.g., in real time. Examples include the ED return analytic that allows the user to find all the patients who returned to the ED within a certain time period and then displays in reverse sort order the clinical history (ICD-9 codes, ED visits, hospitalizations, mortality) of each patient who came back in within a certain time period. This tool allows the physician reviewer to rapidly review cases eliminating those with no quality problem and identifying those that might have a quality problem. In addition, the invention provides financial metrics which attach dollars (revenue) to the cohort to establish relative costs of different management strategies. Where cost is not merely episodic but includes the longitudinal experience over time. Pharmaceutical metrics are also provide which establish persistence of medication use relating to intermediate process measures of success and ultimate outcome measures—readmission, ED visits, costs, mortality.

In an embodiment, a user friendly interface provides a formal query in a computer language (e.g., SQL) to extract the records and variables of patients in response to data input by a user. For example, data may be input to templates or charts provided by a user interface such as a browser. Programming converts the data to a form, e.g., an SQL query, that may be transferred to a server or host, e.g., a statistical server. Statistical servers are commercially available, and programming and algorithms implementing functionality disclosed herein in a statistical server may provide, e.g., analytics, data, reports disclosed herein. In one embodiment, such analytics may be viewed as tools that evaluate the quality of medical care by allowing a user to identify the criteria used to qualify the patients as belonging to a specific. cohort, then applying a metric of quality to that cohort, and evaluating the quality of performance of the health care system by the metric applied to identified subgroups. Specific analytics contain specific patentable notions of how to present meaningfully those descriptions of care to managers, physicians, and supervisors.

In embodiments of the invention: collections are provided of summaries of clinical/administrative/financial data; meaningful patient care processes and patient outcome failures are identified and displayed; a useful work list is generated of patients who failed to achieve target outcomes or intermediate endpoints in process for direct and timely remediation; processes of care summaries and monitoring strategies are created which may be used in mass production facilities for inanimate objects to warn of early deviation of process of care performance from norms or desired targets; self documenting reports—with research grade methods and criteria summarized in each output—are provided; performance summaries may be provided not only on a global basis but also on the basis of specifically identified patients within a cohort whose behavior either as a deviant or control merits further study by interview or chart review, which, e.g., enables targeting of the specific members of the cohort who bear further analysis; the most reasonable target of health service delivery intervention is identified whether it be the individual physician, patient, director of service, or pod of physicians, which provides outcome aggregation strategy that may philosophically define the site at which administrative and clinical efforts would be most meaningful and potentially successful; and analytics which create summaries that look forward and backward in time, and create meaningful control groups.

Embodiments of the invention may provide: graphs/tables that can be cut and pasted into other applications such as PowerPoint to allow for efficient development of teaching and supervisory materials; spreadsheets (such as Excel) that allow a user to do subsequent analysis on the cohorts identified and analyzed in the analytic; fully formatted reports (such as in Adobe Acrobat pdf format) that allow a user to run the analytic and then carry the analysis with them; HIPAA security enablement, e.g., control of line listing access at the user level.

BRIEF DESCRIPTION OF THE DRAWINGS

The invention is illustrated in the figures of the accompanying drawings which are meant to be exemplary and not limiting, in which like references are intended to refer to like or corresponding parts, and in which:

FIG. 5 depicts a screenshot of a parameter entry screen according to an embodiment of the invention;

FIG. 6 depicts a screenshot of a parameter entry screen according to an embodiment of the invention;

FIGS. 7-11 depict screenshots of ICD-9 Set Definition screens according to an embodiment of the invention;

FIG. 12 depicts a screenshot of a parameter entry screen according to an embodiment of the invention;

FIGS. 13-18 depict screenshots of results screens according to an embodiment of the invention;

FIG. 19 depicts a screenshot of a parameter entry screen according to an embodiment of the invention;

FIG. 23 depicts a screenshot of a parameter entry screen according to an embodiment of the invention;

FIGS. 26-28 depict screenshots of reports screens according to an embodiment of the invention;

FIGS. 29-34 depict screenshots of results screens according to an embodiment of the invention;

FIG. 35 depicts a screenshot of a parameter entry screen according to an embodiment of the invention;

FIGS. 36-38 depict screenshots of result screens according to an embodiment of the invention;

FIGS. 39-42 depict screenshots of cohort builders screens according to an embodiment of the invention;

FIGS. 43-47 depict screenshots of results screens according to an embodiment of the invention;

FIGS. 48-49 depict screenshots of parameter entry screens according to an embodiment of the invention;

FIGS. 50-52 depicts screenshots of results screens according to an embodiment of the invention;

FIG. 53 depicts a screenshot of details according to an embodiment of the invention;

FIGS. 54-55 depict screenshots of cohort builder screens according to an embodiment of the invention;

FIGS. 56 and 58 depict screenshots of report entry screens according to an embodiment of the invention;

FIGS. 57 and 59 depict screenshots of reports according to an embodiment of the invention;

FIGS. 63A and 63B depict a reports selection screenshot according to an embodiment of the invention.

FIG. 66 illustrates an example of a definition of a cohort, in accordance with an embodiment of the disclosure.

FIGS. 78A-78G illustrate a process for defining a cohort with the Event Canvas, in accordance with an embodiment of the disclosure.

FIGS. 79A-79F illustrate a process for adding further conditions to the cohort definition of FIGS. 78A-78G, in accordance with an embodiment of the disclosure.

DETAILED DESCRIPTION

Figure 1:
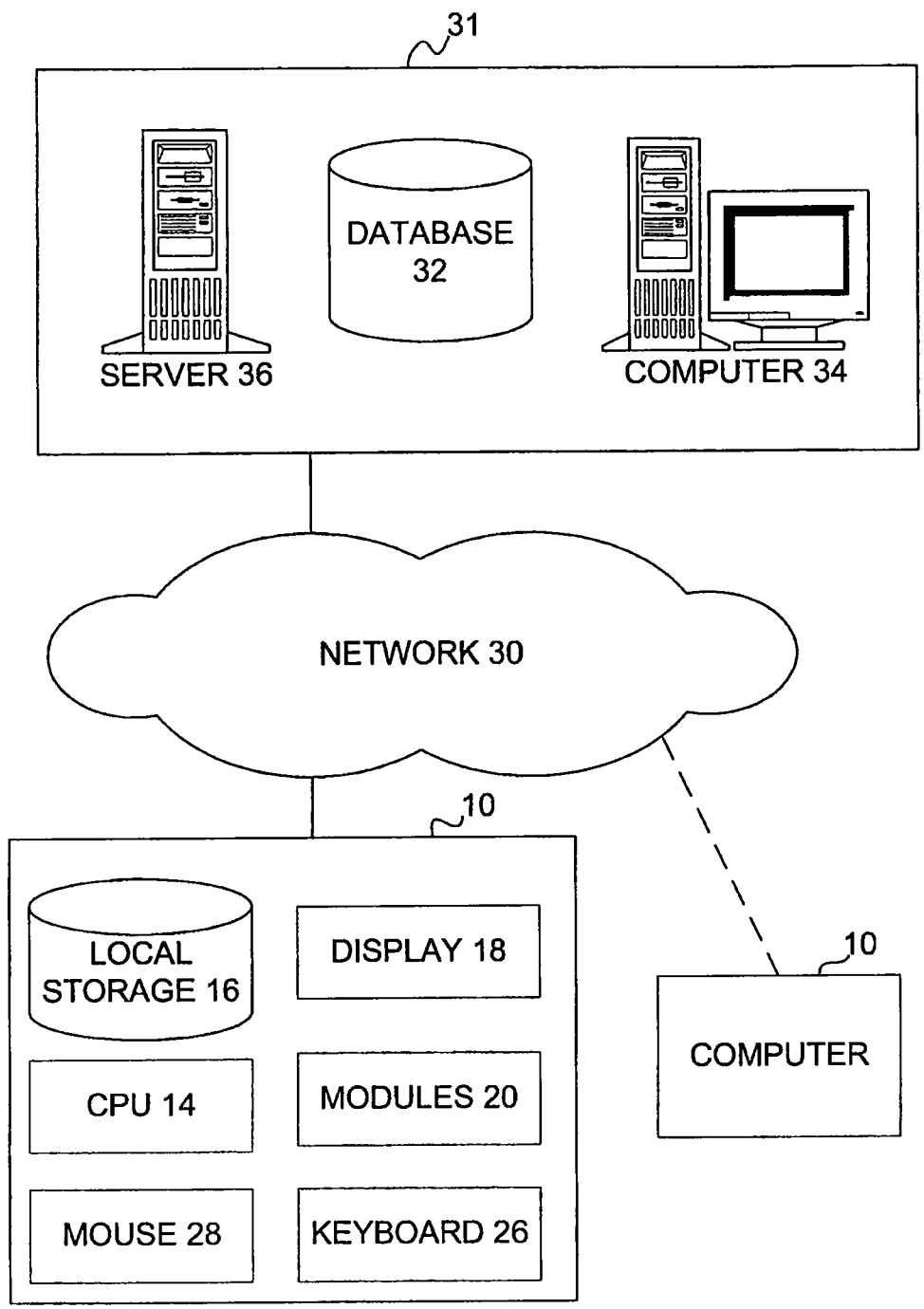
FIG. 1 depicts a block diagram of a system according to an embodiment of the invention.

Preferred embodiments of the invention are now described with reference to the drawings. Referring to FIG. 1 which depicts a system network according to an embodiment of the invention. The system includes one or more computers 10, which generally may include the components shown in FIG. 1, e.g., central processing unit (CPU) 14, local storage 16, display 18, modules 20, input devices, e.g., keyboard 26 and mouse 28. The CPU 14 can be any processor known in the art capable of providing appropriate processor power to run the computer 10. The local storage 16 can be any storage known in the art, capable of storing data locally at the computer 10, such as RAM, internal or external drives. Display 18 can be any screen or monitor from which the screenshots further described herein, can be viewed by a user, such as a computer monitor, LCD screen or other display device. The modules 20 include components used to run the system and methods of the invention, such as software to run the analytics further described herein, or other software or components to provide the functionality described herein. Keyboard 26 and mouse 28 can be any keyboard or mouse known in the art capable of entering information, e.g., parameters or responses, into the computer 10, such as a keypad or writing stylus and screen device. The computer 10 can be also be an electronic device such as a personal digital assistant (PDA), telephone, lap top, or other device capable of inputting data and communicating over a network 30 to database 32 and correspondingly capable of receiving data from the database 32 over network 30.

The network 30 can be any network known in the art, such as a LAN, WAN, intranet or the Internet, or other network. The database 32 can be any database including data storage as further described herein.

The database 32, which may be stored in any suitable computer readable memory, e.g. volatile or non-volatile memory, electronic RAM memory, disc storage, etc., may include data of the type disclosed herein, e.g., statistics related to patients in association with medical care, e.g., clinical data, administrative data, financial data, or process of care data, which includes care provided in hospital, ambulatory, home health, or nursing home, as well as other data. A network computer may configure a computer or processor 34, which can be any data processor known in the art capable of running software to execute analytics, further described herein, using the data in the database 32, and/or a server 36, which can be any device in the network that manages resources of network 30, and preferably processes database queries, further described herein. For example, server 36 preferably is an otherwise conventional statistical server or Statserver that is programmed to carry out functionality disclosed herein. Statservers, e.g., with Splus, are known in the art. Programming to implement functionality disclosed herein in server 36, computer 34 or elsewhere can be constructed by those of skill in the relevant art(s).

For example, a computer system, which may be referred to as, e.g., a network computer, represented generally by reference 31 in FIG. 1, may include computer 34, server 36 and database 32, may be connected by a fiber optic network 30 to computers 10 at health care sites. The computer system 31 may include two NT servers supporting Splus analytics and an NT server supporting a report distribution system (e.g., Cypress). Database 32 storing clinical data may be replicated in a Sybase database, synchronized with a parent or sibling system, e.g., with Golden Gate Software, e.g., residing on a Sun server.

Figure 2:
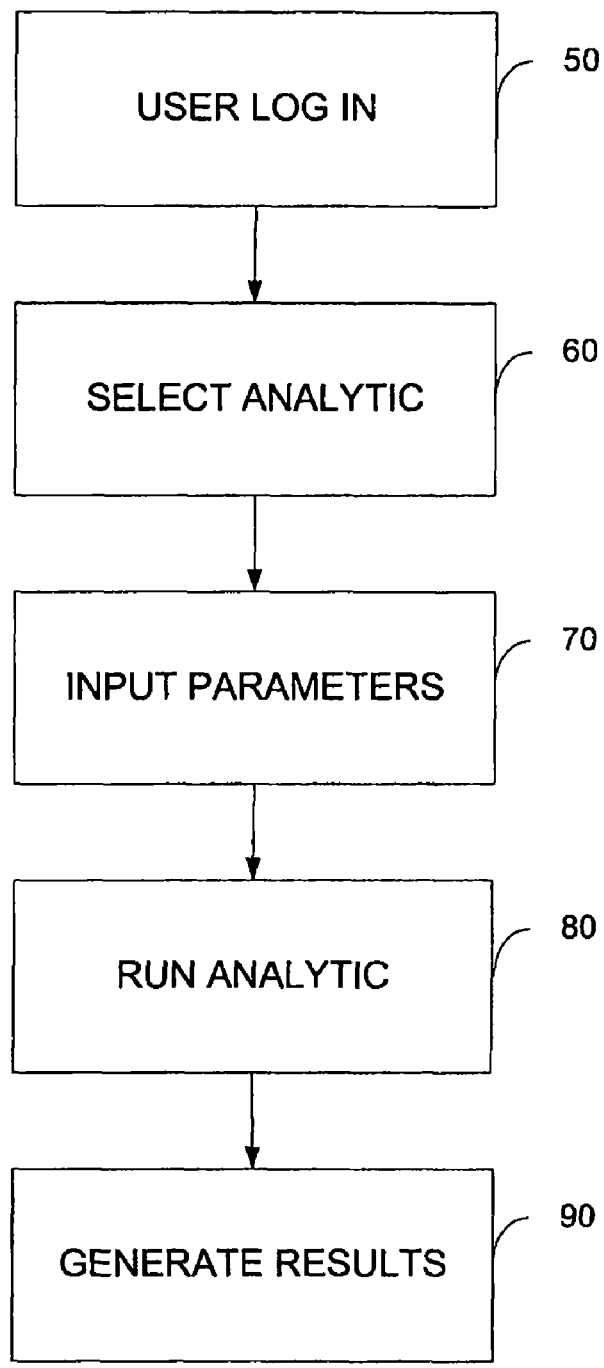
FIG. 2 depicts a flowchart of a method according to an embodiment of the invention.
Figure 3:
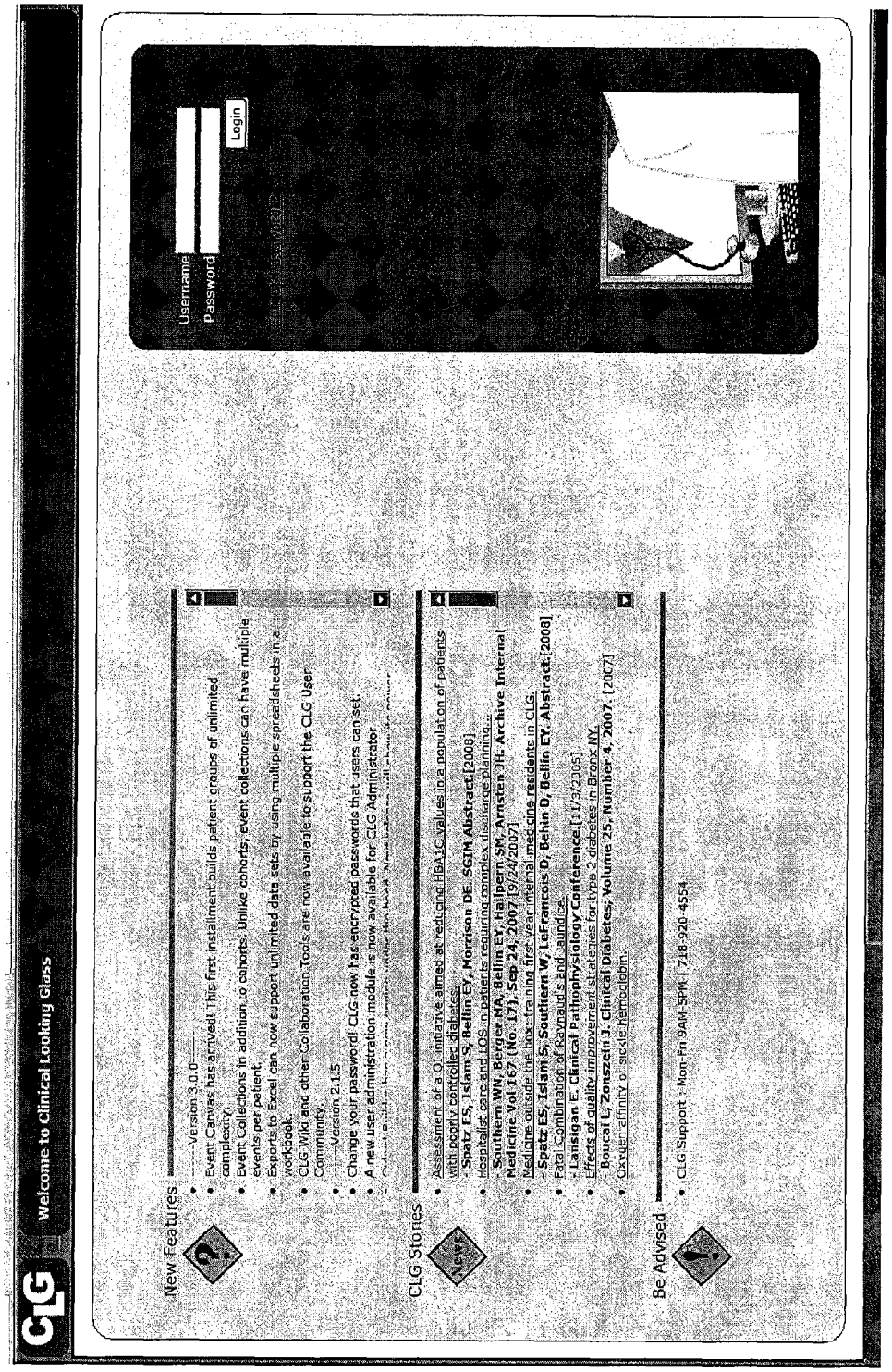
FIG. 3 depicts a screenshot of a login page according to an embodiment of the invention.

Referring to FIG. 2, which depicts a flowchart of a method according to an embodiment of the invention, a user using the invention, logs into the system, step 50, at computer 10, e.g., at a home page. A screenshot depicting the home page log in screen is shown in FIG. 3. In general, a user will log in as an individual, or as part of a group or organization. Referring again to FIG. 2, a user selects an analytic, step 60. The analytic options are selected from a main menu page, which is obtained after a successful log in, e.g., the main menu depicted in the screenshot of FIG. 4. Analytics include options, such as: Lab Outcomes, Mortality, Length of Stay (LOS) Analysis, Readmission, Quality Duration Calculator, Emergency Room (ER) Patient Flow and Time to Event. A user can select an option by clicking on the analytic option and clicking the corresponding run button, or otherwise selecting the options to obtain a parameter entry screen, as depicted in FIG. 5. The user enters values or parameters to the parameter entry screen (FIG. 5), step 70, used to run an analytic, further described herein. When the parameters have been entered, the user selects the run analytic button, or similar button to run the analytic, step 80. The system generates results, step 90, providing data and information related to patients falling within the parameters entered in the analytic. Each analytic option is further described herein. A user may log out at any time while using the system by clicking on the log out button.

In general, the parameter entry screen depicted in FIG. 5, which is for the LOS Analysis, is similar to the parameter entry screens for the other analytic options further described herein, at least to the extent that each provides for parameter input to run an analytic. The types of parameter entry options may vary from analytic to analytic.

Length of Stay (LOS) Analytic

Figure 4:
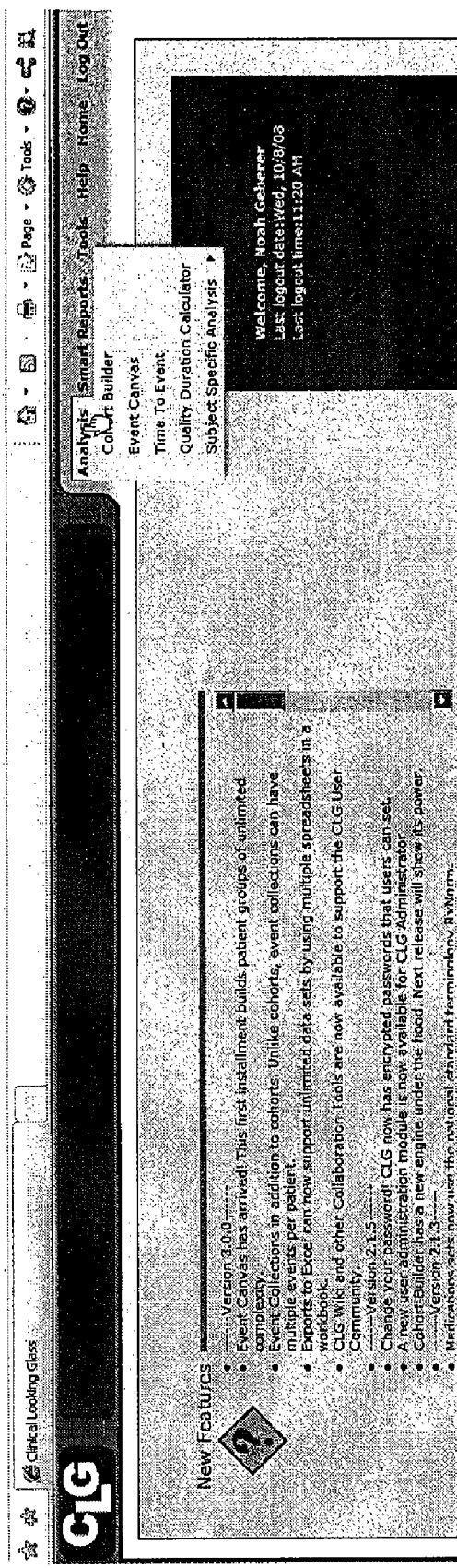
FIG. 4 depicts a screenshot of a main menu according to an embodiment of the invention.
Figure 5:
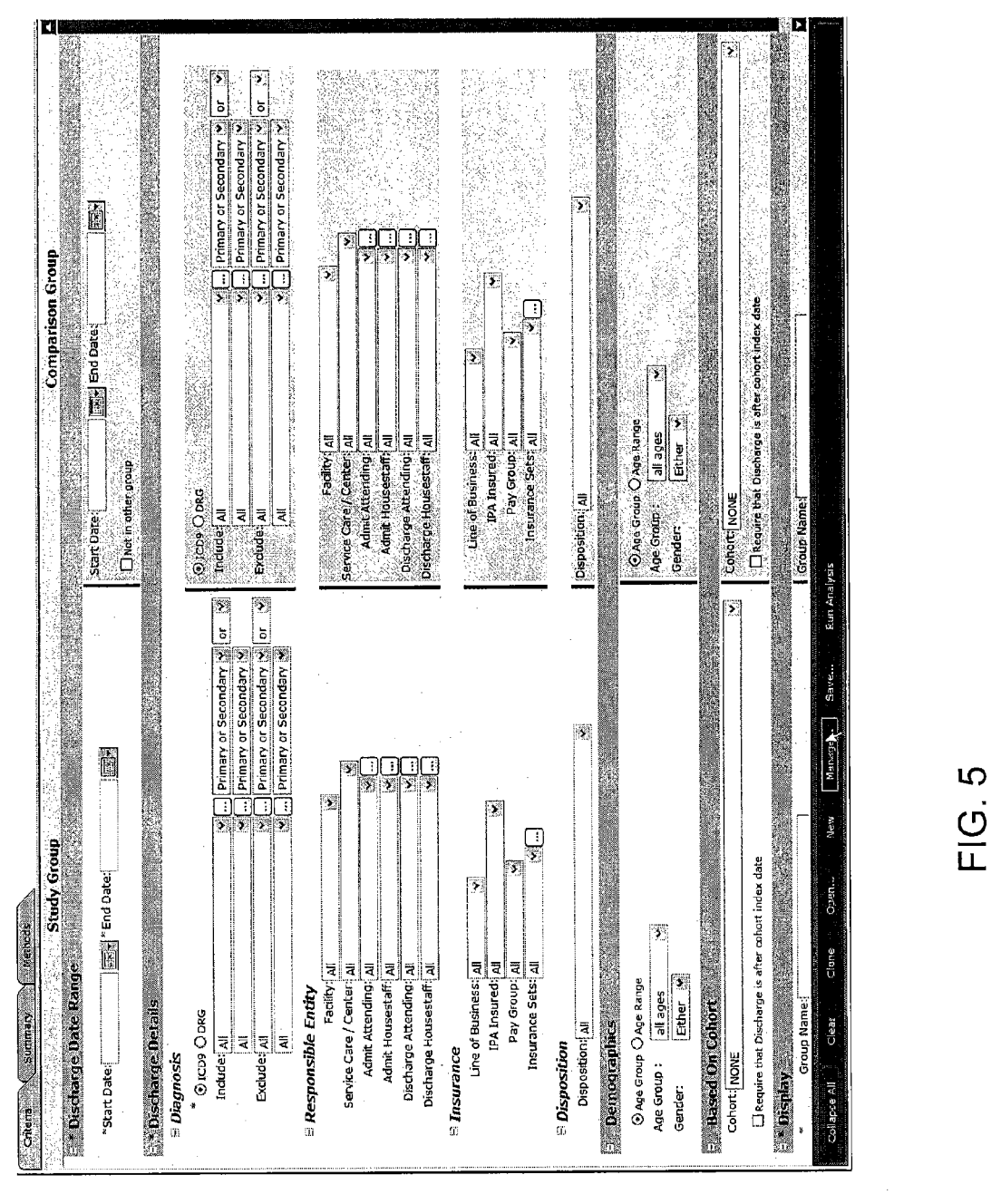

From the main menu screen of FIG. 4, Length of Stay Analysis is selected and the parameter entry screen of FIG. 5 is obtained. Referring to the top row of parameter entry items, parameters may be entered for a study group and/or a comparison group. The comparison group can be, for example, a control group or other known group to provide a result to compare to the study group. A condition is selected using a DRG code or an ICD-9 set. A DRG code is a Diagnosis Related Group code, and an ICD-9 set is a set of codes from the International Classification of Diseases. Both codes are used to identify diseases, diagnoses or conditions, for example, for analysis or billing purposes. In preferred embodiments, the DRG and/or ICD-9 set can be set by standard Federal designation and/or other standard, such as payor source. In the embodiment shown in FIG. 5, the DRG code is selected using a drop down menu. The ICD-9 set is selected, for example by using subsets, such as an AHRQ (Agency for Healthcare Research and Quality) set composed of an aggregation of ICD-9 codes, using a drop down menu to select a single ICD-9 code, or using a drop down menu to build a set of ICD-9 codes.

Figure 6:
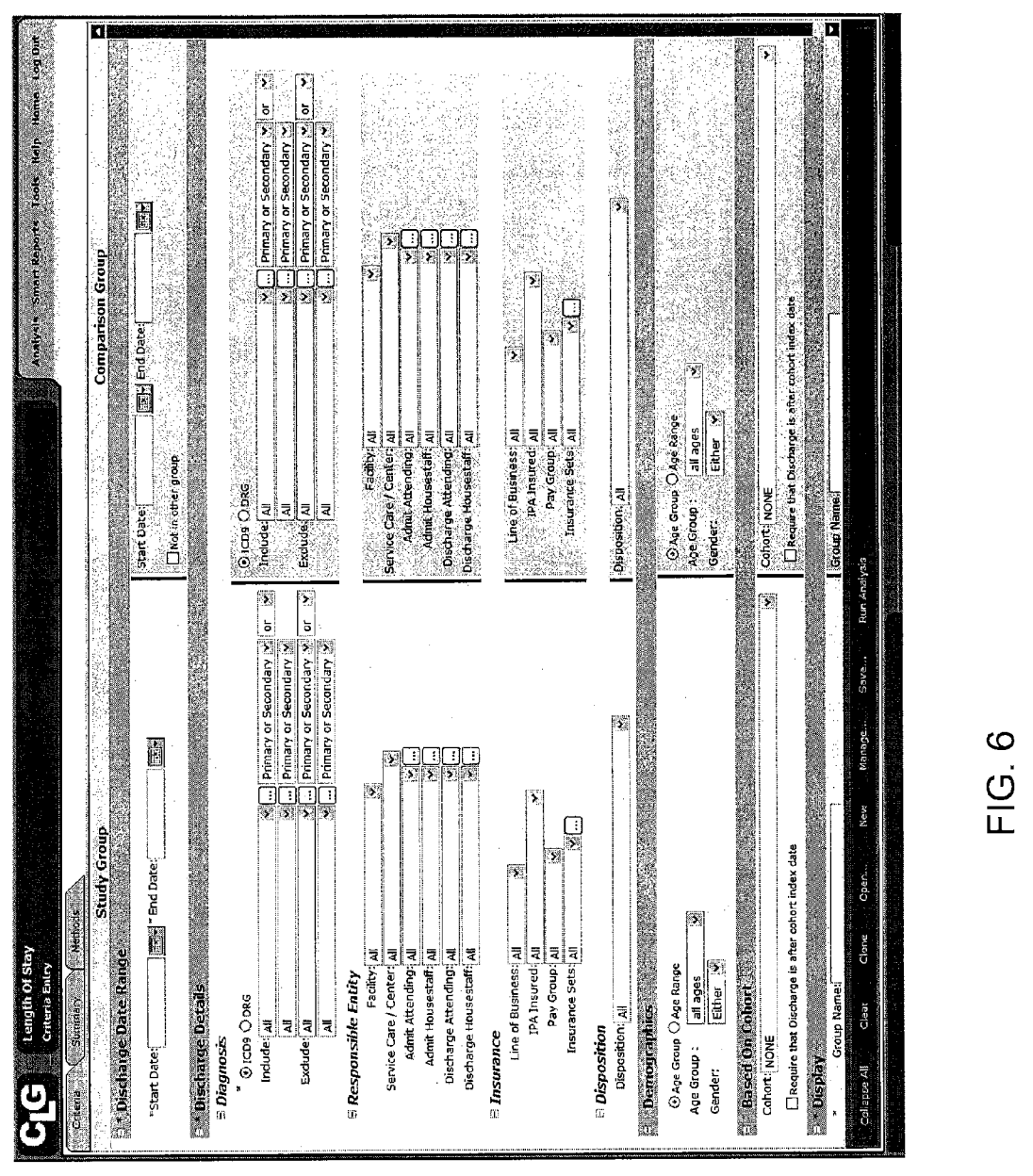
Figure 7:
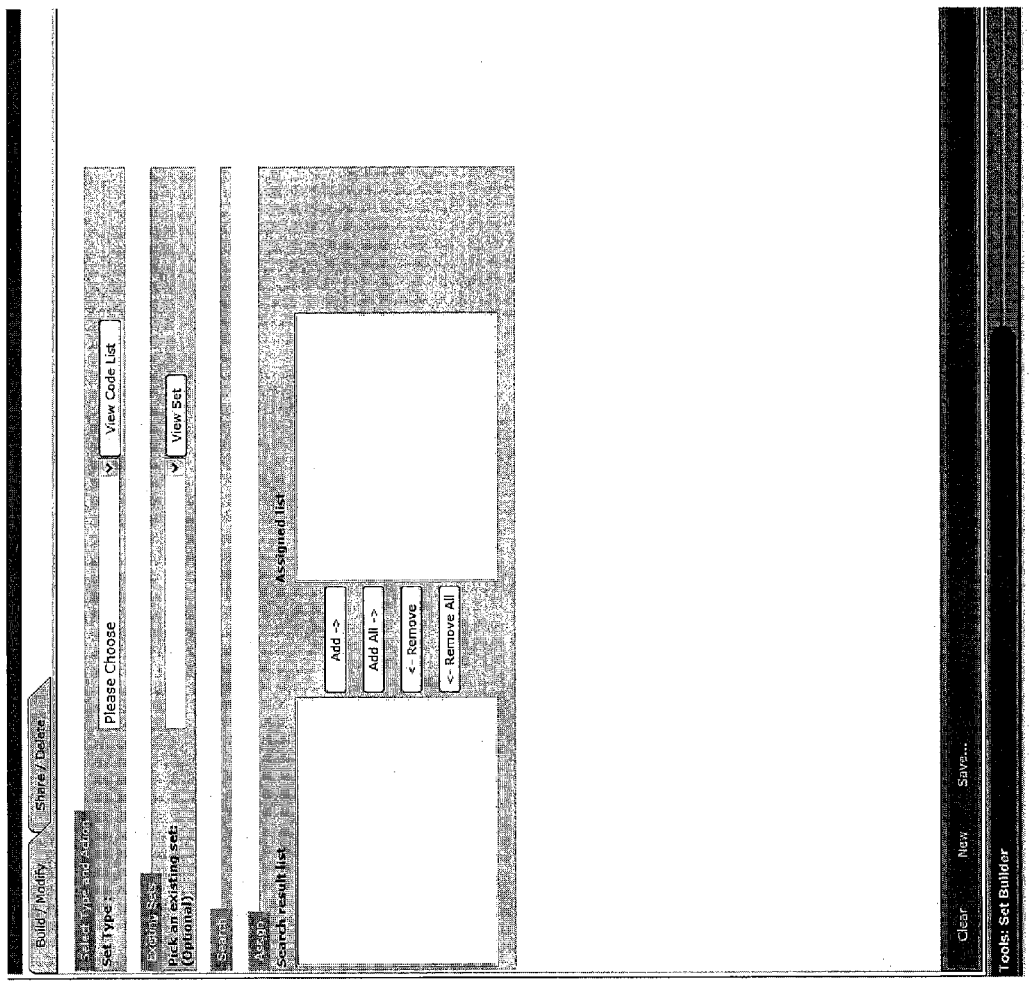
Figure 8:
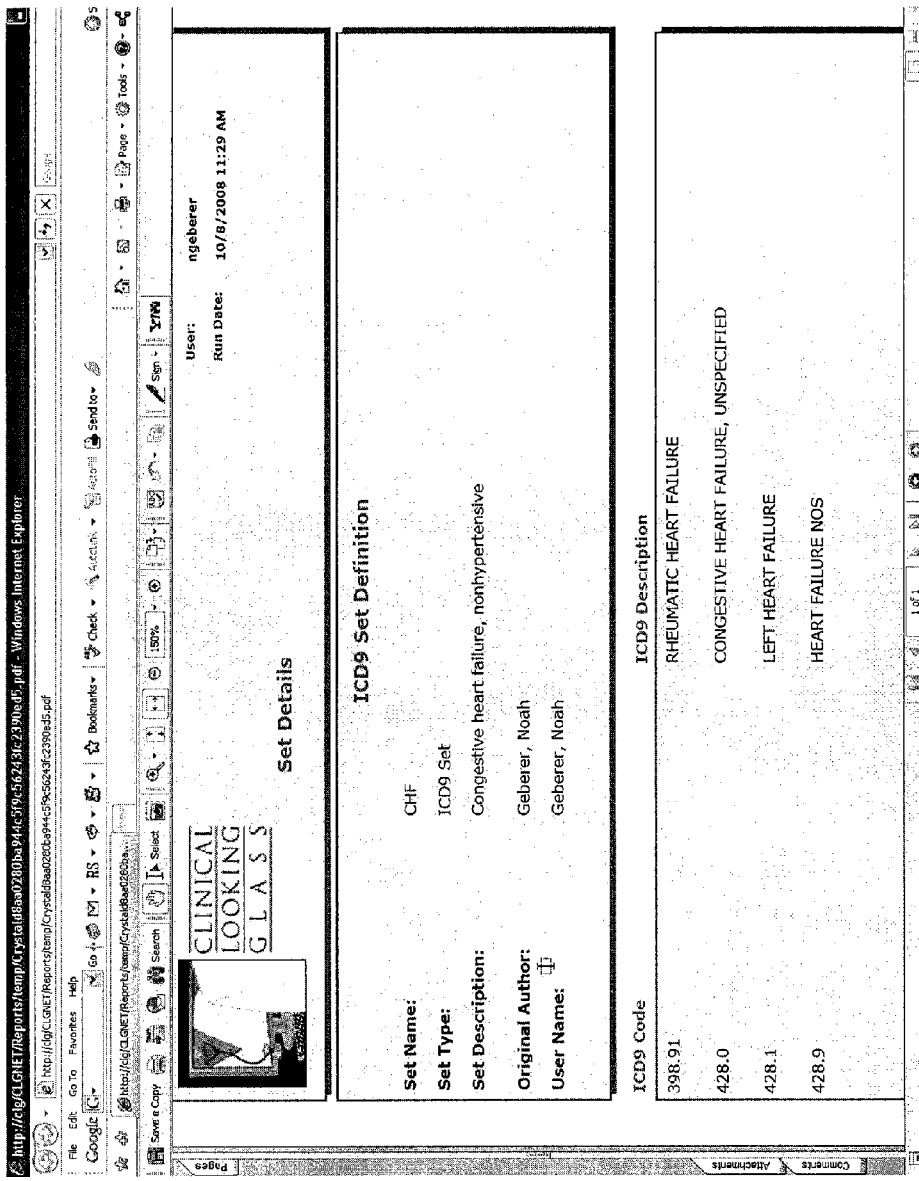

Selecting an ICD-9 set based on a subset AHRQ is achieved, for example using the drop down menu of FIG. 6 and selecting a code, such as CHF (congestive heart failure). To refer to the set of codes associated with the selected subset, the Set Manager button is selected, and the ICD-9 Set Definition Screen of FIG. 7 is displayed, which provides a View Criteria button which provides the list, preferably in a pop-up window, included in the ICD-9 set definition, as depicted in FIG. 8.

Figure 9:
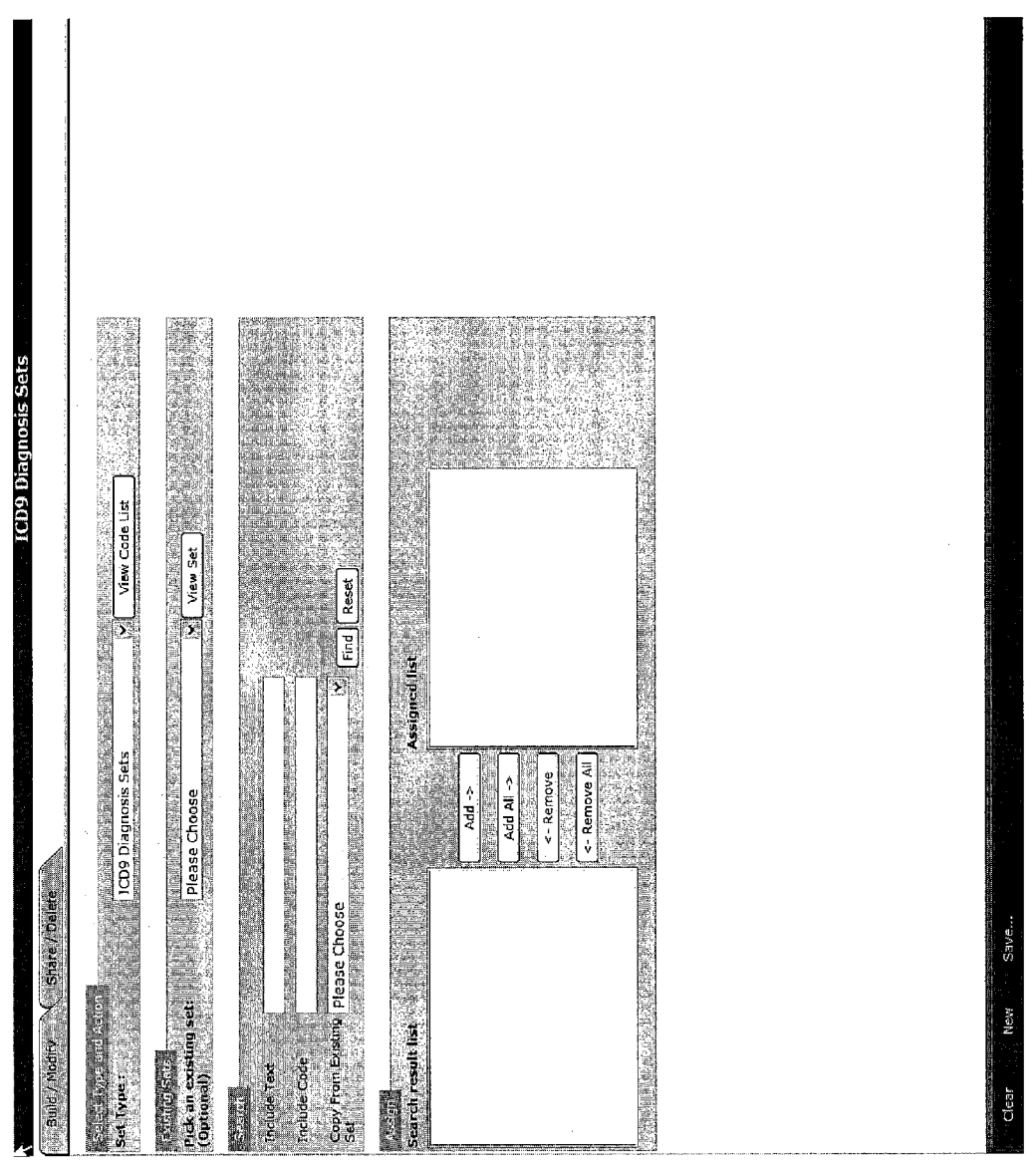
Figure 10:
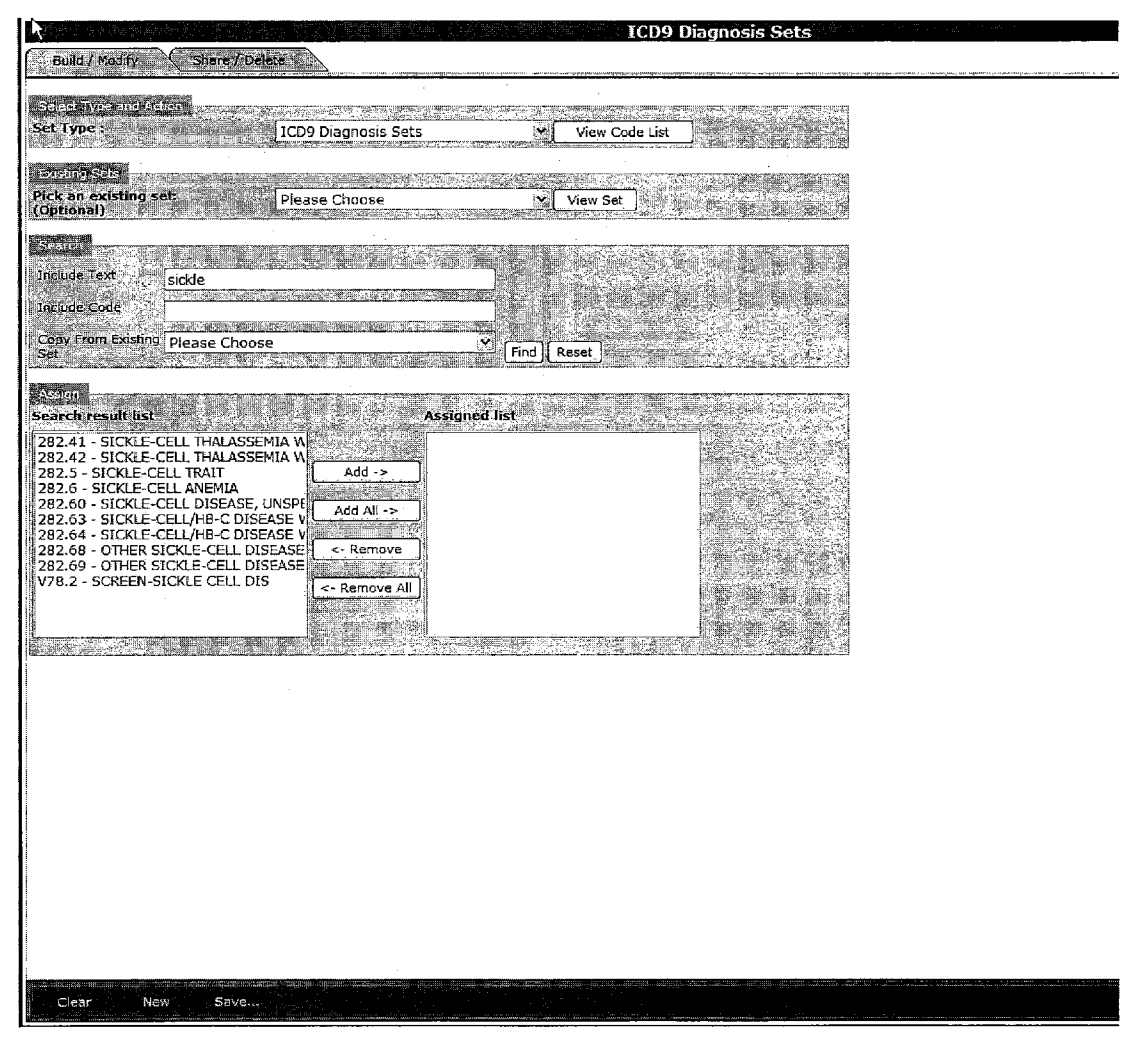
Figure 11:
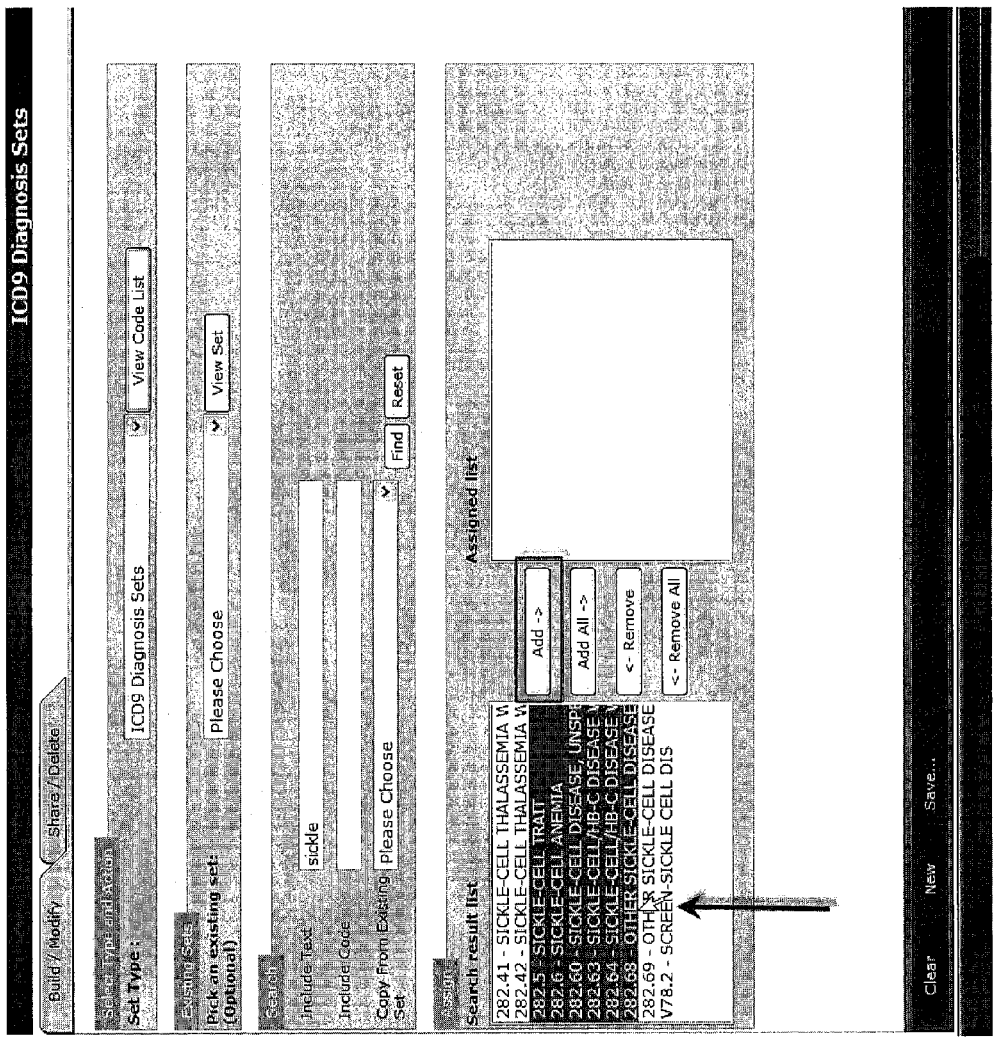

Referring again to FIG. 5, to build an ICD-9 set, the Set Manager button is selected, e.g., to obtain the ICD-9 Set Definition screen of FIG. 9. Searching for codes related to a condition can be achieved by entering a keyword in the text box, or entering a portion of the code, if known. To search by keyword, for example, "sickle," is entered into the Text box and a search is initiated, for example, by selecting the go button adjacent to the Text box, to obtain codes related to sickle, as shown in FIG. 10. FIG. 10 provides several ICD-9 codes related to sickle cell. Each code sought to be included in the set can be selected to add to a particular set, as shown in FIG. 11. Alternatively, a partial portion of the code is entered in the Partial Code box and searched to obtain code results. Preferably the ICD-9 set is saved to be used in connection with an analytic. In preferred embodiments, the sets can be shared with other users. To share a set, the Set Manager button is selected from the parameter entry screen of FIG. 5 and a set is selected to be shared. Sets can be shared with all users, or to some specifically identified users.

Referring again to FIG. 5, to the right of the ICD-9 set is the drop-down menu for type of diagnosis. The displayed default is Primary or Secondary. The options for this parameter include:

Admit—This is the admitting diagnosis, the diagnosis deemed accurate by the physicians on patient admission.

Primary—This is the diagnosis determined by the coders upon discharge as the primary diagnosis for the patient Secondary—This diagnosis was determined by the coders upon discharge as any non-primary ICD-9 diagnosis (2nd, 3rd, 4th . . . )

Primary or Secondary—This diagnosis would appear either as a primary or secondary diagnosis upon discharge.

Any—This diagnosis appears in either the admit, primary, or secondary diagnosis field.

Still referring to FIG. 5, more than one ICD-9 code or ICD-9 set can be selected to specify a diagnosis. Note that there is a second line for the ICD-9 Include grouping. This means that a user can combine two ICD-9 Includes for the diagnosis match, or have Clinical Looking Glass conduct a match based on one Include line or the other. Note that the third drop-down menu on the first ICD-9 Include line displays the word 'or'. A user can select either 'or' or 'and' on this drop-down menu. If 'or' is selected, the match will be performed on either the first ICD-9 Include line or the second, but will not require both ICD-9 codes to include a patient in the resulting study group. If 'and' is selected, the patient must have both diagnoses to be included in the study group.

When combining ICD-9 codes for a diagnosis so that two codes (or a combination of an individual code and a set, or two sets) determine the study population, use 'and', and then select the ICD-9 codes on the second line as in the first line. When selecting 'and' to combine both ICD-9 Include lines, it is important to understand that this means that only patients with both ICD-9 Include criteria will be included in the study group. The following example illustrates this.

Figure 12:
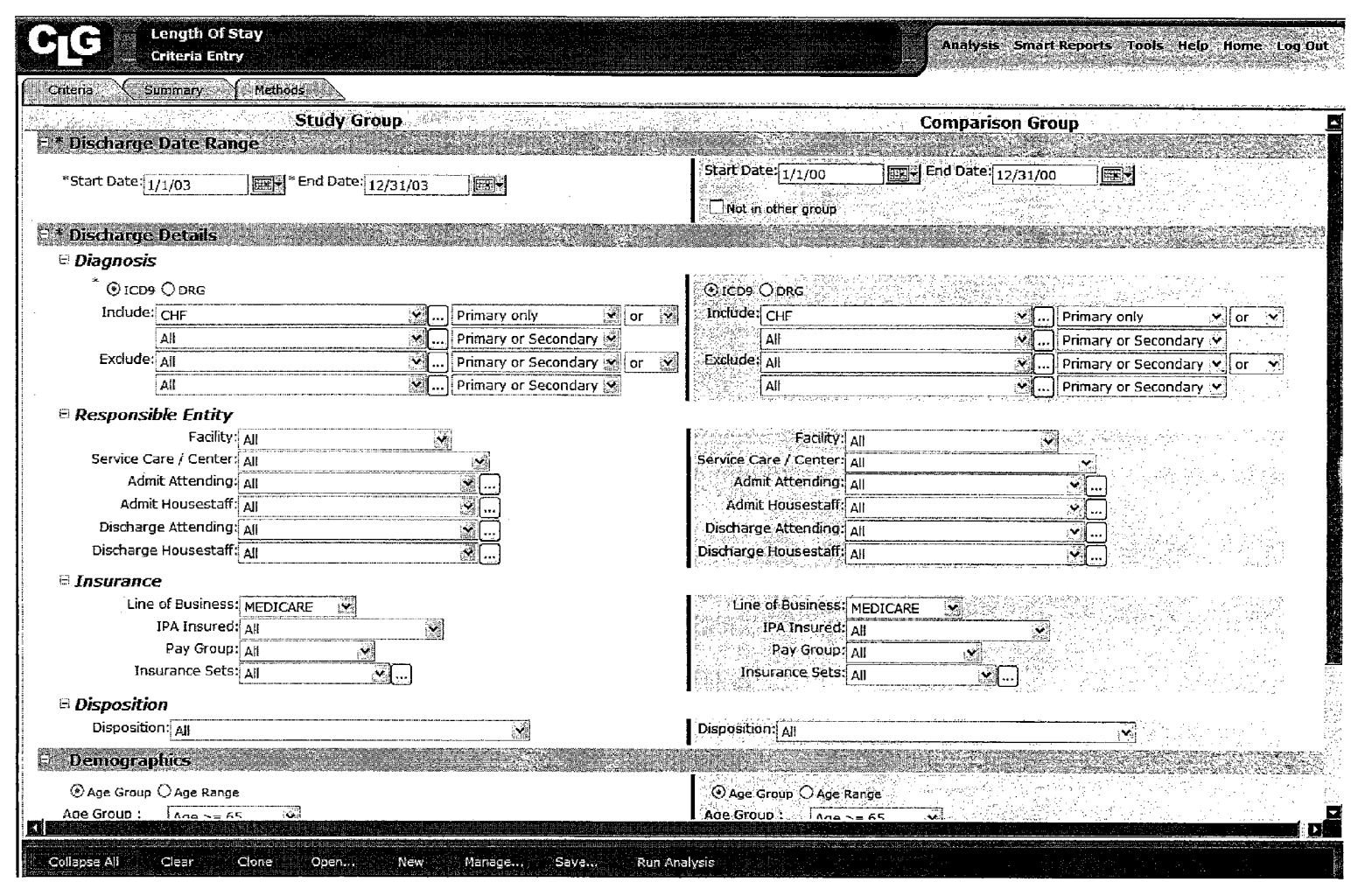

User defined sickle disease (USR: sickle disease) in any diagnostic position (primary, secondary, or admission diagnosis), then 'and' from the drop down menu, then 'pneumonia' on the second ICD-9 Include line, as shown in FIG. 12. After selecting the type of diagnosis based on ICD-9 Include, patients with particular ICD-9 codes can be excluded from the study, as follows:

Enter the ICD-9 Exclude data is entered in the ICD-9 Exclude data entry points, in substantially the same way the ICD-9 Include data is entered. Entering Exclude data means that when the match is conducted on the patient database, any patients with the Exclude diagnosis will be excluded from the cohort results. Note again that there are two lines for ICD-9 Exclude as there are for the Include data, allowing for the 'and' or 'or' combination.

Referring still to FIG. 5, additional parameters relating to patient data are entered, such as the timeframe, demographics, age, gender, facility/care center, service/care center, managed care, line of business, label, and/or comparison group. The timeframe field limits the patients considered for analysis to be those patients discharged in the time interval. Demographics can be for example, a pre-specified cohort. If the cohort was previously defined, e.g., using the cohort builder, further described herein, the cohort is selected from a drop down menu. If there is no pre-specified cohort, the default for the Based on Stored Cohort, is left as is, e.g., "No cohort restriction". Patients may also be limited by age and gender. The Facility/Care Center and Service/Care Center may be selected using a drop down menu, or set at a default setting of all facilities. The Managed Care setting can be specified using a drop down menu, e.g., managed care, non-managed care, or no restriction. Line of business includes all lines of business, commercial, Medicare or Medicaid. The line of business refers to the primary payer in the system. A label is preferably used for identifying graphs generated by the analytic. In some instances, a parameter related to a comparison group is entered to compare to a study group. The comparison group parameters are entered in substantially the same manner as the study group parameters were entered, as described herein in reference to FIGS. 5-12, with the exception that for the timeframe, checking the checkbox "Not in other group", indicates that patients in the study group are excluded from the comparison group.

When all parameters have been entered for a Study Group and optionally for a Comparison Group, the analytic is run by selecting the Run Analysis button of FIG. 5. In the event that there are no patients that meet the entered criteria, no results are returned. When there are patients that meet the entered criteria, a results page is displayed, for example, as shown in FIGS. 13-16. As shown in FIGS. 13-16, each results page has tabs for Methods, Criteria, Demographics, and Outcomes. The tab for Methods leads to the view shown in FIG. 13, describing the formal methods used in producing results inclusive of the statistical tests.

Figure 14:
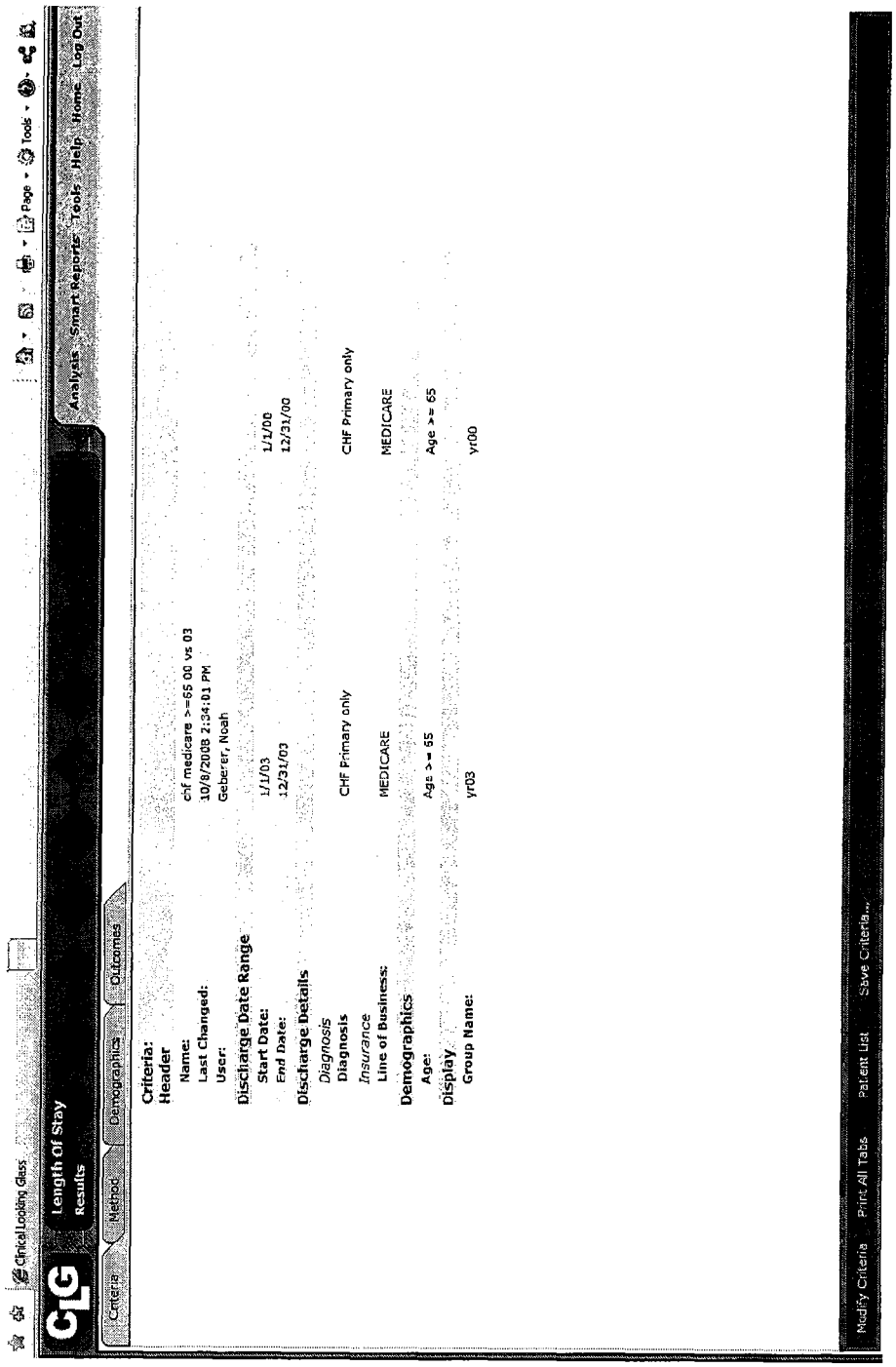

The tab for Criteria leads to the view shown in FIG. 14, summarizing the criteria selected by the user in the parameter entry screen, thereby permitting the user to check whether the parameter or information submitted was intended. To add new criteria, the New Criteria button on FIG. 14 is selected to return to the parameter entry screen of FIG. 5.

Figure 15:
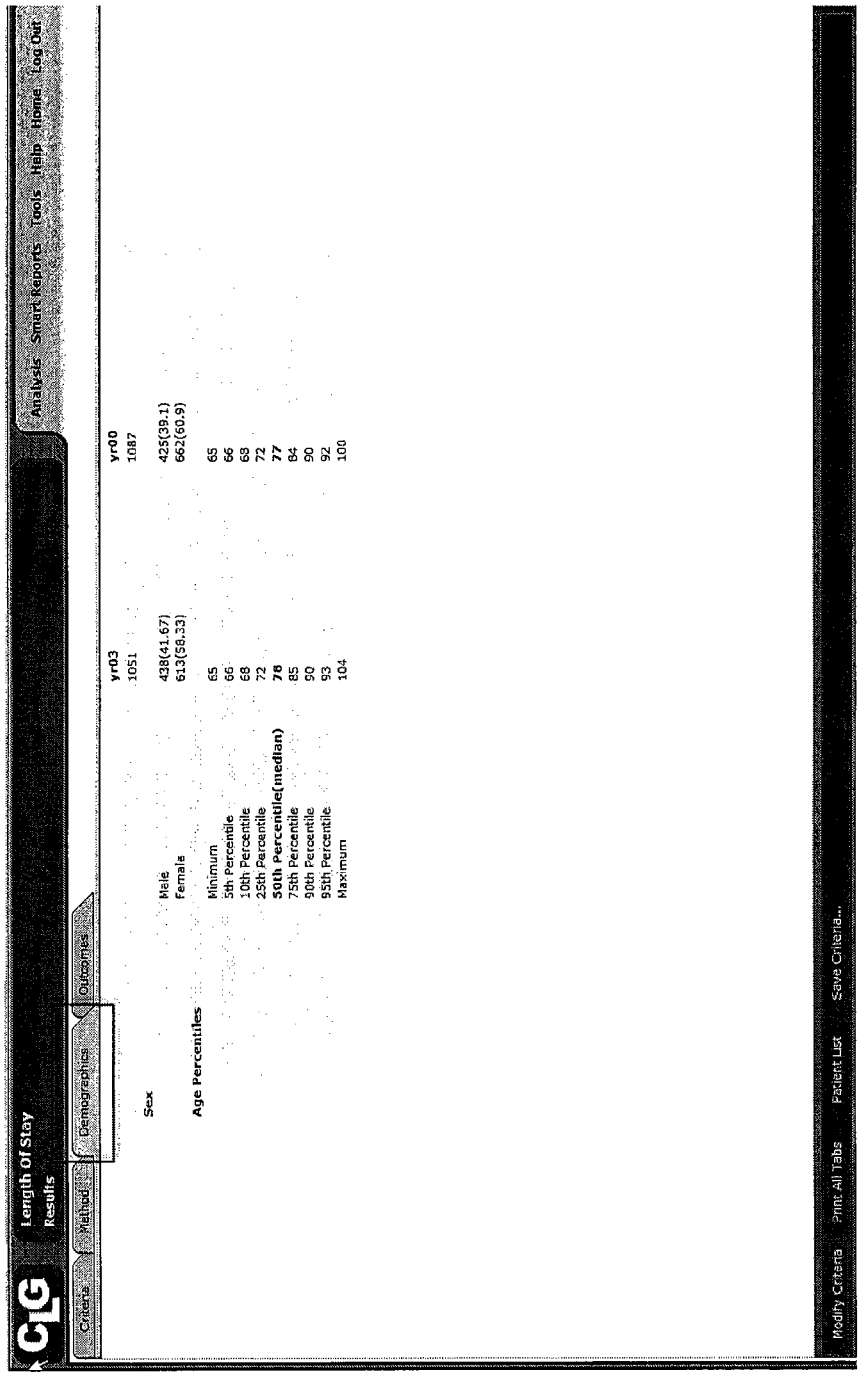

The tab for Demographics leads to the view shown in FIG. 15, providing the breakdown by gender and percentiles in age. It also provides an option to display all cohort patients in a spreadsheet. On the Demographics screen, of FIG. 15, the total number of patients in the resulting cohort is displayed at the top of the screen, directly underneath the label assigned to the cohort, originally entered in the Parameter Entry screen (FIG. 5). The results of the Demographics screen are displayed by gender and age. The results by gender are displayed by absolute number, immediately followed by percentage in parentheses. The results by age are displayed in tabular format by quantile. The 50th quantile is the median value. In the example of FIG. 15, the 50th quantile of age is 75 years and the 75th quantile is 83. This means that 75% of the patients in this group are 83 years of age or less and 25% are greater than or equal to 83 years of age.

To view a list of the patients in the resulting cohort, the Patient List button is selected to obtain a spreadsheet which lists patients in the cohort. The list includes information related to the patient, such as: name, length of stay in days, Study Group or Comparison Group, age, account number or other identifier, admission date and time, discharge data and time, medical record number, date of birth, gender and/or race. The patient list information may vary between the analytic options and is preferably kept confidential. In preferred embodiments, portions of the patient list information can be printed, and the highly confidential information is not printed.

Figure 16:
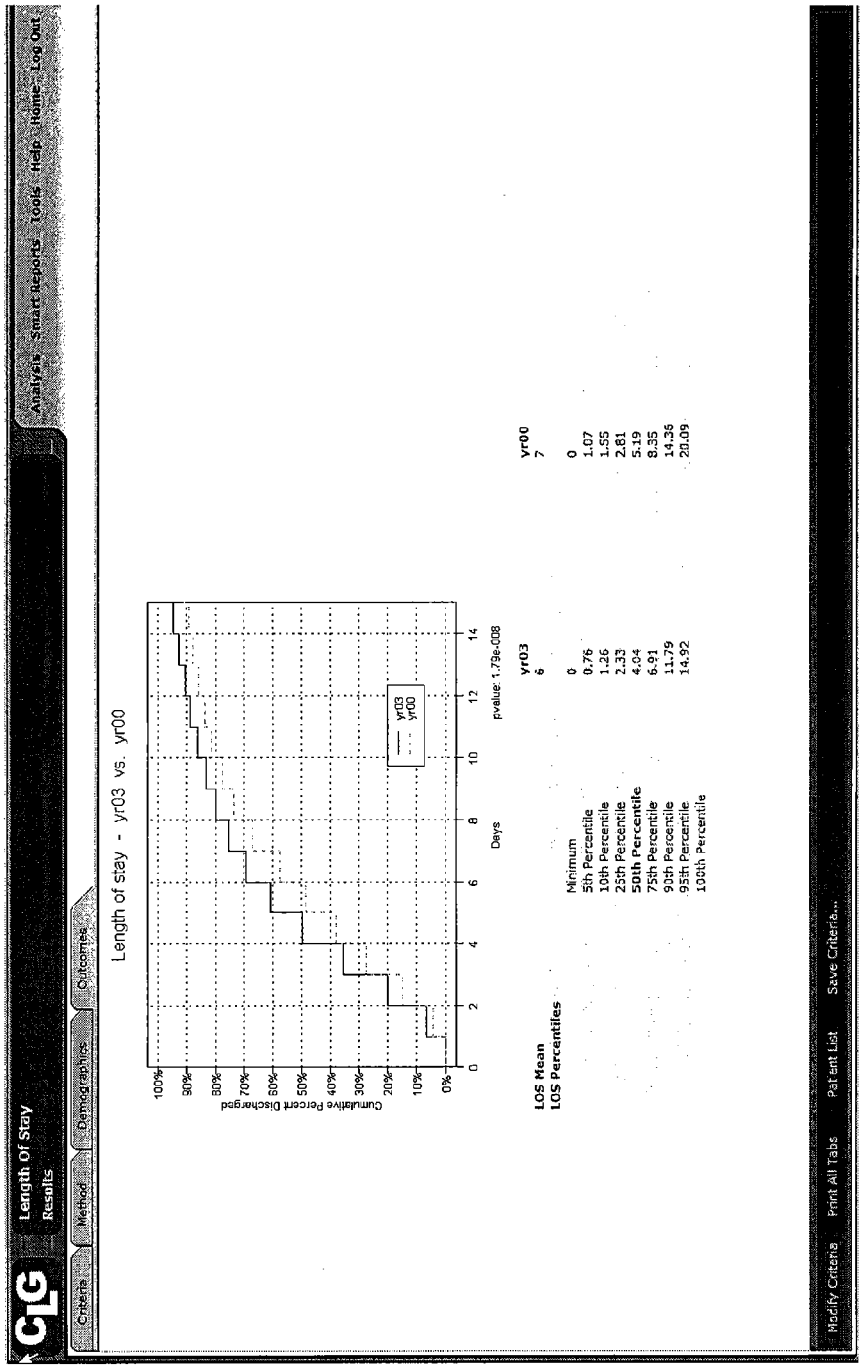

The tab for Outcomes leads to the view shown in FIG. 16, which graphs the outcome results for the entered criteria. The graph is a pictorial representation of the results. Note that data points are directly correlated with specific quantiles on the Y-axis whose label is Cumulative Percent Discharged. Directly below the graph are two measures: LOS Mean, which refers to the mean length of stay for this cohort and LOS Quantiles, which refers to the specific quantiles and associated number of patients for each quantile.

Figure 17:
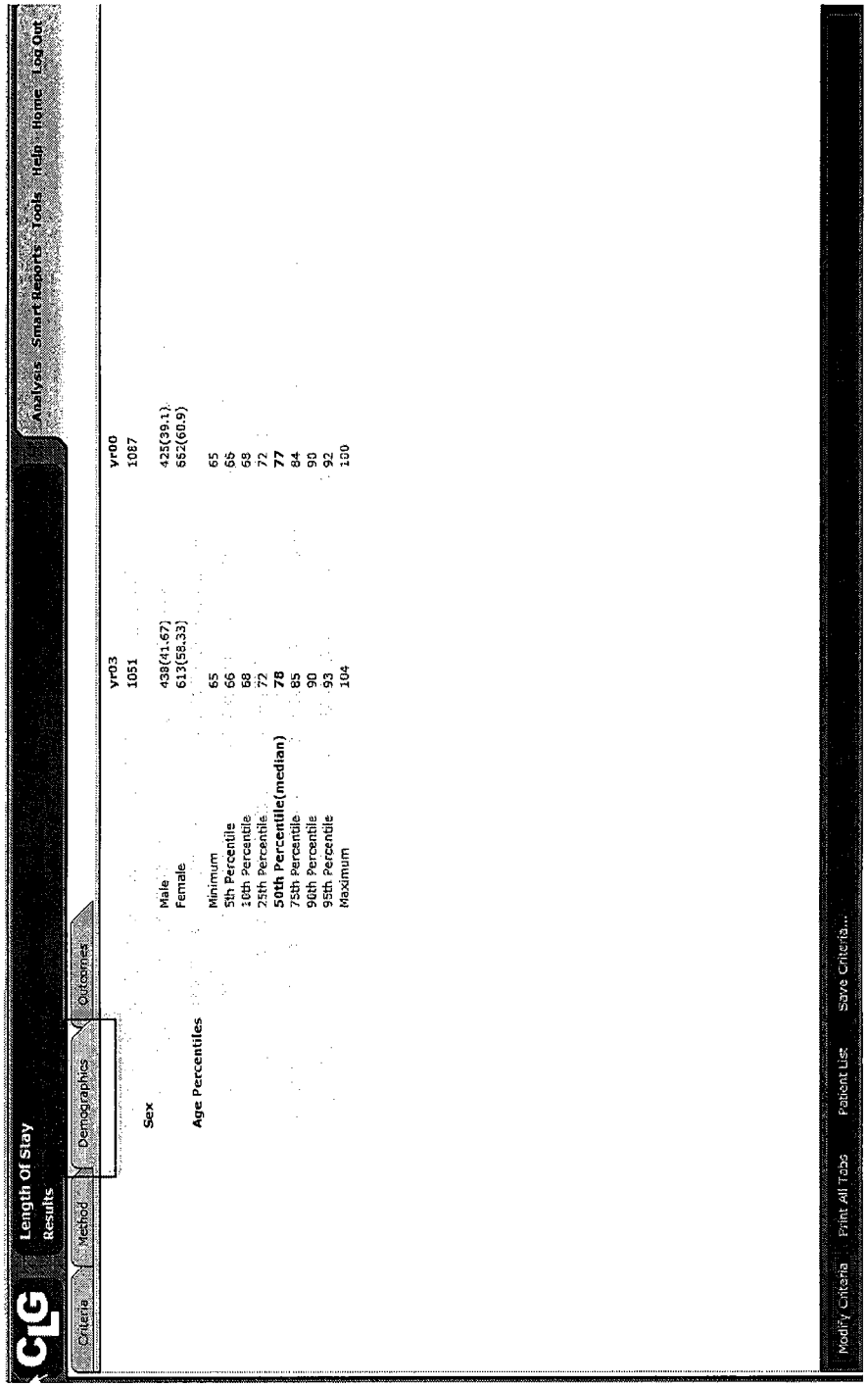
Figure 18:
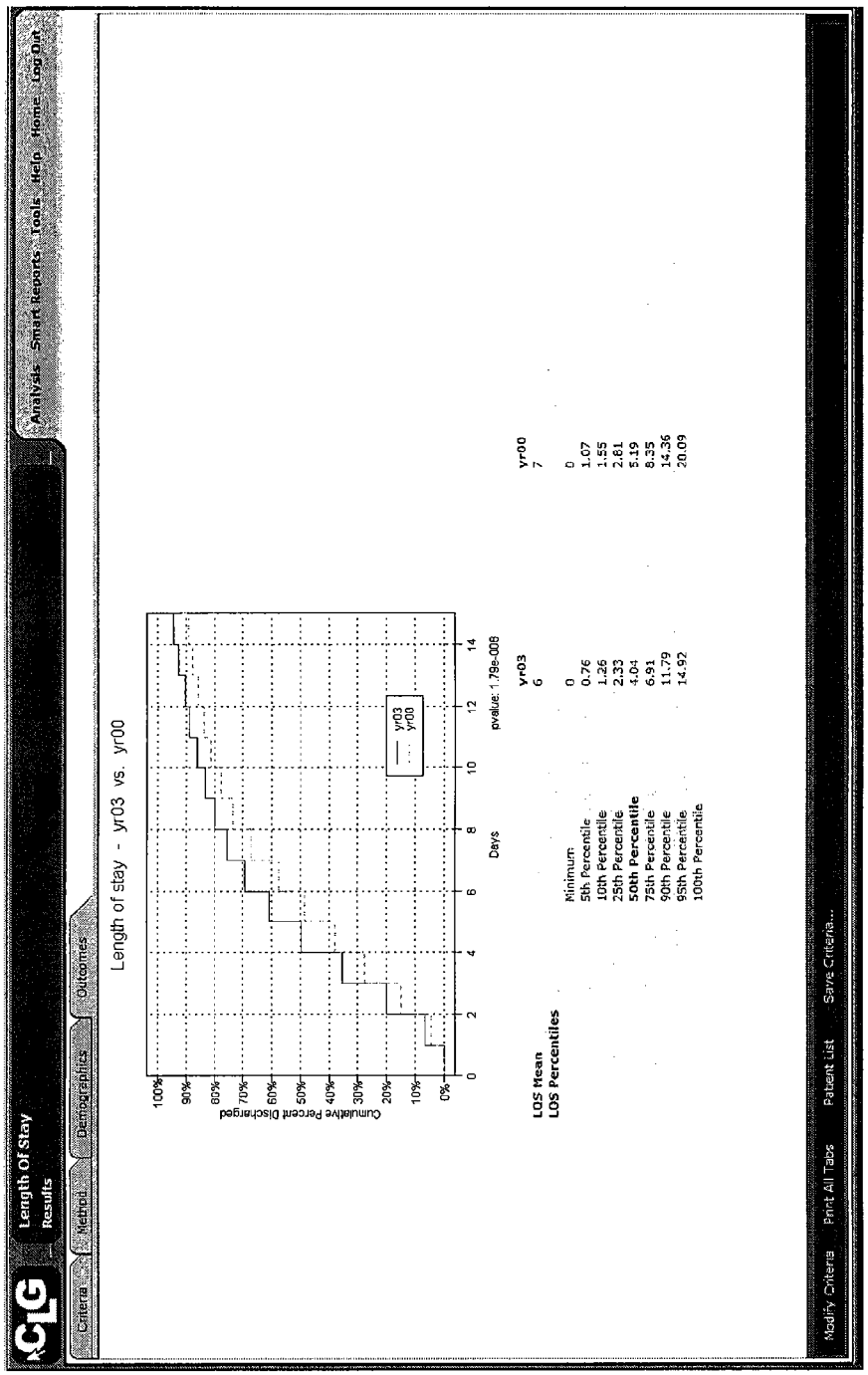

FIGS. 13-16 provide results for a study group. In FIGS. 17-18, results are provided for a two group study, a study group and a comparison group. The results of FIGS. 17-18 are for a single ICD-9 set based on CHF to assess LOS over two time periods, January 2001-September 2001 against January 2000-September 2000. FIG. 17 depicts Demographics results for each year in the comparative study, which indicates that patient populations for each of the two groups respectively are yr2001: 1237 and yr2000: 1226. Additional information related to each patient included in the groups or cohort, the patient list button is selected to obtain a spreadsheet. FIG. 18 depicts graphed results of the comparative study. In preferred embodiments, the graphed result includes a p-value delineating statistical significance. The results show that the LOS for CHF was shorter in 2001 than in 2000, indicating that hospitalization stays were shorter. An indication of whether quality of care was compromised by the shorter hospitalization, is shown by the readmission rate—or return to the hospital post discharge—was greater.

The quality of care issues that can be addressed by the LOS analytic include at least the following. The LOS analytic obtains lists of patients to find patients who may have specific diagnoses for chart review of process of care quality, ultimate outcomes, and satisfaction follow up studies. Additionally, the LOS analytic can be used for disposition studies relating to death/nursing home/rehabilitation by comparing patients in one category with others to see if some intervention might have been appropriate. Also, studies of timeliness of service for inpatient care or coordination of discharge service needs can be performed in charts identified by the LOS analytic. Comparisons can be made between parameters, such as: age, gender, clinics, time frame, managed care status, diagnoses, primary payer (medicaid/medicare/commercial), and hospital.

Readmission Analytic

Figure 19:
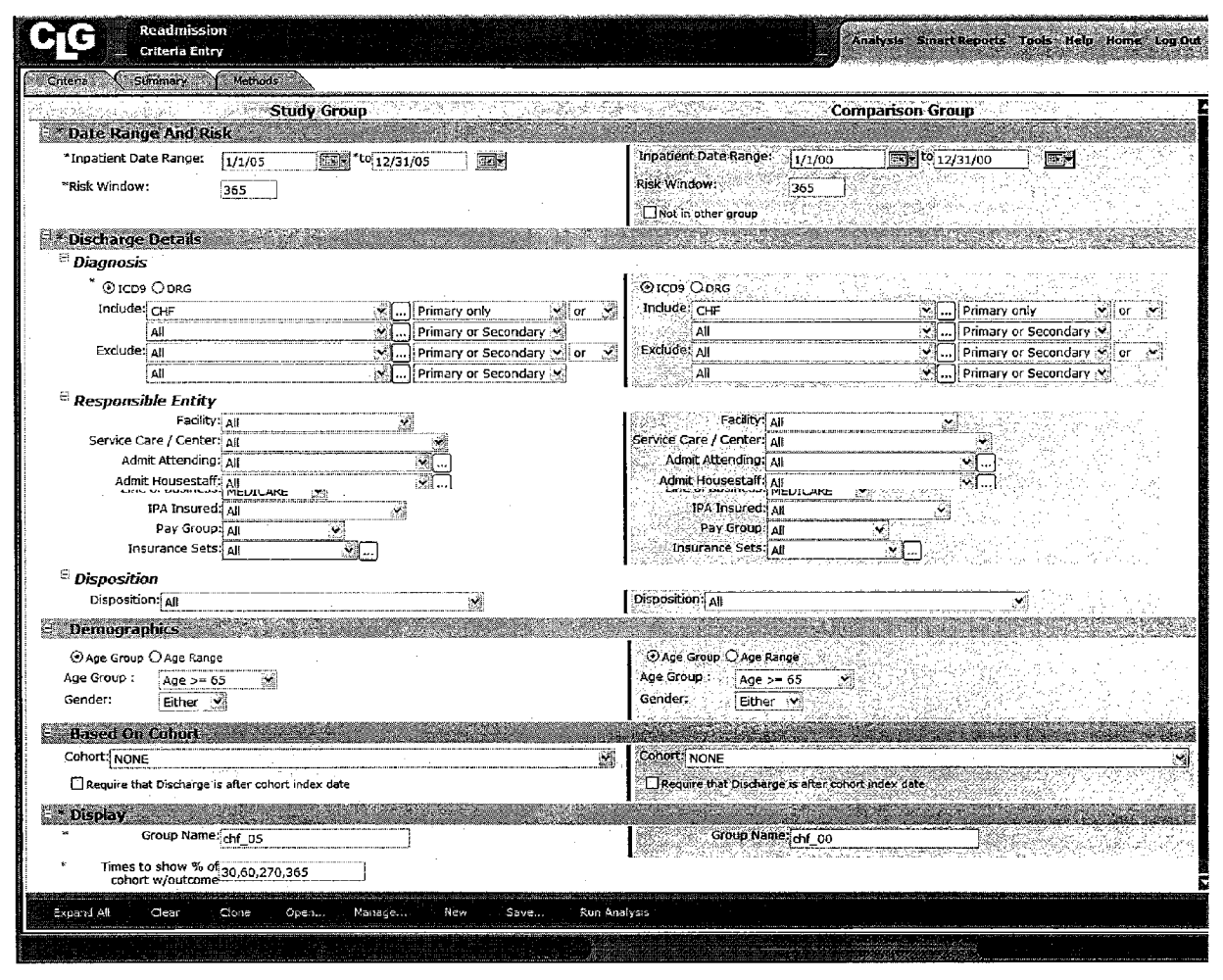

The Readmission analytic is similar to the Length of Stay analytic with respect to, for example, entering criteria and in the layout of the results. Some of the differences are described below. The Parameter Entry screen for the Readmission analytic depicted in FIG. 19 of the LOS analytic differs from the LOS Parameter Entry screen, shown in FIG. 5. The first difference is the Risk Window field (FIG. 19). This field determines the length of the x-axis outcome—the maximum number of follow up days the graph will consider. Risk Window is the duration of time to consider for readmissions. Some of the calculations in the outcome require input related to how long after the index admission to count readmissions. In addition, there is a field Times to show % of cohort with outcome. This is a field that instructs the system to create a table that looks at the cumulative percent of patients that have been readmitted by the number of days post discharge specified in the field. After each parameter entry field is input, the analytic is run by selecting the Run Analysis button.

Figure 20:
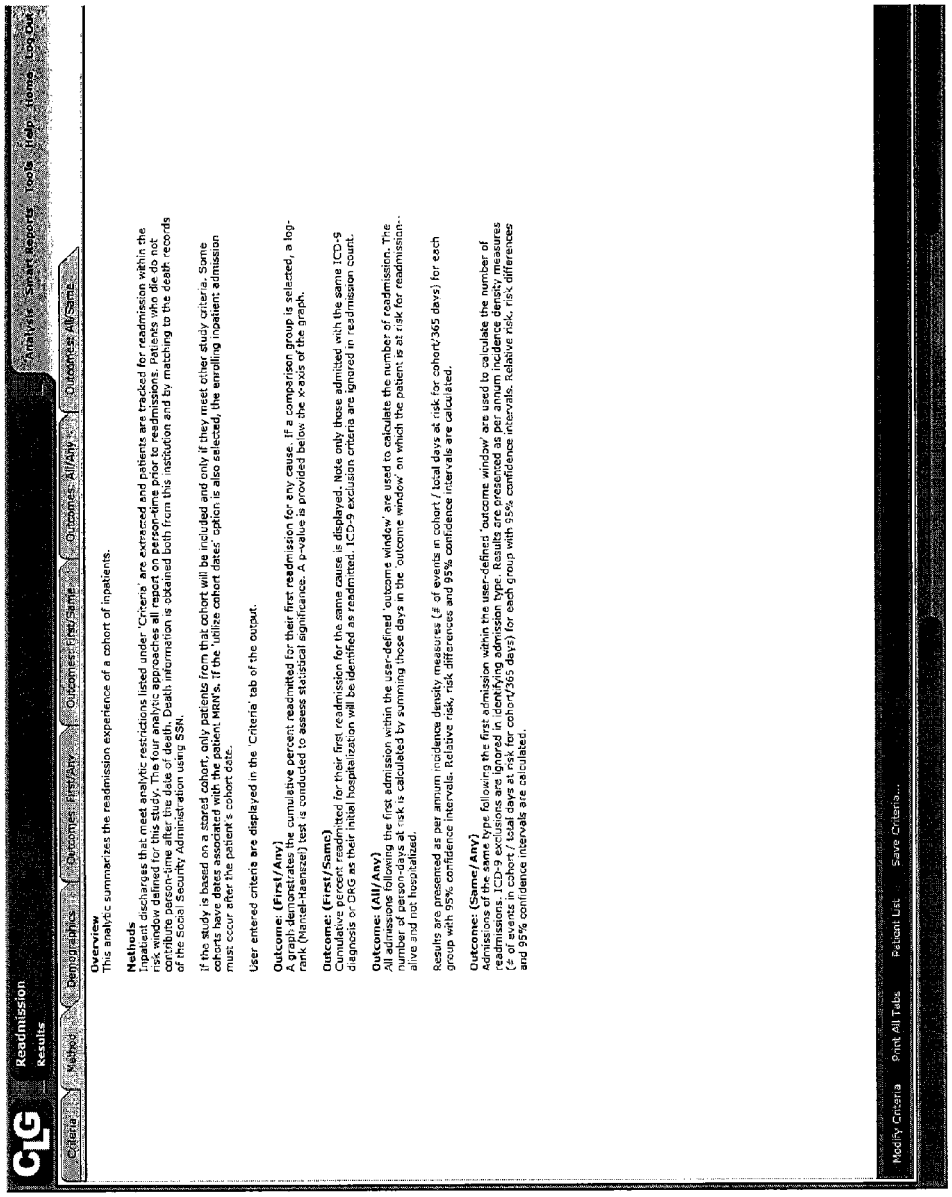
FIGS. 20-22 depict screenshots of results screens according to an embodiment of the invention.
Figure 21:
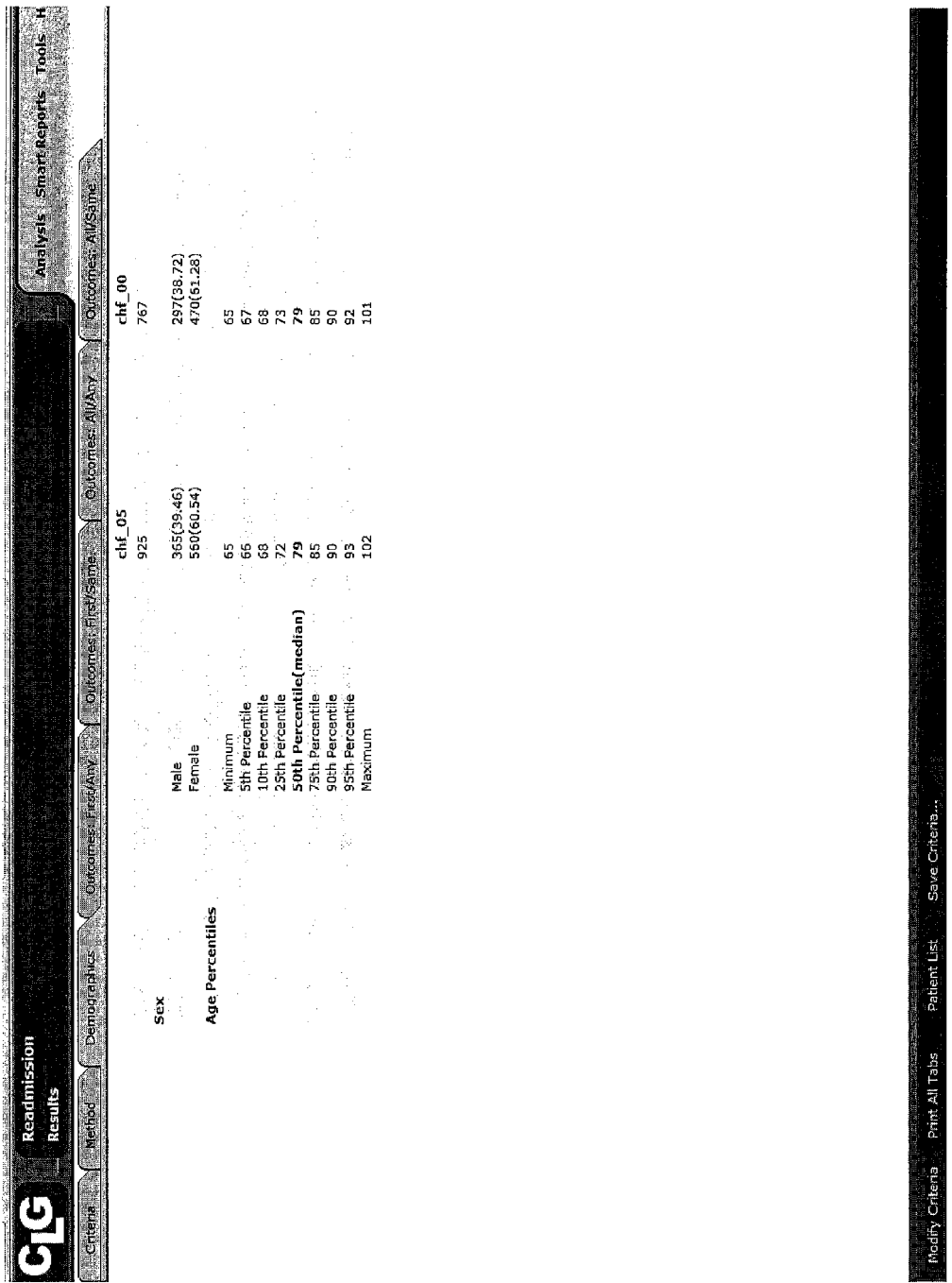
Figure 22:
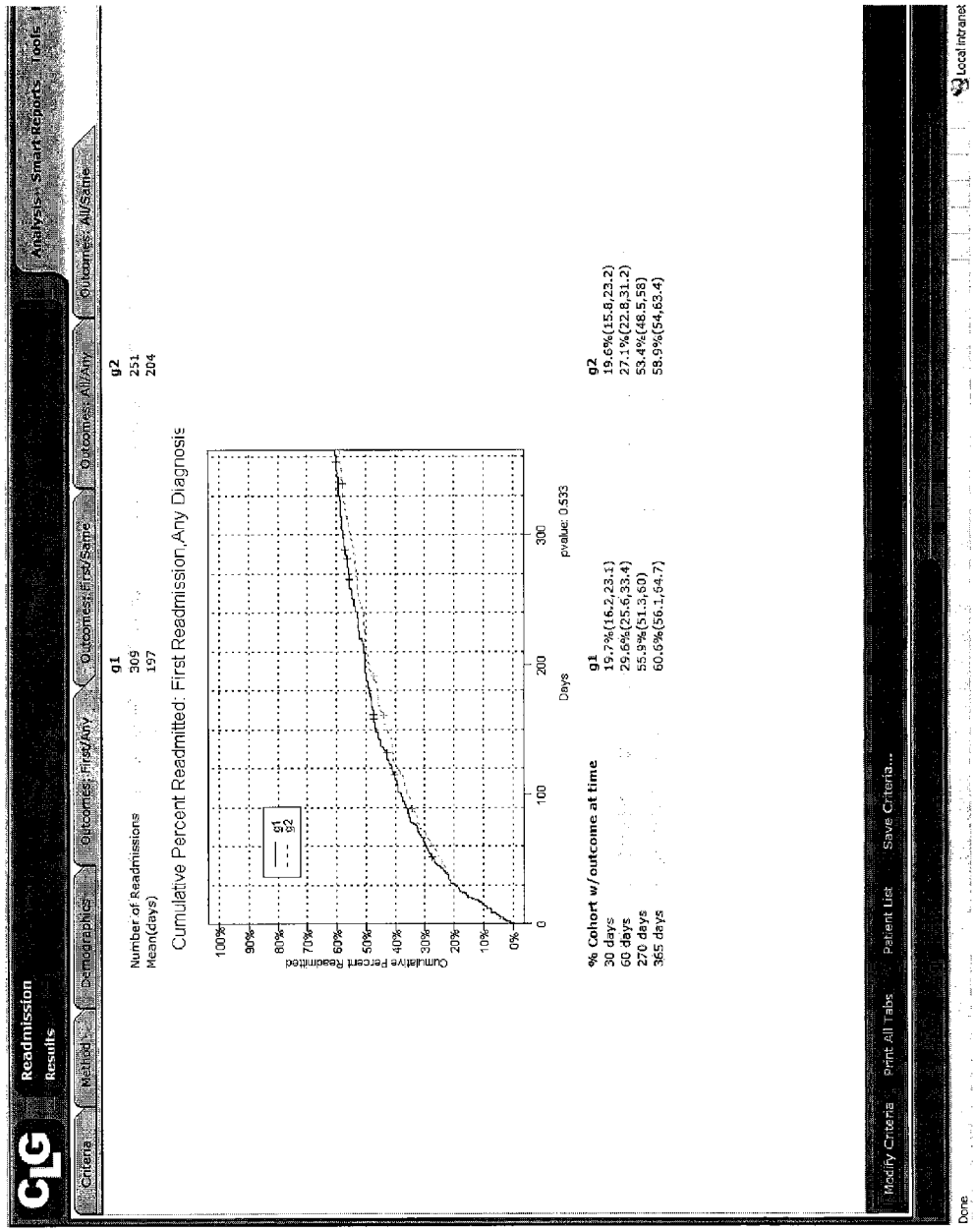

Results of the Readmission analytic are depicted in FIGS. 20-22. FIGS. 20 and 21 depict the Readmission analytic Methods and Demographics results, respectively, which are similar to the corresponding Methods and Demographics results pages of the LOS analytic, depicted in FIGS. 13 and 15, respectively. The Patient List, which can be viewed by selecting the Patient List button from the Demographics screen (FIG. 21), in spreadsheet format includes the following variables (these differ somewhat from those of other analytics): date of discharge, account number, event any—the value is zero, if there are no subsequent readmissions in the risk window, and 1 if there is at least one subsequent readmission, risk any—days in risk window that patient is at risk for readmission until first actual readmission regardless of diagnosis, event specific—the value is zero if there is no subsequent readmission that matches diagnosis to the index and 1 if there is at least one, risk specific—days in a risk window that the patient is at risk for readmission until the first actual readmission with matching diagnosis, event count any—number of readmissions over the patient risk window regardless of diagnosis, event count specific—number of readmissions over the patient risk window with matching diagnoses, all risk—all days in the risk window when the patient is at risk for readmission, MRN (medical record number), age, or gender. Preferably, access to the patient information is restricted to authorized personnel only, to insure HIPAA (Health Insurance Portability and Accountability Act) compliance.

Additionally, Criteria results for the Readmission analytic are substantially the same as the corresponding Criteria results for the LOS analytic, depicted in FIG. 14. The Outcomes results for the Readmission analytic depicted in FIG. 22, however, are somewhat different than the LOS Outcomes results (FIGS. 16 and 18). More specifically, the Outcomes results are expanded to reflect the various possible readmission scenarios.

The total number of readmissions is shown at the top of FIG. 22. The graph displays the percentage of all patients in the specified cohort who were readmitted within a one-year period. The quantiles displayed below the graph provide statistics for all patients readmitted within a one-year period by specific time intervals selected by the user. If two groups are compared, there will be a p-value comparing the two group's performance.

Outcomes for the Readmission analytic can include the following categories: First/Any—Time to first readmission with any diagnosis, First/Same—Time to first readmission with the same diagnosis specified for this study, All/Any—Time to all readmissions with any diagnosis, and All/Same—Time to all readmissions with the same diagnosis specified for this study. The first two outcomes, First/Any and First/Same, examine the cumulative percent of the patients who were readmitted (y axis) by the time elapsed from discharge indicated on the x-axis. First/Any counts every readmission as a readmission regardless of the cause. First/Same requires that the readmission have the same DRG or same principal diagnosis as the original to be counted. For example, a person who was discharged after a hospitalization for CHF who was then readmitted for pneumonia would not be counted in First/Same but would be counted in First/Any. Note that there are detailed descriptions of these different types of outcomes on the Readmission Results page (FIG. 22). All/Any and All/Same count the all the readmissions over the risk window and divide this number by the number of patient days spent out of the hospital. This incidence density is an indicator of the frequency of readmission. The relative incidence density is provided as a relative risk (with a 95% confidence interval). The risk difference of the incidence density is also provided with its 95% confidence interval. The null finding will include 1 and zero respectively in the two confidence intervals. As in the first two tabs, Any counts a readmission for any cause, and Same requires that the readmission be for the same cause.

Generally, readmission intervals can be used as a measure of success in treating patients effectively. A longer interval to readmission indicates better success. The Readmission analytic provides patient lists of patients with specific readmission times and diagnoses for chart review of process of care quality, ultimate outcomes, and satisfaction follow up studies. The satisfaction studies could include assessment of in hospital planning for discharge, appropriate medications at discharge, and follow up in the community. Data sources could include: the hospital chart, last word data (front end review of hospitalization), last medications given in hospital, clinic charts, social service notes, or other data. Hospitalized residents can be involved in the process of assessing the quality of longitudinal service provided.

Laboratory Outcome Analytic

The Laboratory Outcome analytic generates information allowing a user to determine how well a specified cohort achieved a desired therapeutic endpoint. The analytic also provides a report identifying the patients who failed to achieve the desired endpoint to allow practitioners to follow up. This and other reports disclosed here are preferably available and can be provided on a real time basis. As described herein, the Laboratory Outcome analytic provides information related to treating patients with conditions such as HIV, diabetes, and LDL with diabetes to identify failures by clinics and permit targeted remediation efforts. Additionally, the analytic can be used to find patients with specific diagnoses for chart review of process of care quality, ultimate outcomes, and satisfaction follow up studies.

Figure 23:
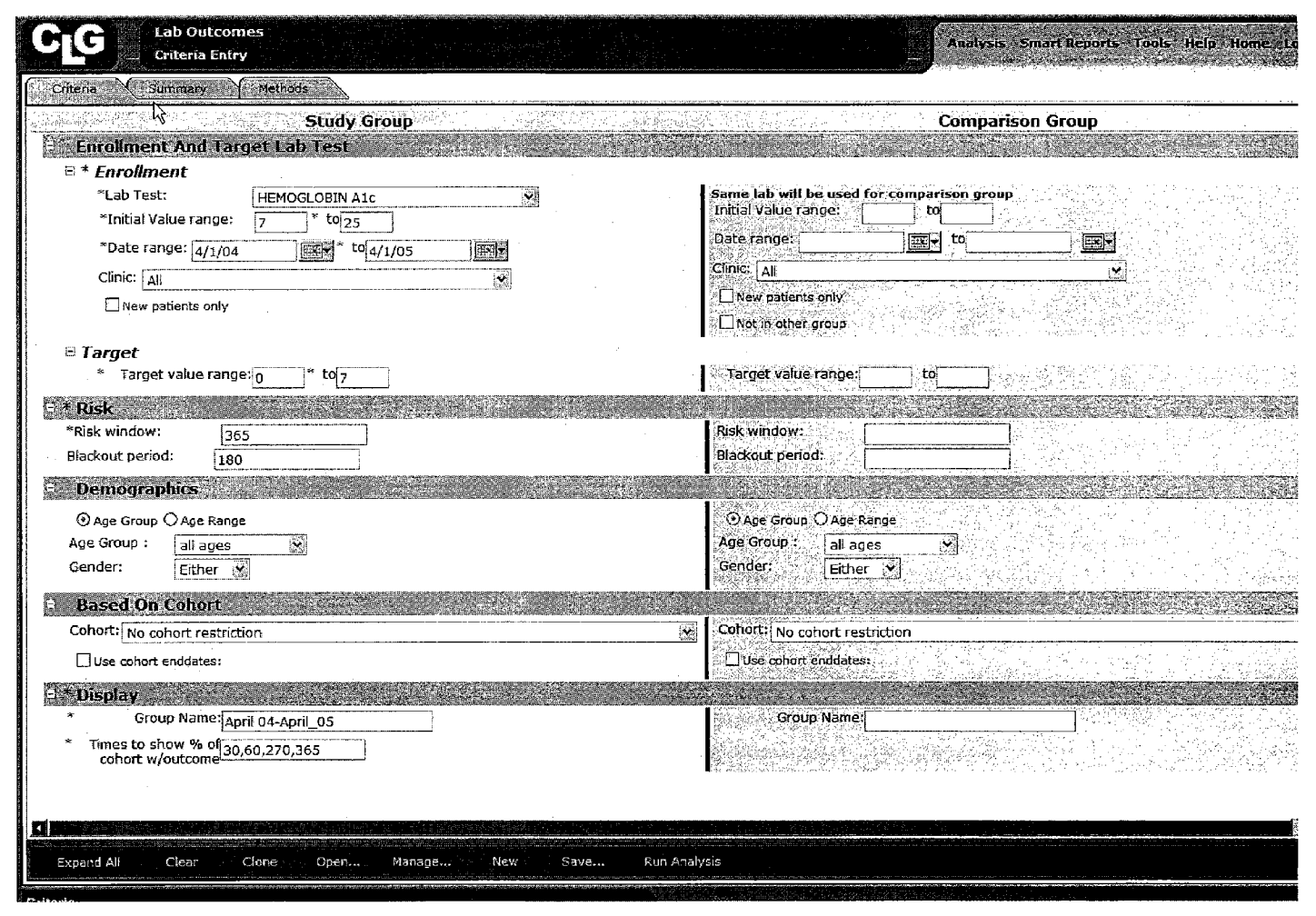

The Parameter Entry screen for the Laboratory Outcome analytic depicted in FIG. 23 is similar to the Parameter Entry screens for LOS (FIG. 5) and Readmission (FIG. 19), the differences are discussed herein. In FIG. 23, information relating to two groups is input relating to Hba1c for two groups to run a comparison of Hba1c data.

A Test field is provided for inputting parameters related to laboratory outcomes, using a drop down menu. Examples of Tests include: HbA1c, LDL with HbA1c>9, or HIV VL. The analytic can restrict the analysis to new patients only, who did not have any laboratory values stored in the hospital information system prior to the stated time interval, by selecting the New Patients Only button. A Start Range field is provided for inputting low and high values relating to laboratory test ranges on which the analytic is run. A Target Range field is provided for inputting a target range, using high and low values, considered a success for outcomes calculations. An Outcome Window field provides the outer limit of time by which the targeted lab value must be reached for the patient's result to be counted as a success. If the patient does not have at least this much calendar time for follow up, the patient is considered censored and is not counted as either a success nor failure no matter what actual lab values were achieved. A Blackout Period field is provided to input parameters related to the number of days that must pass before a specific laboratory result can be evaluated. Prior to this time any repeat test is considered irrelevant. This interval takes into consideration the biological time that must elapse before an appropriate intervention could be capable of generating a meaningful change in a laboratory value. A field for Outcome Evaluation—Evaluation Interval is provided to input parameters related to a time interval. Laboratory tests evaluated for achieving the targeted outcome are preferably drawn between the elapsed blackout time and the outcome window time, or "evaluation interval". The first success in the evaluation interval is considered the success for the purpose of calculating time to achieving a success. If no success is recorded, then the last failure in the interval is considered the failure of record for the interval. If no laboratory test is obtained between the blackout time and the evaluation window time, the patient is considered lost to follow up. If, however, there was inadequate calendar time for the patient to be followed to the end of the outcome window, then neither failure nor success within the less than complete evaluation interval is counted in the proportion of patients with success (See Outcomes Results in FIG. 25). These patients are included in the Cum pct success tab with success being the first success and censored being the end of calendar time that has passed without a success.

A field Times to Show % of Cohort With Outcome is for inputting parameters related to the desired number of days for which a cumulative percent of the cohort achieved the desired outcome (e.g., success). More than one number may be entered and any number that falls within the blackout period will be ignored. The default display for this field, as shown in FIG. 23, includes four values, 30 days, 60 days, 270 days and 365 days. After each parameter entry field is input, the analytic is run by selecting the Run Analysis button.

Figure 24:
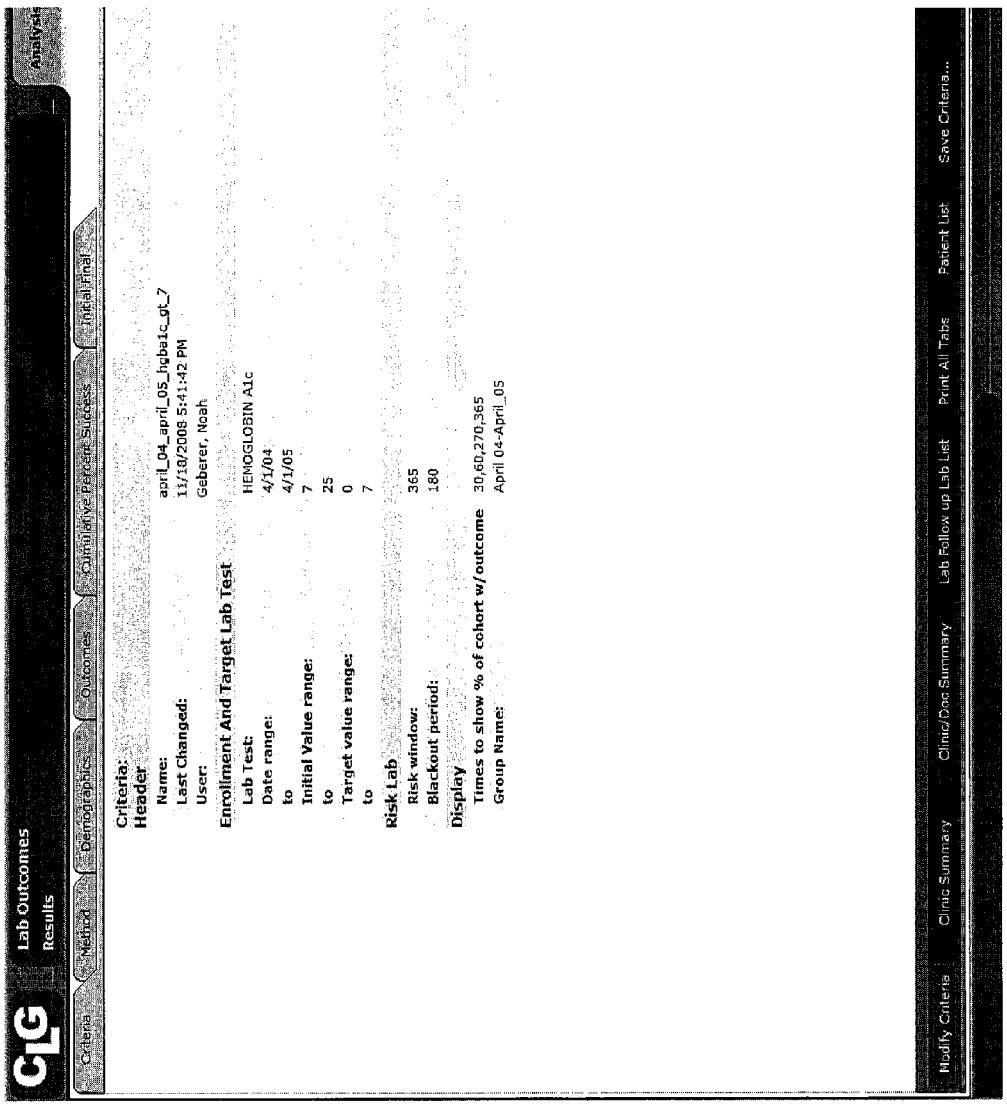
FIGS. 24-25 depict screenshots of results screens according to an embodiment of the invention.
Figure 25:
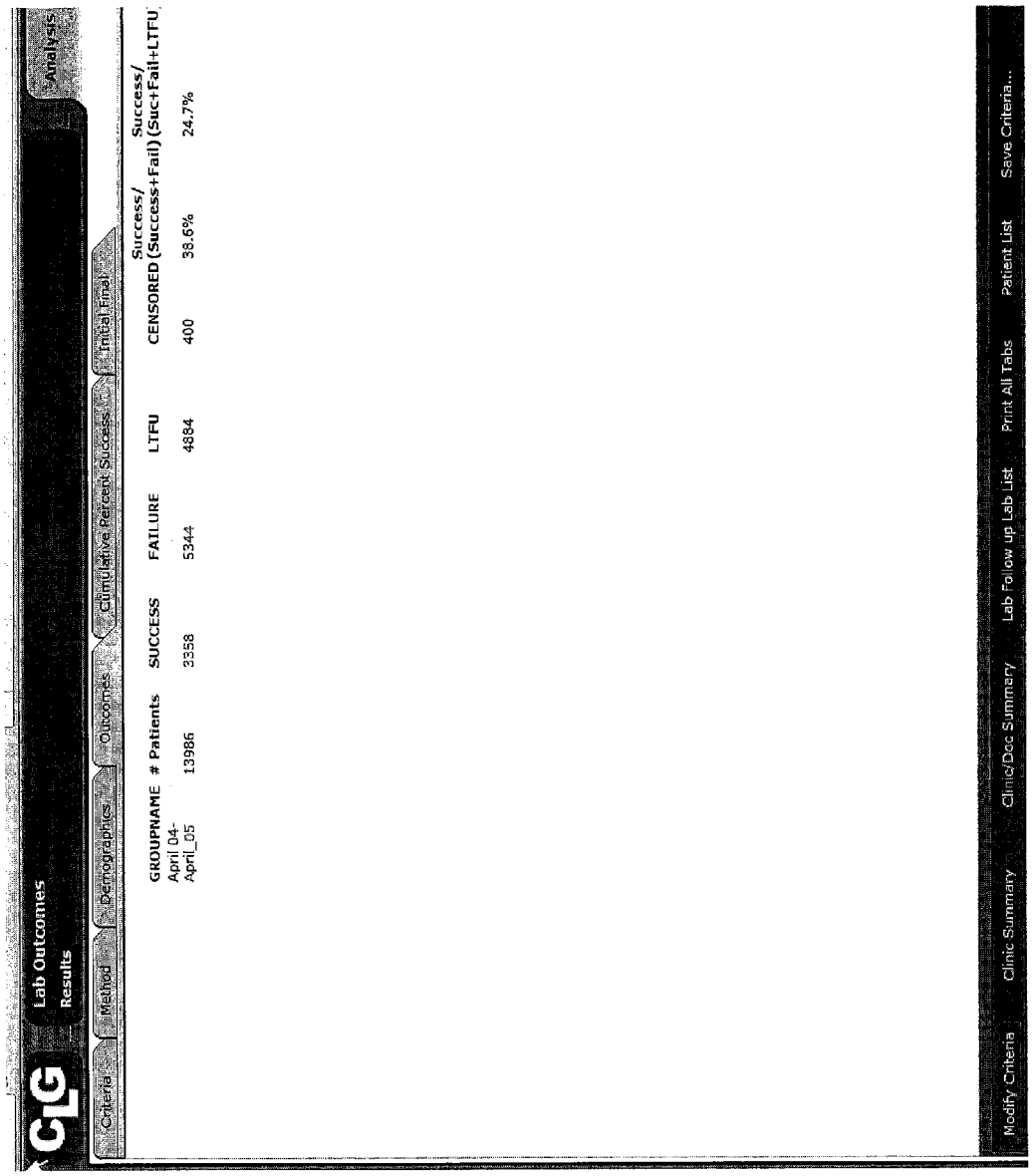

The Results Page for the Lab Outcomes analytic, FIGS. 24 and 25 have some of the same tabs found on the Results Page for LOS (FIGS. 13-18) and Readmission (FIGS. 20-22), but differ in the layout and formatting of the Outcomes screen, and also in the presence of two unique screens, the Cum Pct Success screen and the Initial/Final screen.

The Criteria results for Laboratory Outcomes is depicted in FIG. 24, which shows a summary of the criteria given to the analytic. The Outcomes Results screen is depicted in FIG. 25. The Outcomes Results it displays in numeric form, (not the graphed results of FIGS. 16, 18 and 22), providing summary statistics for the specified cohort, including: number of patients, number of successes, number of failures, number of LTFU (lost to follow up), number of censored (censored can be due to inadequate calendar follow up time or due to a death detected in a match to the social security registry that prevented the patient from being followed to the end of the outcome window), ratio of successes to combination of successes and failures, and ratio of successes to combination of successes, failures, and lost to follow up.

The Laboratory Outcomes Results screen also includes a Reports section containing buttons for the following Reports: Clinic Summary (FIG. 26), Clinic/Doc Summary, Follow-up Report and Patient List. The reports can be provided on a real time basis, monthly, quarterly, etc., to provide an indicator of quality of care, or for example, to warn of deviation of process of care performance from norms or desired targets. It is understood that the reports described herein in reference to the Laboratory Outcomes analytic can be obtained in connection with the other analytics described herein. As mentioned above, such reports, analytics and data are available and preferably are provided on a real time basis.

Figure 26:
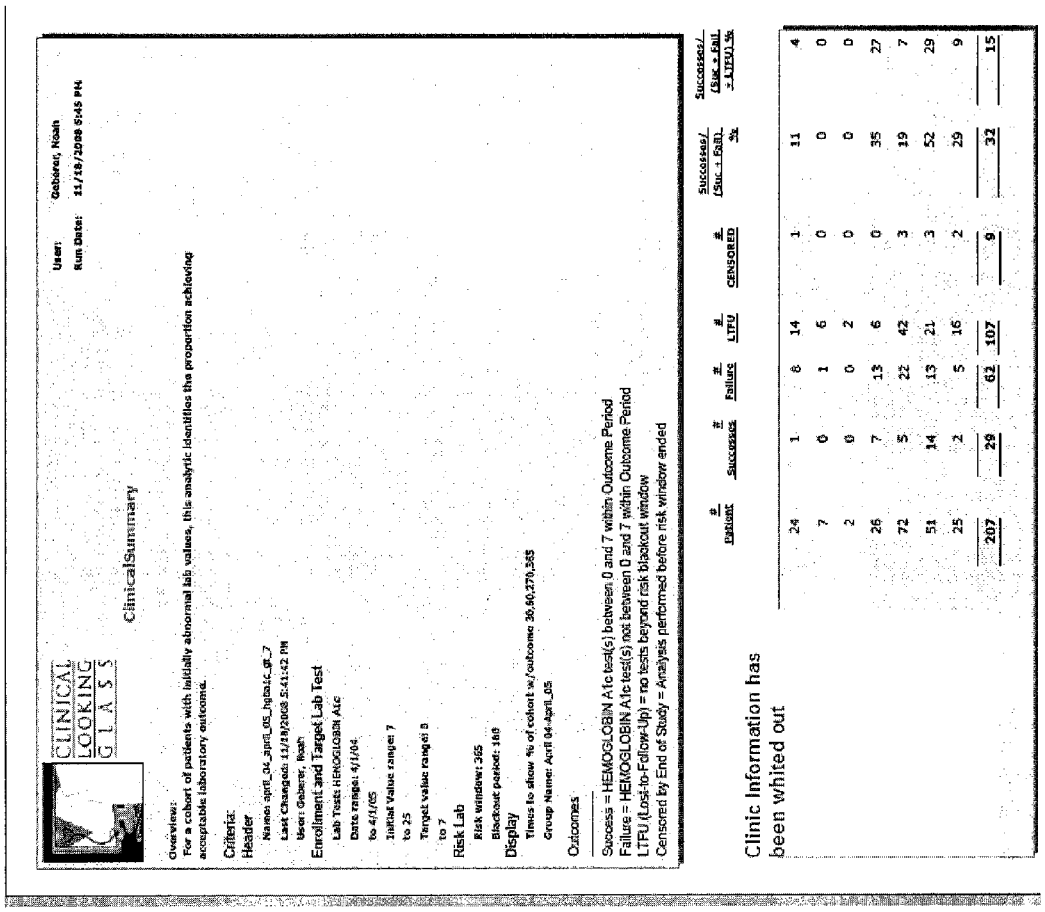

An example of a Clinic Summary Report is depicted in FIG. 26, which shows laboratory outcomes results by specific clinic. The top box area summarizes the criteria entered on the Parameter Entry screen (FIG. 23). The middle box area summarizes outcomes, displaying Success, Failure, LTFU (Lost to Follow-Up), and Censored by End of Study. The bottom section presents outcome details by clinic located within various categories of medical care. For example, on this page of this report, outcomes for the nine clinics grouped under the Ambulatory Care Network are displayed. Statistics for each clinic include: number of patients, number of successes, number of failures, number lost to follow-up, number censored, ratio of successes to combination of successes and failures, ratio of successes to combination of successes, failures, and lost to follow up, or other statistics.

Figure 27:
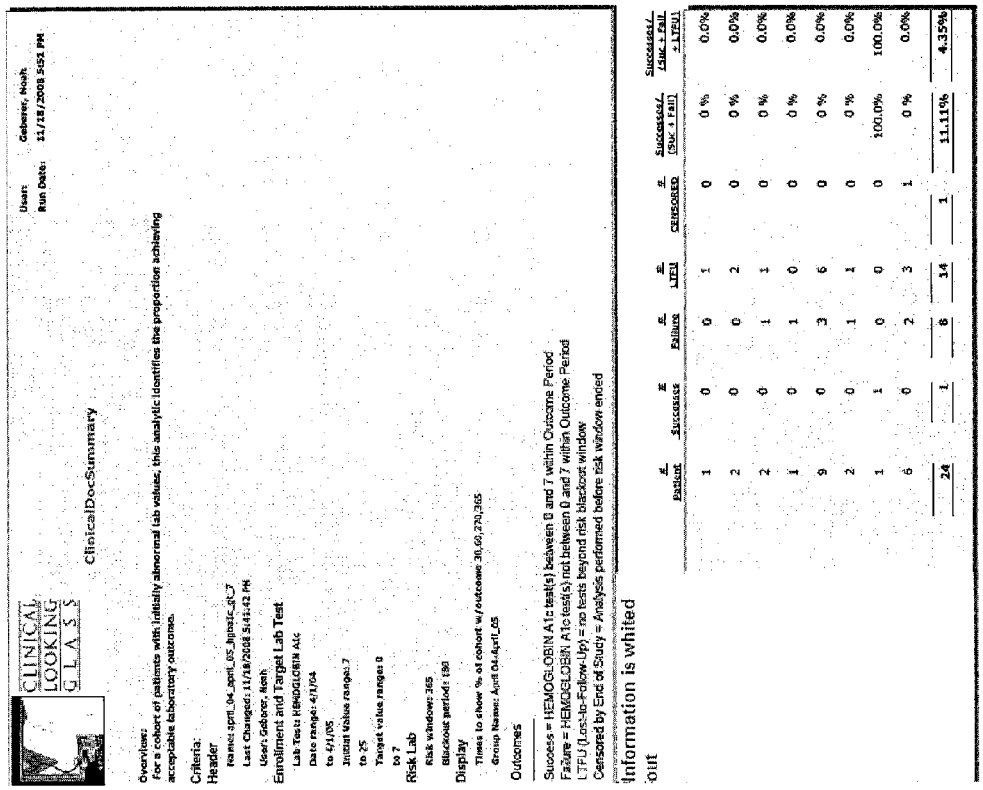

The Clinic/Doc Summary Report depicted in FIG. 27 shows statistics by individual clinic and by individual physician. The statistics shown on the Clinic/Doc Summary Report are substantially the same as the statistics included in the Clinic Summary Report (FIG. 26).

Figure 28:
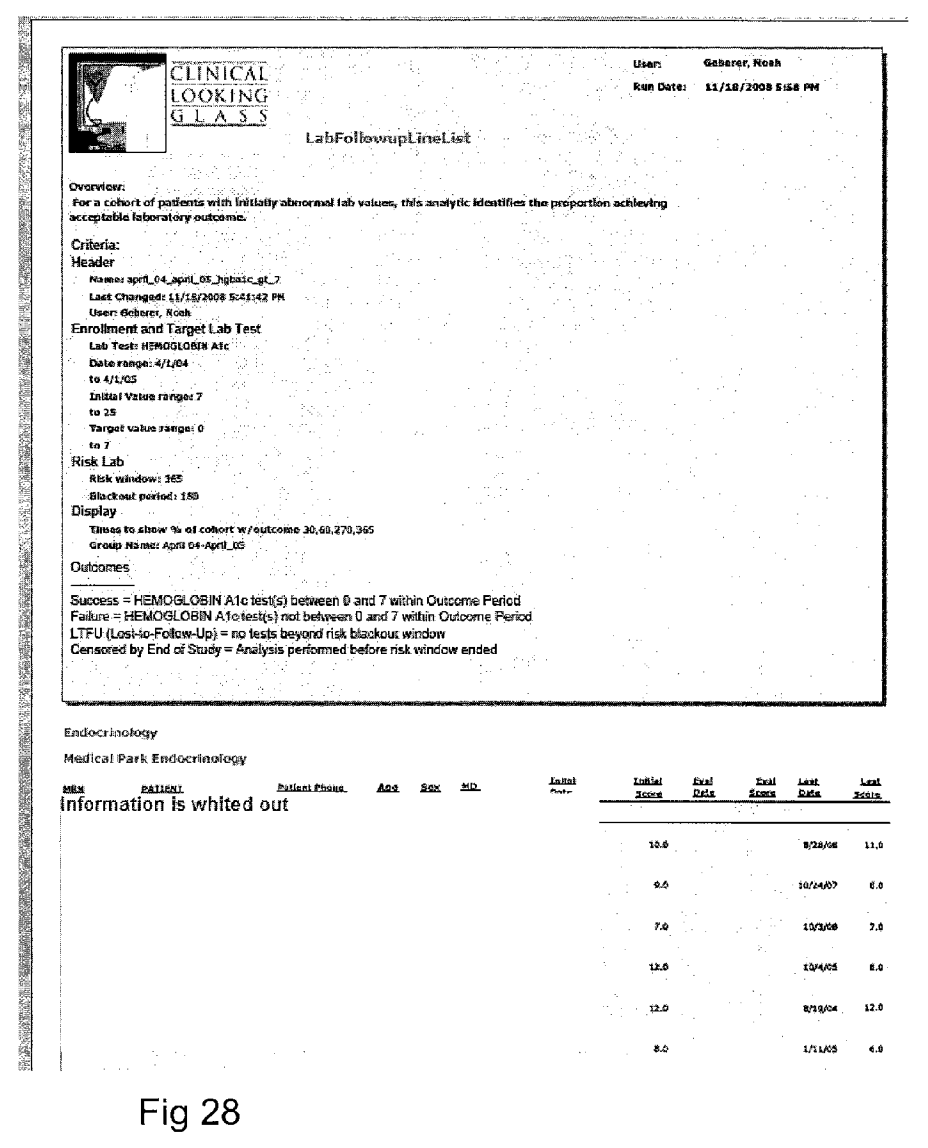

The Follow-Up Report depicted in FIG. 28 provides a remediation report. For each clinic a list of all patients who have failed to reach the desired outcome, or have been lost to follow up (no repeat lab test in the desired outcome window) are shown, including their telephone numbers, physicians, and laboratory detail. The first laboratory value, the evaluated laboratory value for the purpose of determining success or failure, and the most recent laboratory value are provided in the report.

Figure 29:
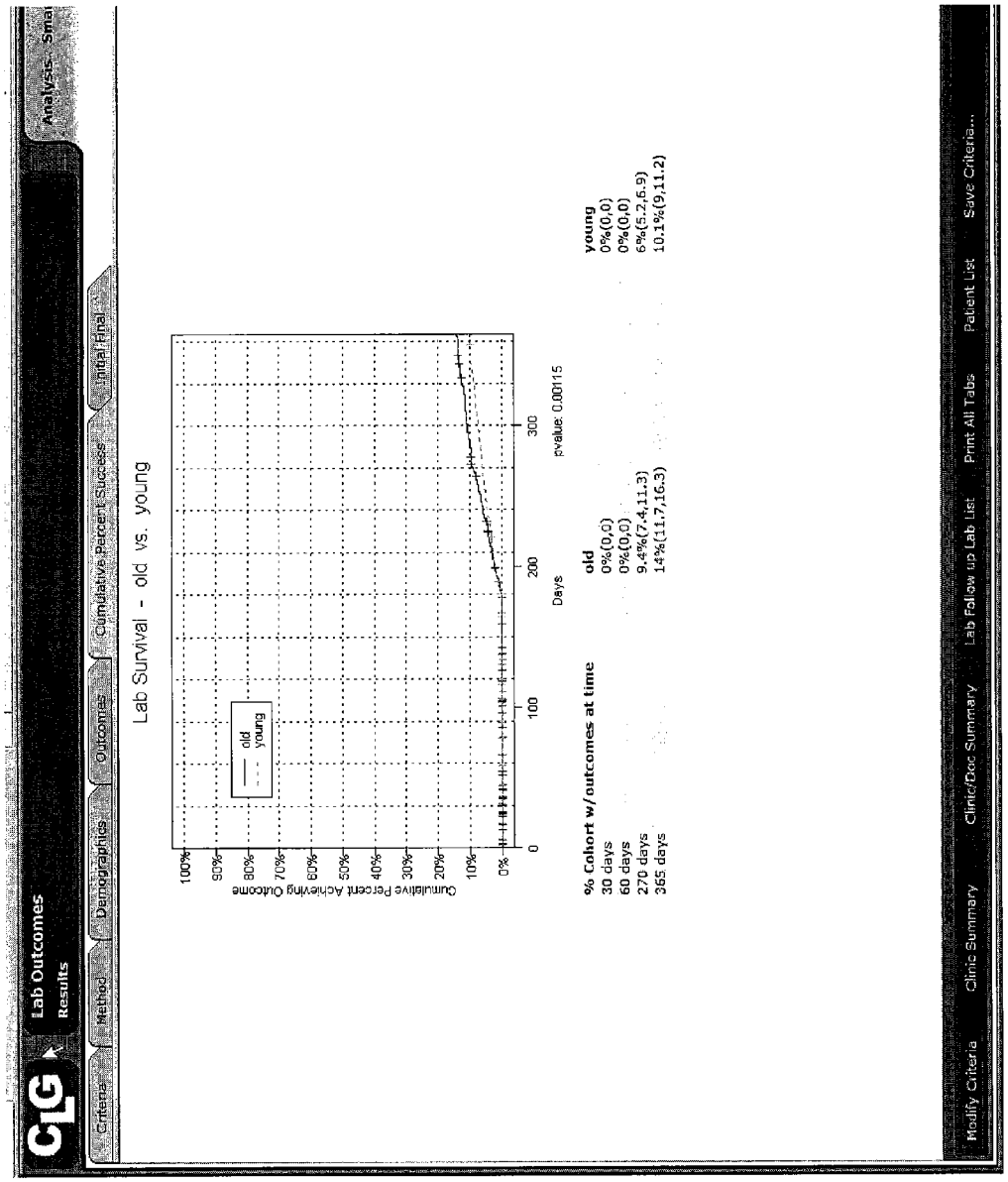

The Cumulative Percent Success Tab depicted in FIG. 29 is obtained by selecting the Cum Pct Success tab on the Results screens shown in FIGS. 24 and 25. The Cumulative Percent Success page displays the cumulative percentage of patients who have achieved the desired outcome. The graph is preferably the complement of the Kaplan-Meier survival curve, which, for example, can handle the challenge of censorship. The first success is considered the outcome of interest. The denominator follow up group changes with time as observation times for the patients become progressively censored.

Note the flat line for the first 180 days. This reflects the blackout period of 180 days that was entered in the Parameter Entry screen (FIG. 23). Below the graph is a table displaying results in quantile format. The table shows percentage of cohort with outcome at the specific time intervals shown.

Figure 30:
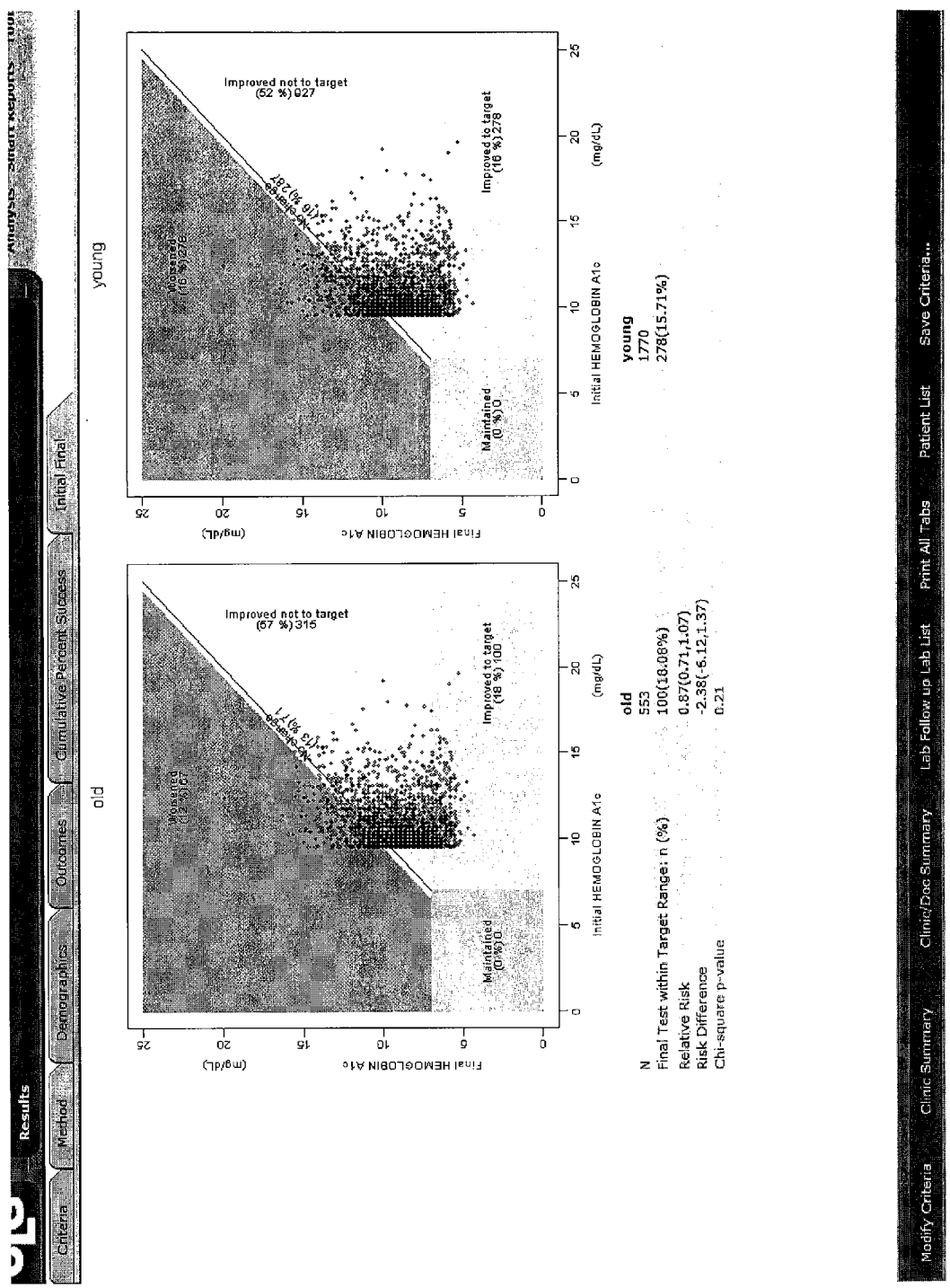

The Initial/Final Tab depicted in FIG. 30 is obtained by selecting the Initial/Final Tab on the Results screens shown in FIGS. 24 and 25. The initial final tab displays every patient for whom there is an initial and evaluated value. Each point represents a patient whose x axis is the initial value and the y-axis is the final value. The horizontal line identifies the upper limit of the target value. The graph in FIG. 30 includes a straight edge coming vertically from the x-axis. This is due to the fact that the parameters entered in the Parameter Entry screen (FIG. 23) included a start range of 9.5, hence the straight edge at 9.5. Patients whose condition has deteriorated are represented in the dark gray zone marked "Worsened" above and to the left of the line of equality (y=x). Patients who have improved but not to target, are represented in the light gray zone marked "Improved Not to Target." below and to the right of the line of equality. Patients who have improved to target end up in the medium gray zone marked "Improved to Target" below the horizontal line and to the right of the line of equality. The relative percent of each group is provided in the appropriate zone. Those patients whose results have not changed significantly stay in the white zone around the line of equality (y=x). Note that no one exists in the medium gray square marked "Maintained". The Maintained zone represents those patients who began in the target zone and remained there. By definition, all patients in this cohort began above the target zone and therefore their point representation cannot exist in the Maintained zone. At the base of this display is the relative risk of clinical success (improved to target) of the old vs. the young population of diabetics as well as the risk difference.

Mortality Analytic

The Mortality Analytic is an extreme endpoint for evaluating outcome and reviewing care of those who die, which is useful in gaining an understanding of results that may be preventable. Generally, the Mortality Analytic determines mortality percentages, time from admission to a hospital until death, time from a live hospital discharge until death, and other indicators, based on particular diagnoses. The Mortality Analytic can also determine mortality percentages independent of the place where the mortal event occurred, e.g., intra or extra hospital. Information related to mortality is obtained both from hospital records for intra hospital deaths and extra hospital deaths by matching patient to social security tapes. The Mortality Analytic is run by selecting the Mortality Analytic from the Main Menu screen (FIG. 4). A Parameter Entry Screen substantially similar to the Parameter Entry Screens herein described in reference to FIGS. 5-6, 12, 19 and 23 is obtained.

Inputting parameters into the Mortality Analytic Parameter Entry Screen is described in connection with an example of determining mortality in patients who have experienced myocardial infarction (MI) during a hospital stay. For example, to compare mortality statistics for anterior wall MI and inferior wall MI for the same time period, a Study Group is selected having an ICD-9 set for Anterior MI and using the drop down menu for the diagnosis menu, primary only is selected. This group can be labeled or named, for example, as Anterior MI. The time range for the Study Group is set to Jan. 1, 2000 in the Start Date field and Dec. 31, 2000 in the End Date field. The Stored Cohort field is set to default or other named cohort. The Utilize Cohort Date indicates the first hospitalization after the date associated with each individual member of the cohort. Additionally, Death status is entered, such as SSA or SSN or for example, in-house deaths. SSN refers to an option to see death statistics for both inside the hospital and post-discharge. Using the SSN option, records can be matched against the Social Security Administration registry. Preferably matches can be further limited to SSN, name and/or date of birth. The interval for the analytic is from a starting point to death, for example, from admission to death. Alternatively, the interval can be live discharge to death, or other interval. The Risk Window, which reflects the range of the final graph is set to a time period, such as 365 or 180 days. The Times to show % of cohort with outcome field indicates the table obtained from the graph indicating percent of the cohort dead for a particular measure, such as days, e.g., 30, 60, 270, 365, which will create a table indicating the percent of the cohort that died at 30, 60, 270, and 365 days respectively. Confidence intervals are also provided. Additional parameter fields include age, gender, facility, service care center, IPA status, and line of business.

To obtain a comparison of the Anterior MI parameters discussed above to Inferior MI, similar parameters to the parameters entered for the Anterior MI Study Group is input in the Parameter Entry Screen in the fields of the Comparison Group. The ICD-9 set, however, should be set to Inferior MI, rather than Anterior MI which was entered for the Study Group. It is understood that other ICD-9 sets can also be set to compare to the Anterior MI Study Group. The analysis is run by selecting the Run Analysis button, or other equivalent button on the Parameter Entry screen.

Figure 31:
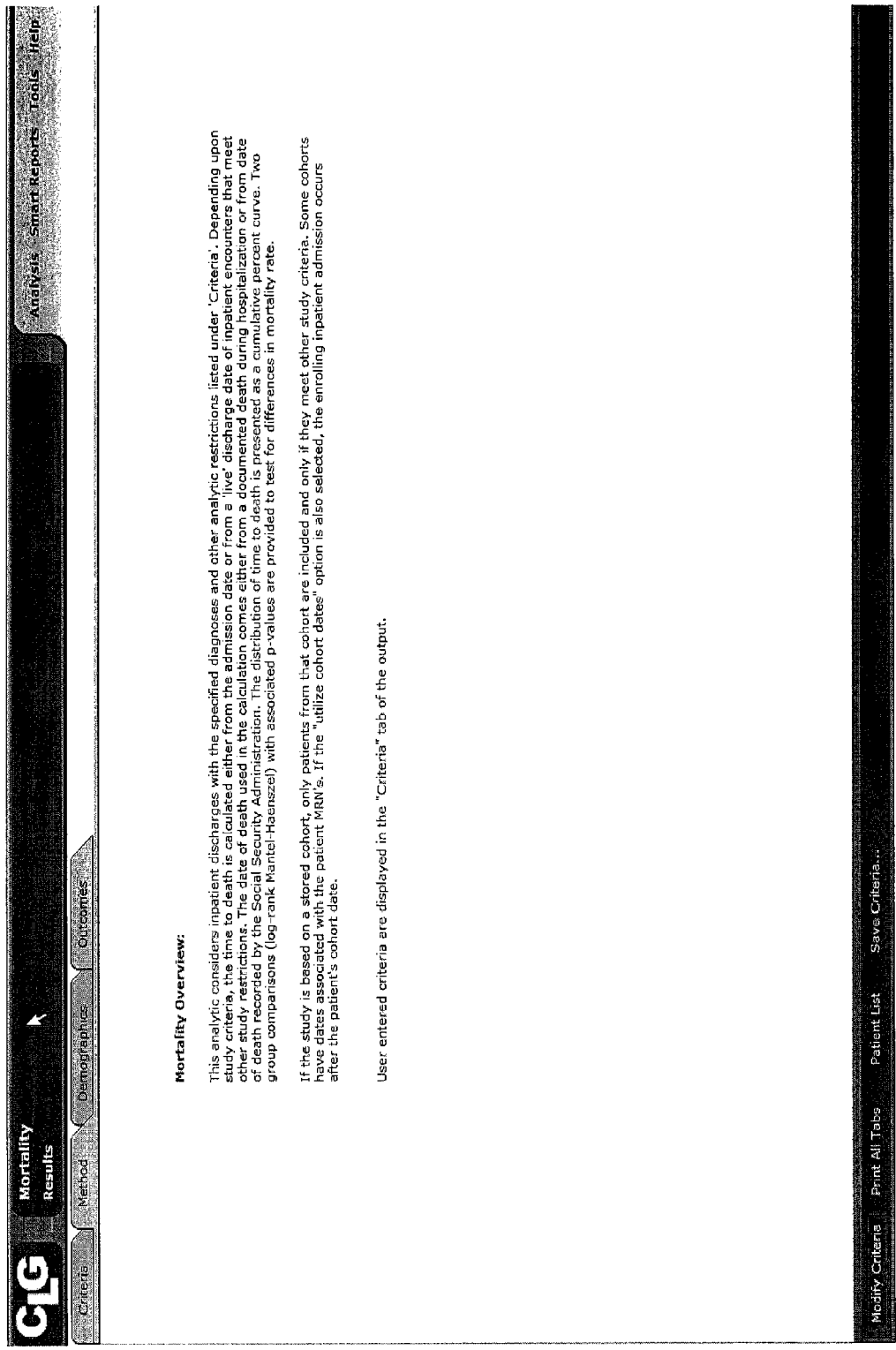

The Mortality Results screens are depicted in FIGS. 31-34, which include views and corresponding tabs, such as: Methods, Criteria, Demographics, and Outcomes. The Methods Results screen shown in FIG. 31 provides a description of the analysis undertaken in the Mortality Analytic. The Criteria Results Screen depicted in FIG. 32 provides a criteria summary of the information or parameters entered on the Parameter Entry Screen. In addition, the Criteria Results Screen can include additional information related to the Analytic, such as the sensitivity of the social security match to the people known to have died, or a confidence interval.

As shown in FIG. 32, in this example, Anterior MI and Inferior MI in hospital deaths were detected by the social security match 60.9% and 78.3% of the time respectively. The confidence intervals are wide (38.54%, 80.29%) and (56.3%, 92.54%) respectively. This wide confidence interval is due, for example, to the small number of in hospital deaths that could be detected. In most analyses, sensitivities and confidence intervals can be in a higher or lower range.

Figure 33:
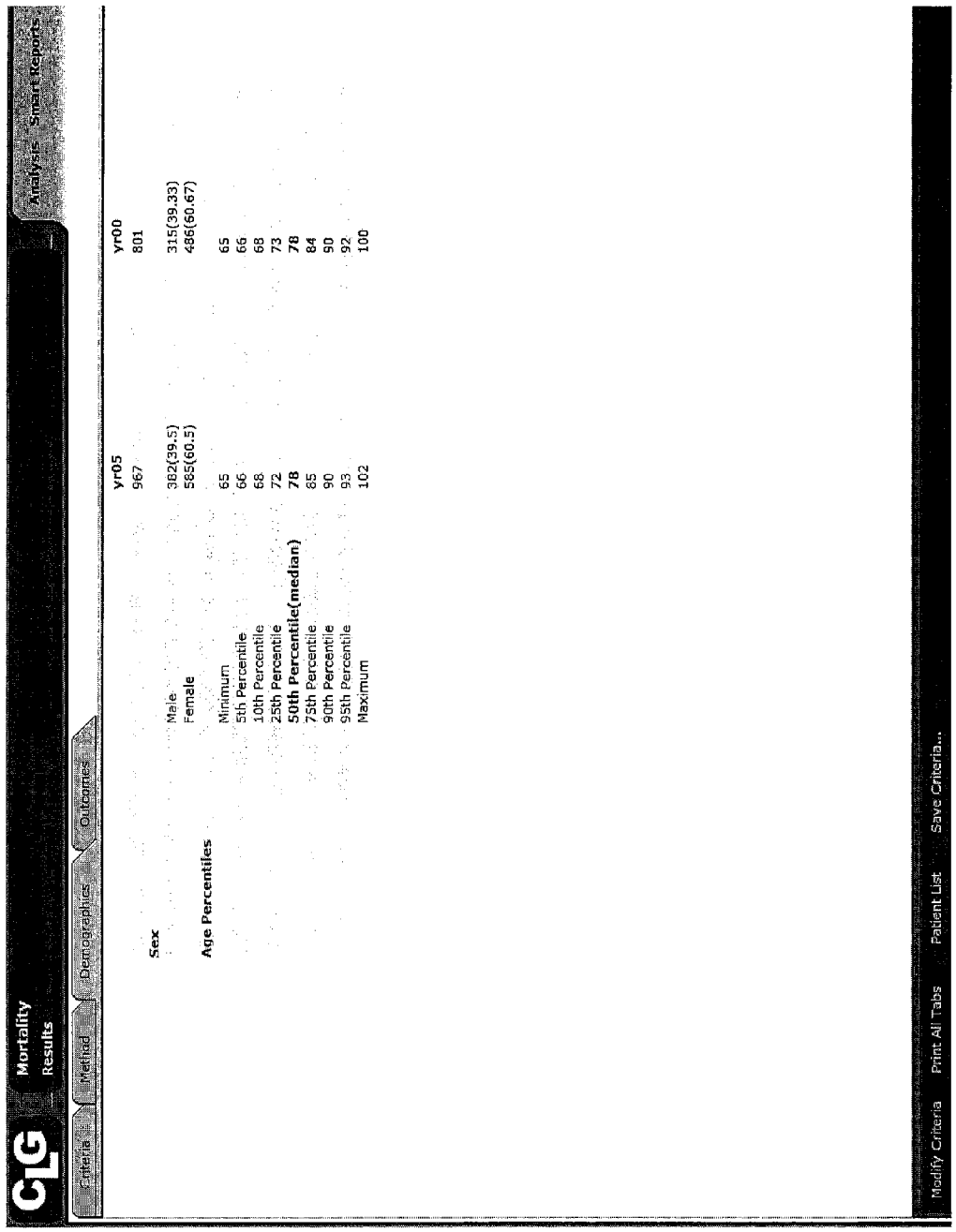

The Demographics Result Screen depicted in FIG. 33 shows, for example, the makeup of the cohort in tabular form by age in percentiles, showing a total number of patients in the resulting cohort at the top of the screen, or other demographic information. The patient list can be selected to obtain a comprehensive list of all patients who-make up the resulting cohort. This information is displayed in a spreadsheet and includes information, such as the following: time to death, died in house, died during any hospitalization not just the index hospitalization, censored, age, gender, account number, MRN, name, date of birth, race, admitting date, discharge date, and date of death. Preferably the patient identifiers are accessible only to authorized personnel.

Figure 34:
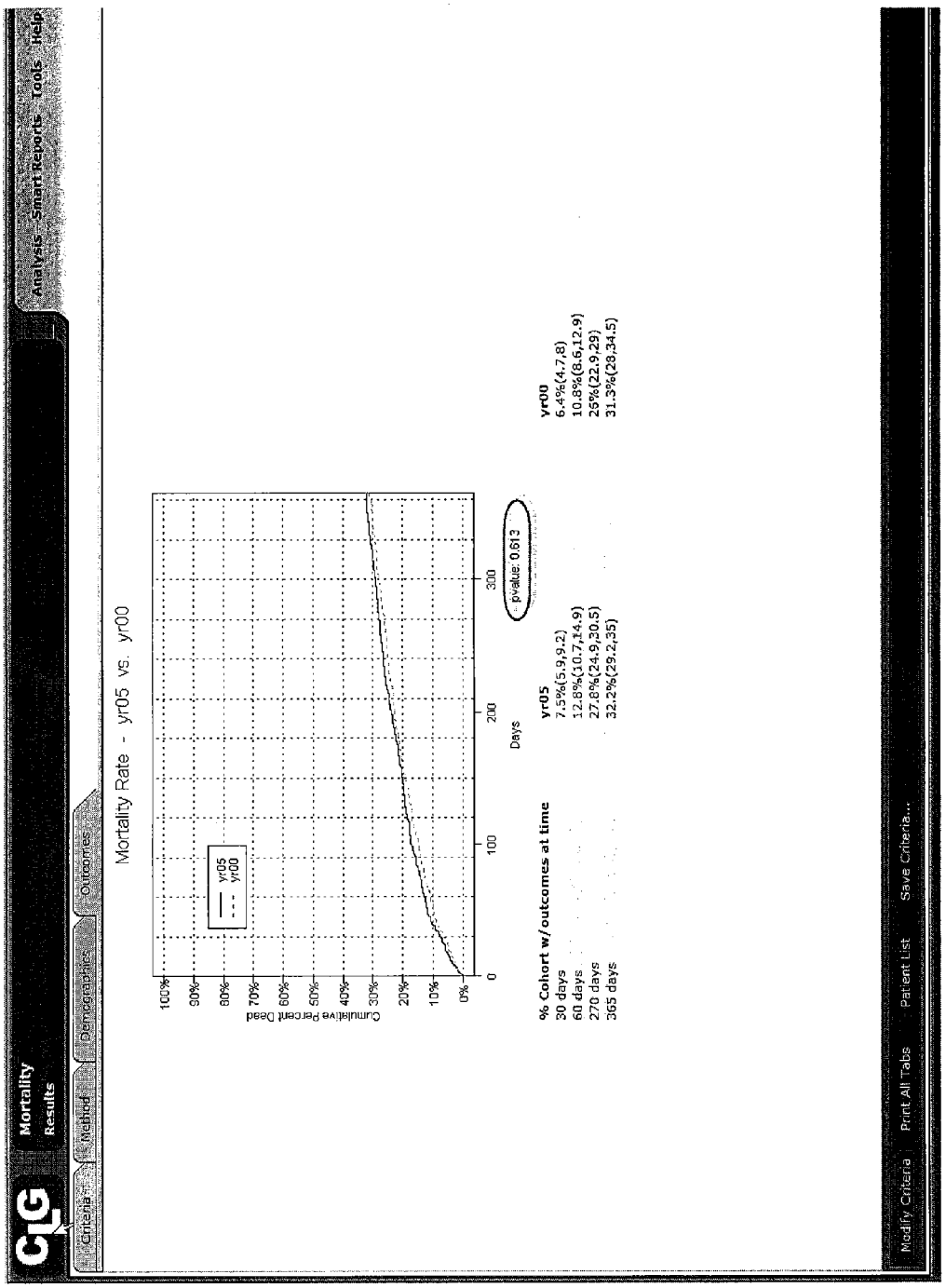

The Outcomes Result Screen depicted in FIG. 34, shows, for example, the results in graphical format. The x-axis, as shown, records the amount of time that has elapsed. The y-axis records the cumulative percent of the cohort that have died by the time specified on the x-axis. It is understood that the data represented by the x and y-axes may indicate other data relevant to the Mortality Analytic. Additionally, a p-value, is provided, which establishes the significance of the difference in cumulative percent dead in the two cohorts. As shown in FIG. 34 a table is provided with the graphed data including the cumulative percent of patients who have died by the times specified. Also shown on FIG. 34 are buttons, e.g., New Criteria, which when selected takes a user to the Parameter Entry Screen to enter new criteria, Home, which when selected takes a user to the main menu (FIG. 4), Print, which when selected prints all of the content in the Results screens.

Quality Duration Calculator

The Quality Duration Calculator ("QDC") measures the quality of patient care by evaluating the time period for a patient to achieve and maintain a certain condition, such as certain laboratory values. For example, after a deep venous thrombosis a patient should be anticoagulated (or within a specific range of INR) for six months. For patients with HIV infections, the patient should have zero viral loads forever. The QDC allows a user to assess a clinic's quality of outcome achieved by identifying patients with a therapeutic need and then calculating the number of days for the patient to achieve target lab values divided by total number of days in follow up. Clinics or other health providers can be compared, for example, by the percent of time they kept their patients in good or desired ranges.

In general, patients are not tested on a daily basis. Therefore, the lab value of a patient on a specific day must be interpolated between lab values. The QDC interpolates the patient's lab values, for example, using an algorithm, creating intermediate data points to note clinically significant changes. The clinically significant changes can be defined by the user. Occasionally, there is no lab value for a particular period. In this case, a missing data point, or other point is used. Ranges of lab values are assigned categories, such as bad, fair, good, or excellent, to simplify the comparison between the clinics or health providers. These categories are generally created using the utility Quality Duration Set Builder.

Figure 48:
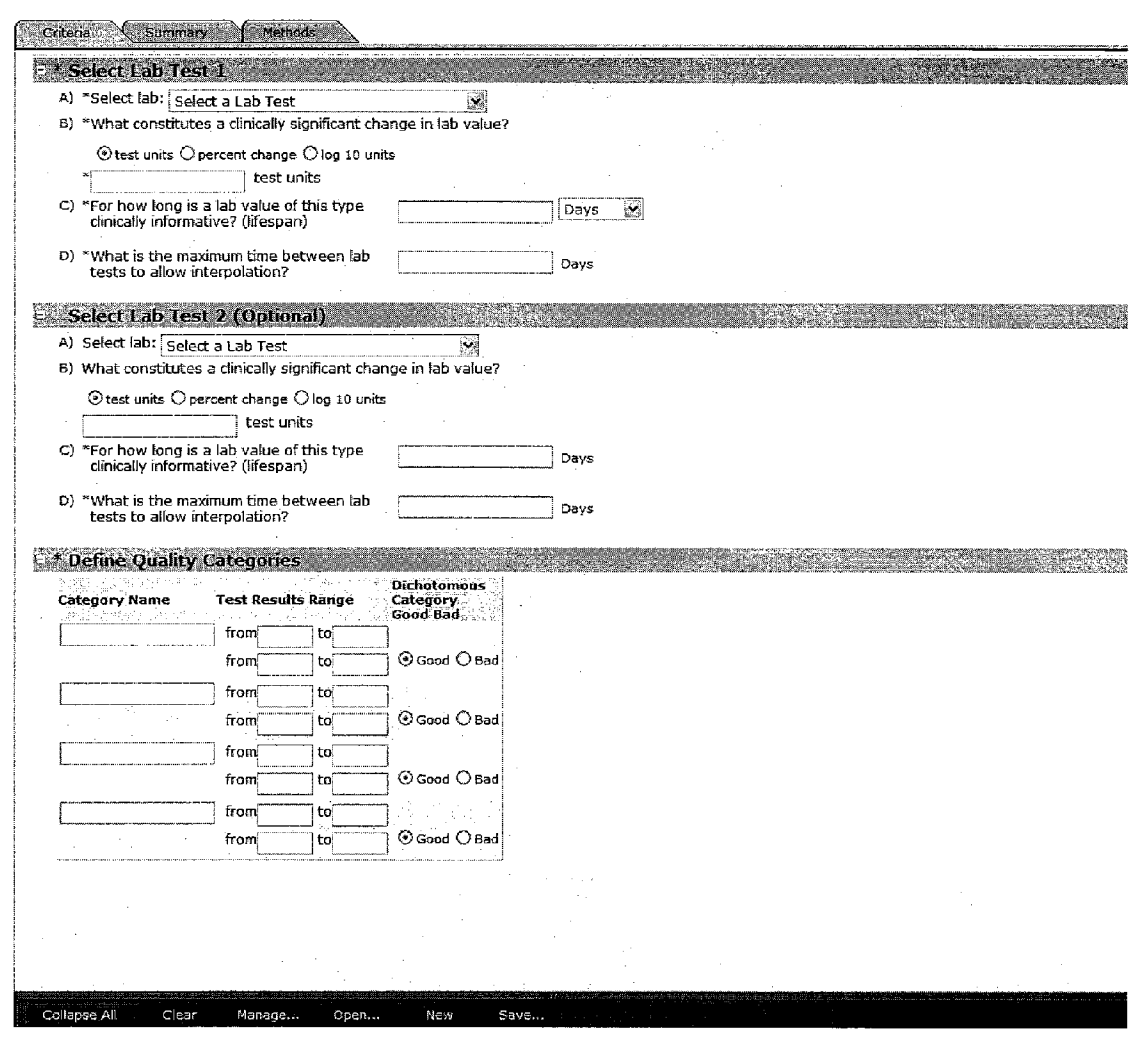

An embodiment of the Quality Duration Set Builder parameter entry screen is depicted in FIG. 48. The Quality Duration Set builder allows the user to define the lab tests of interest, the change in lab value that is considered clinically significant (e.g., given on an absolute scale, relative scale, or log(base 10) scale), the duration that a lab test will be carried forward as the patient's daily lab value should there not be a subsequent laboratory value available for analysis, how to categorize the range of values expected and further how to dichotomize these in categories ranging from bad to great. Generally, the set is named and then saved, and is then available to be used in the Quality Duration Calculator, or in other analytics, and shared with other users or colleagues. In the example shown in FIG. 48, the set is named "viral load" and considers changes of 1.5 on the log scale as significant, and specific ranges of lab values are assigned to categories.

Figure 49:
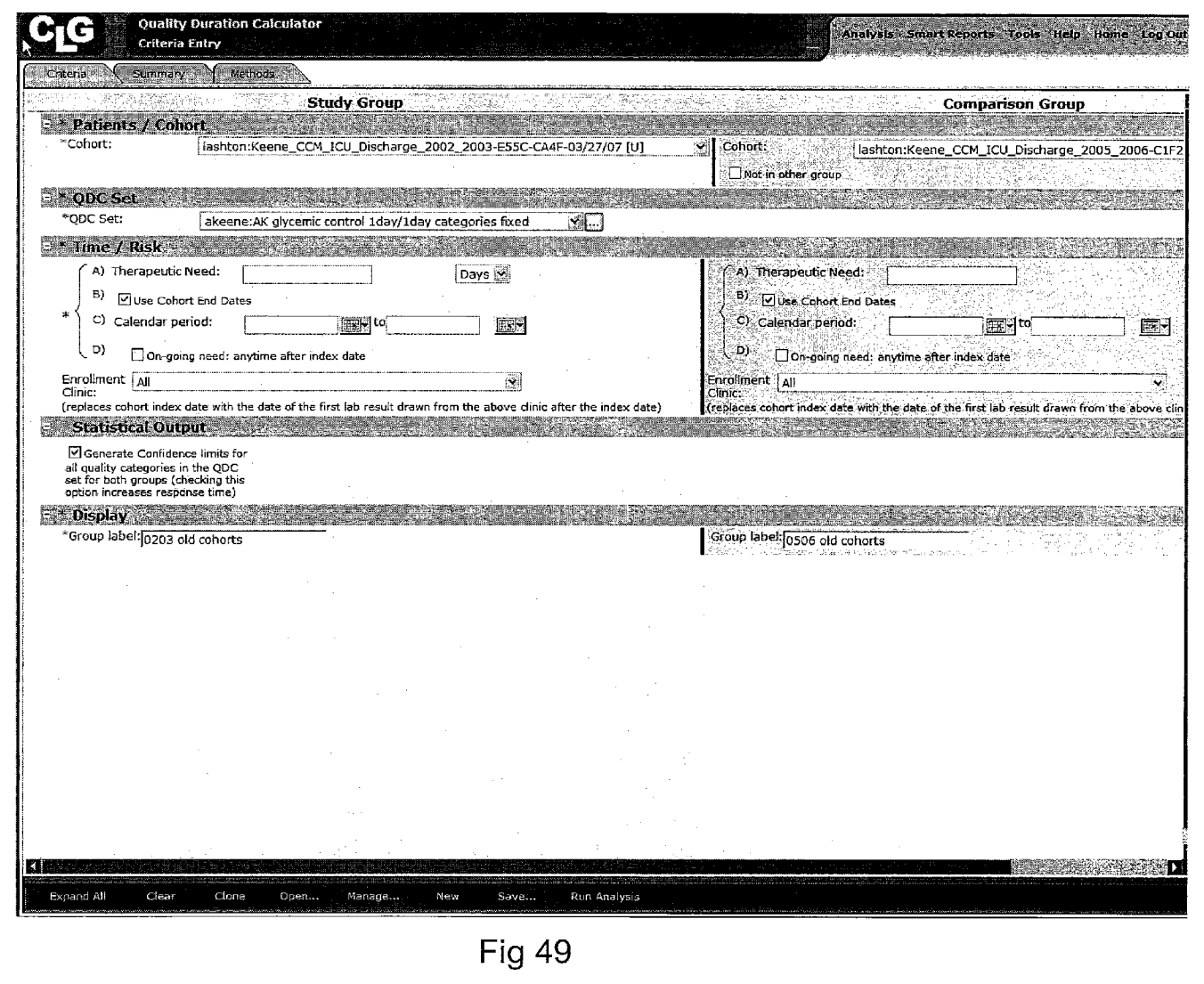

Referring to FIG. 49, which depicts an embodiment of a parameter entry screen for the QDC, the QDC evaluates the period for which there is therapeutic need to achieve a specific lab value. A user may enter the amount of time following the index date during which the patient is expected to need therapy. If the duration is lifelong the ongoing option is chosen. Additionally, the evaluation can be restricted to a Calendar Period of interest. For example, when a clinic has initiated a new health services intervention, the analysis can be restricted to that period during which the intervention was implemented. As a result, a patient's laboratory values could only testify to the quality of care for the period of time in which the patient had a therapeutic need and the Calendar Period of interest. In some instances, a user may only want to follow the outcome of the patient from the time the patient was first seen in a particular clinic regardless of which clinics were subsequently visited by the patient.

Figure 51:
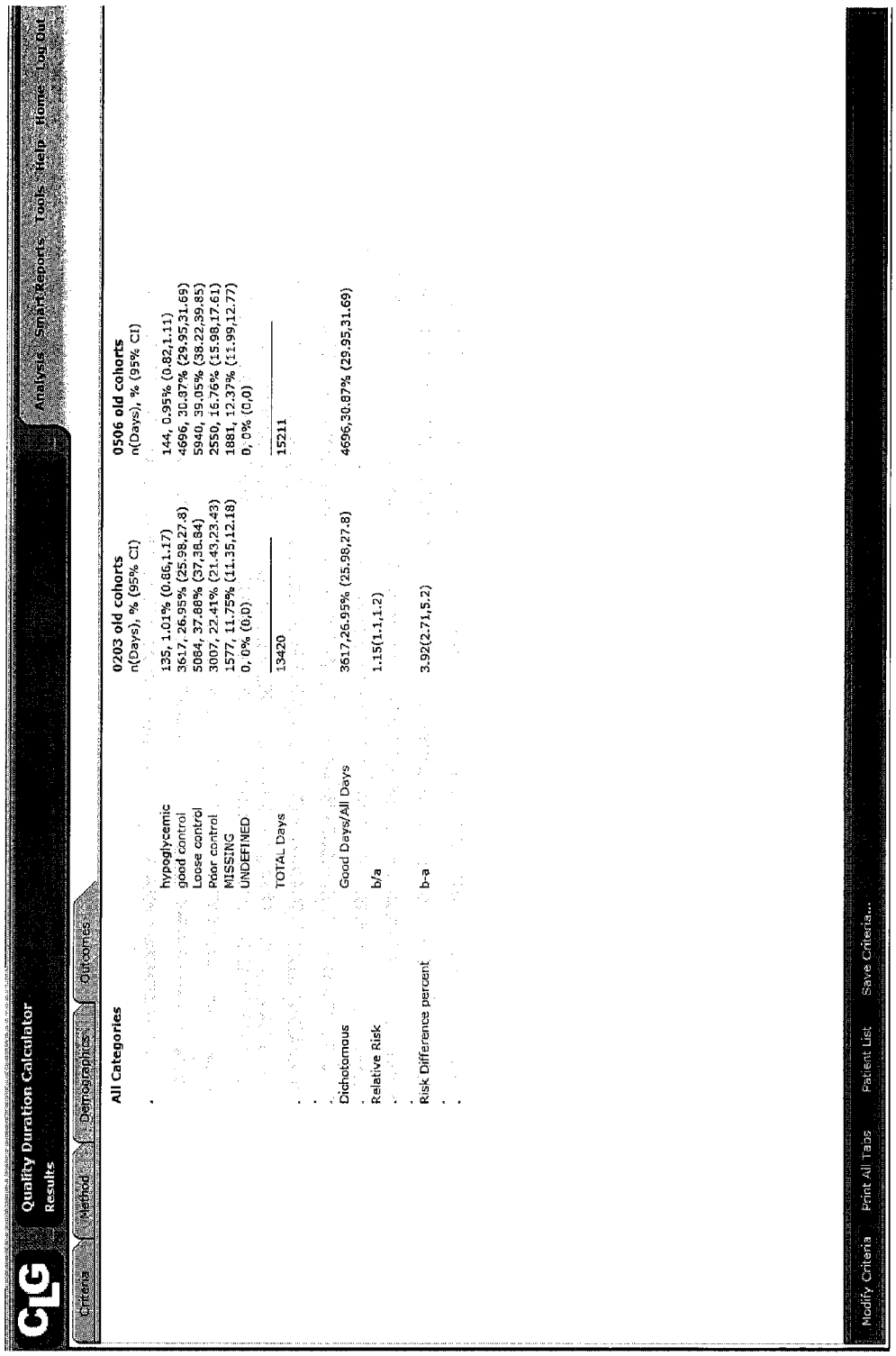

The Cohort field allows a user to select a cohort from cohort builder to study, e.g., the cohort defined in a quality duration set in FIG. 48. The QDC will use the index date as the date when therapeutic need was initially established. The QDC Set field allows input related to information for deciding how and when to interpolate laboratory findings as well as how to categorize the laboratory outcomes. The Not in other group field eliminates in the second group patients (medical record numbers) seen in the first group to allow the creation of exclusive categories. The Therapeutic Need field defines the duration of time after the index date during which the patient is required to achieve target laboratory outcomes. If ongoing, is checked off, the patient is deemed to require vigilance on this laboratory outcome. The Calendar Period field restricts the accumulation of observation-days to days that fall within the Calendar Period. This is a useful tool for comparing health services intervention that began and ended at a specific time. Only those patients with therapeutic need during the calendar period will contribute time to the assessment of quality outcome. The Enrollment Clinic field restricts the accumulation of quality days to those days that follow the first visit to a clinic defined in the enrollment clinic category. The Generate Confidence Limits all categories check box allows a user to obtain confidence limits for the study groups. When the data is entered into the screen of FIG. 49, the analytic is run, and a results screen is obtained, such as the results screen depicted in FIGS. 50-51 are obtained.

Figure 50:
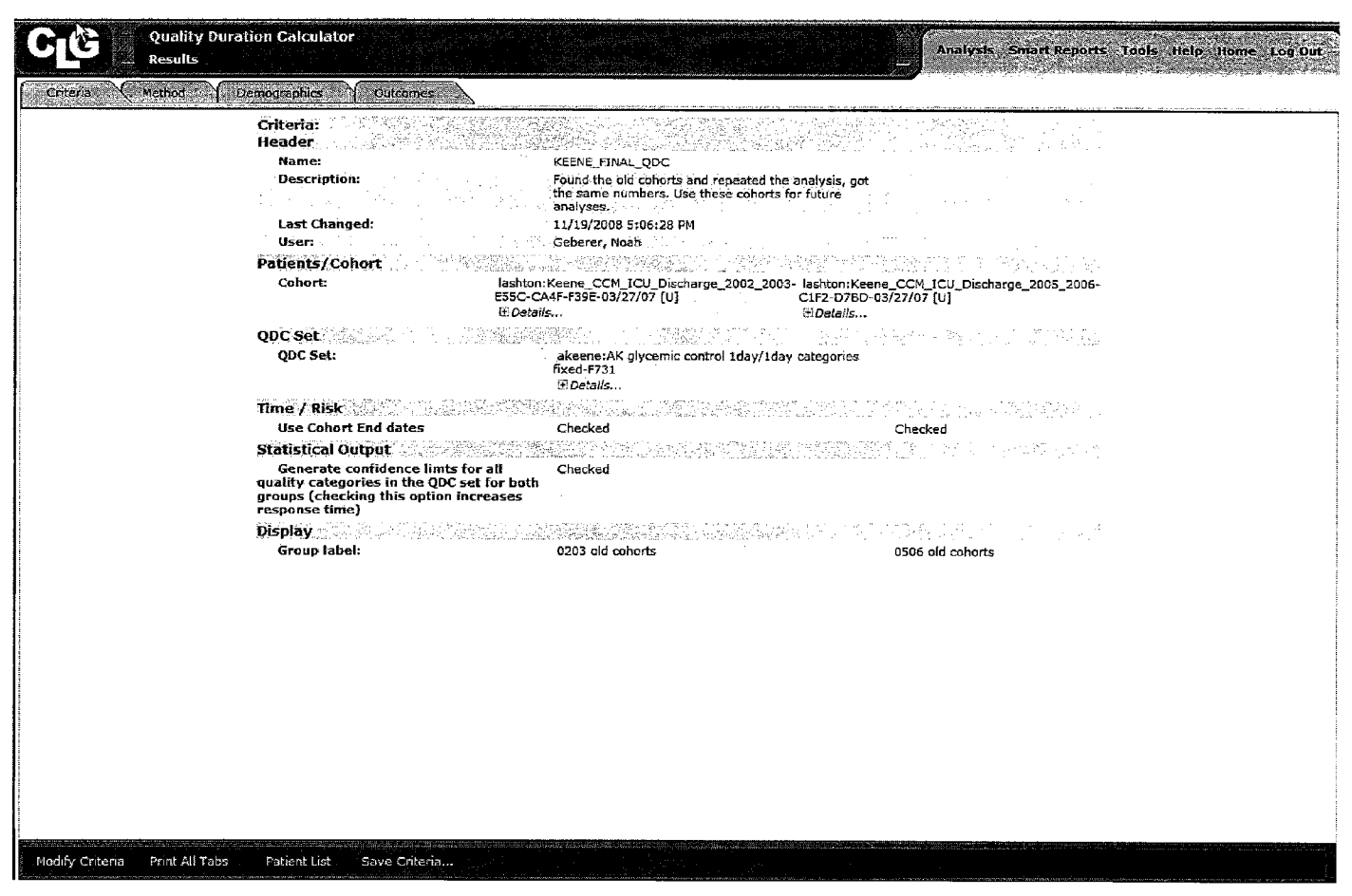

The QDC criteria results screen is depicted in FIG. 50, and indicates criteria used in the analytic, such as the criteria entered at the parameter entry screen of FIG. 49. The outcomes results of FIG. 51 provides the days that all patients spent in each quality category, summed and reported for the entire cohort. Using the total days assessed for the cohort as a denominator, a percentage is calculated for each category. When confidence limits are requested, these are obtained using bootstrap methods where each cohort data set is randomly resampled with replacement 1000 times to generate a distribution of percentages by category. The range of percentages that capture the middle 95% of values is considered the confidence limits for the sample estimate.

To simplify a two-group comparison, each category is analyzed as either 'good' or 'bad', thereby creating only two categories for two groups. Confidence limits for the percent of days in the 'good' category are calculated. The ratio of these percentages gives a relative risk. If this ratio is 1, the groups have the same percent time spent in good care indicating no difference between groups. A statistically significant difference between groups is manifest when the 95% confidence interval on the ratio or percentages (RR) does not include the value 1. Similarly, using the risk difference model, if the percent time spent in the good category is the same in both groups, the percent difference would be 0. If the 95% confidence interval includes 0, then there is no evidence of difference between the two groups.

Emergency Room (ER) Patient Flow

The ER Patient Flow analytic provides, for example, a summary of interval times for emergency room visits, which can be used to compare efficiency of operations between hospitals or within the same hospital for different time periods. The interval times can be used, for example, to measure efficiency in processing patients. Additionally, the analytic can be used as a patient list identifier to find patients seen in the Emergency department with specific diagnoses for chart review of process of care quality, ultimate outcomes, and satisfaction follow up studies. The time interval can be tracked and displayed to, for example, track timeliness of consultants, procedures or completion of required tasks.

Figure 35:
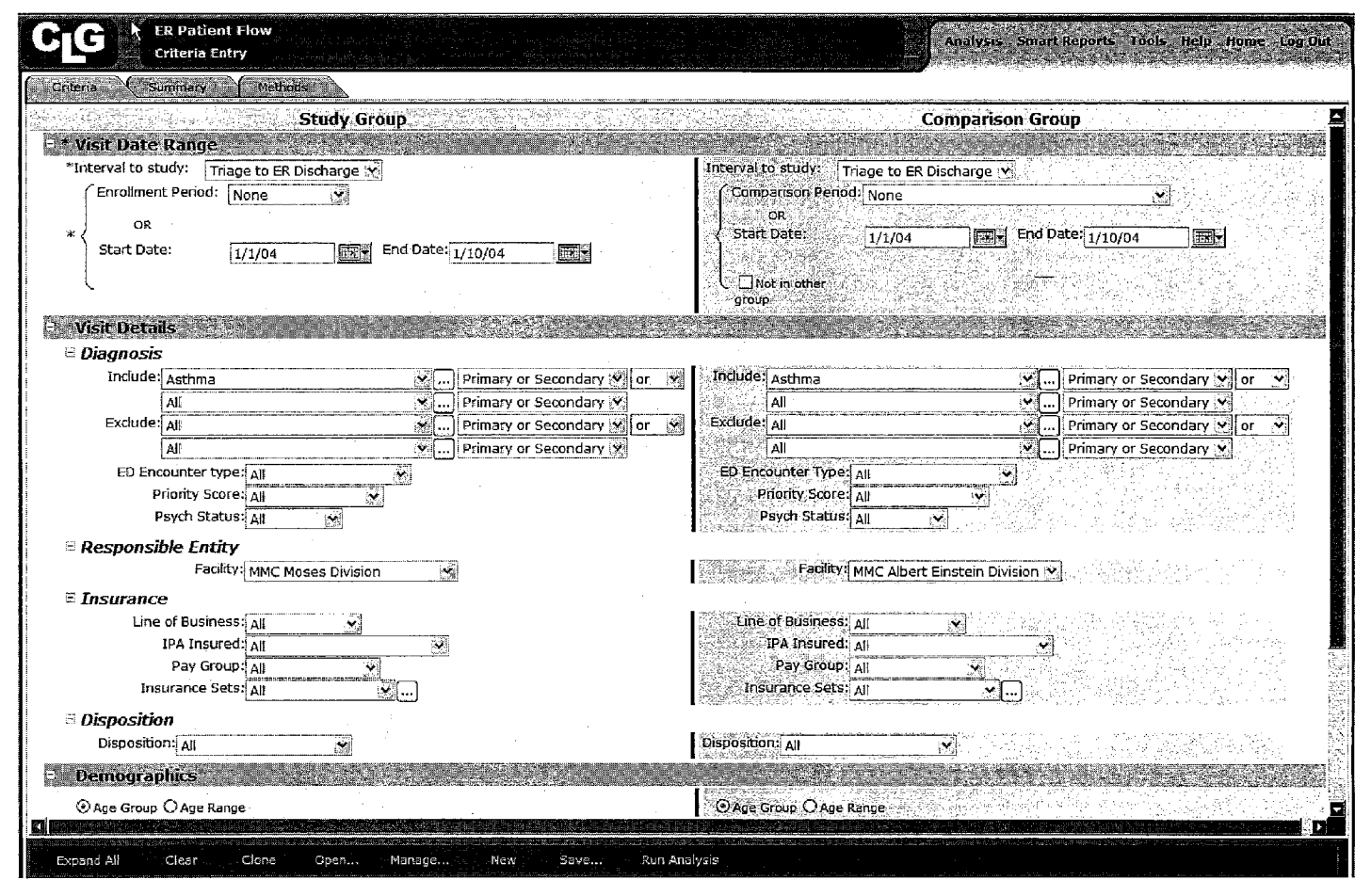

The ER Patient Flow Parameter Entry Screen is depicted in FIG. 35, and is substantially similar to the Parameter Entry Screens discussed herein, (FIGS. 5-6, 12, 19 and 23). ER Patient Flow specific parameter fields in its Parameter Entry Screen include for example, a Group 1 (such as a Study Group) and a Group 2 (such as a Comparison Group).

Additionally, an Interval field is provided in which to enter information related to the interval in which the patient is considered to be in ER, e.g., Triage to ER Discharge or Triage to Treatment. A disposition parameter is entered using a drop down menu, including options such as: all patients or select patients, such as patients seen in the emergency room who were ultimately admitted to the hospital during this emergency room visit, patients discharged to the street or to their home, or patients seen in the emergency room who were ultimately discharged to a nursing home. An Enrollment Period parameter is entered to identify the time period during which a patient was discharged from the Emergency Department, e.g., past several hours, past day, or past week. A Psychiatric Status parameter is entered to select a cohort for this analytic based on the patient being psychiatric, non-psychiatric, or patients in either category. An Emergency Department Priority Score parameter is entered to select patients to include in the analytic based on degree of acuity, e.g., low, intermediate, high, or all patients. When the parameters have been entered to the Parameter Entry Screen, the Analytic is run by selecting the Run Analysis button to obtain the Results.

Figure 37:
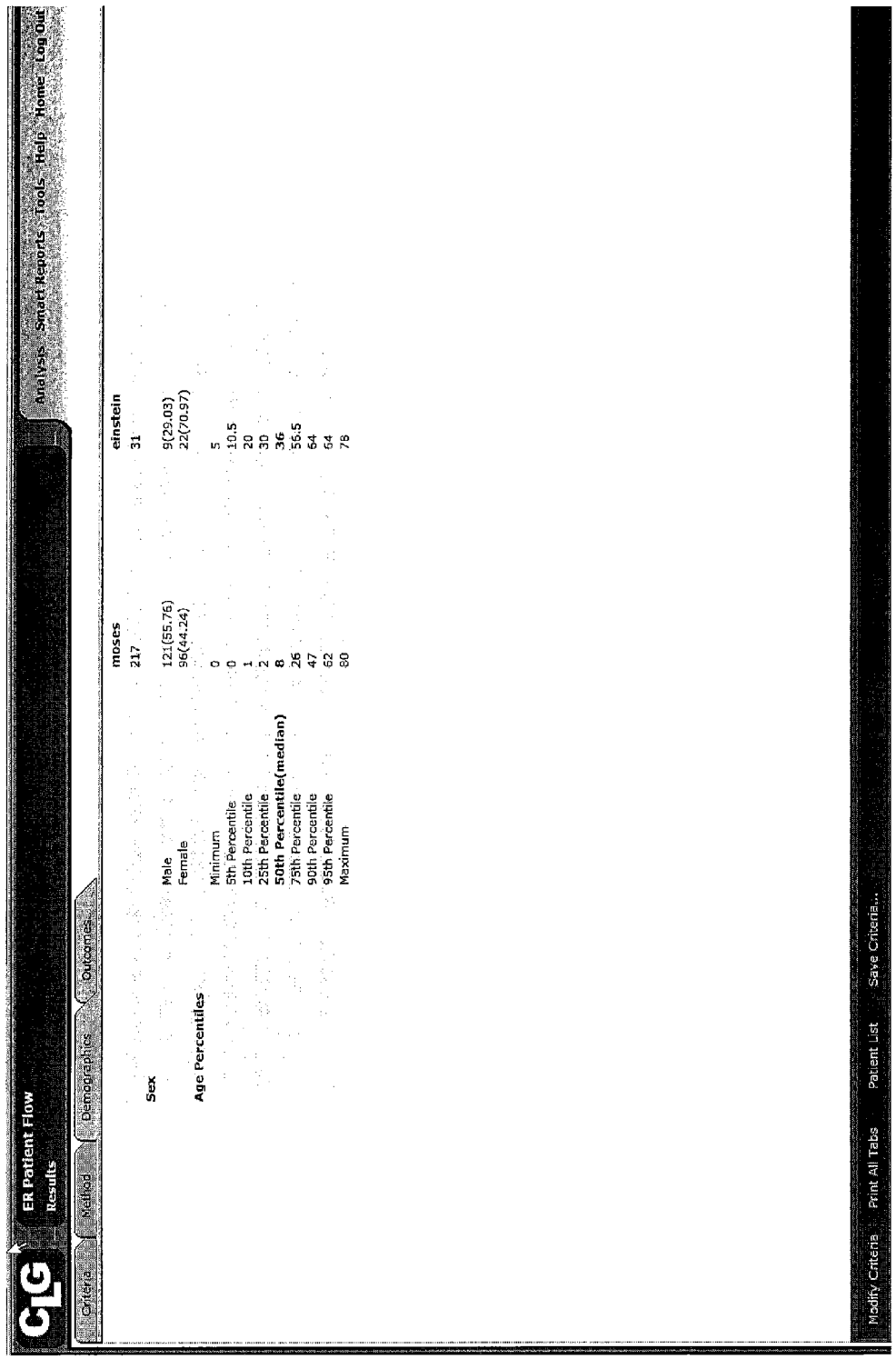
Figure 38:
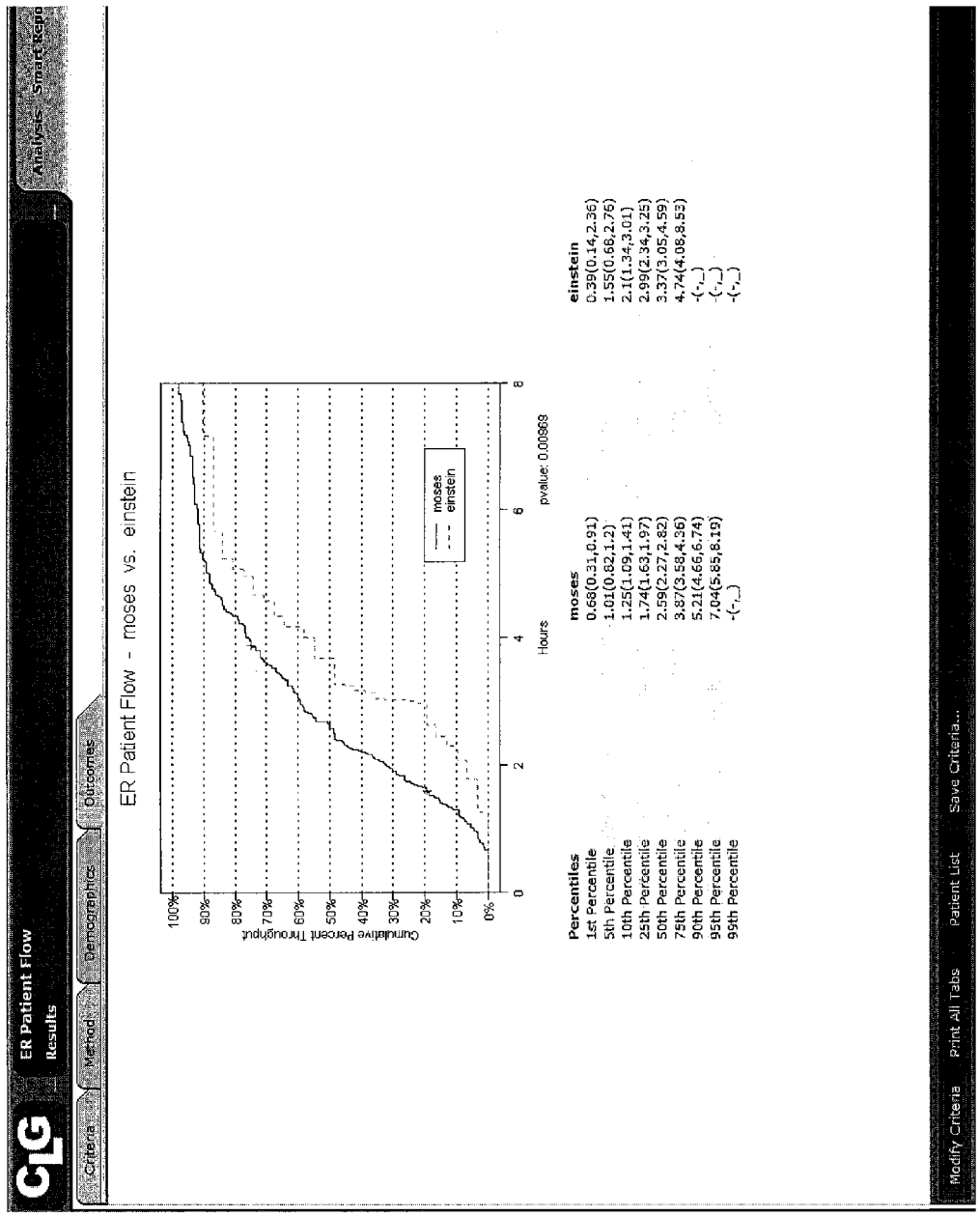

The Results Screens are provided in FIGS. 36-38, each of the Results Screens includes Analytic results and buttons for revising the parameters of the Analytic, e.g., a new criteria button, print and return to main menu pages. The Methods results typically provide information related to the method of the Analytic. Criteria results depicted in FIG. 36 provide a summary of the parameters entered in the Parameter Entry Screen (FIG. 35). Demographics results depicted in FIG. 37 provides demographics information related to the patients included in the Analytic, such as number of patients, gender, age, and other information. Additionally, the patient list can be obtained in a spreadsheet. The Outcomes Results screen depicted in FIG. 38 includes the results of the analytic, for example, cumulative percent discharged is presented on the y-axis with the time in hours for the corresponding time represented as hours on the x-axis. The statistical significance of the difference is given as a p-value below the graph on the right. The data obtained and shown in the graph is included in table shown on FIG. 38.

Cohort Builder

Referring again to FIG. 4, which depicts the main menu, from which a user can select a group of patients sharing similar characteristics and create a cohort. A cohort is generally a group of patients, or other individuals. The cohort can be monitored to obtain information relating to outcomes, e.g., proportion achieving an outcome or time to achieve an outcome. The cohort builder associates information with a list of patients, e.g., patient identifiers, such as MRN or a date for each patient, e.g., the time at which a patient is qualified to become a member of a cohort. Graphic and statistical comparisons between cohorts can be obtained, permitting the drawing of inferences about relative care quality, or identifying those patients who have failed, allowing the user to target remediation efforts to those failing patients (targeted remediation). A cohort can also be used with the analytics described herein, e.g., Time to event, further described herein, to calculate outcome trajectory analyses. Examples of outcome trajectories include: readmission, emergency department visit, clinic visit, achieving a specific lab value, or other outcome. The cohort builder analytic includes several types of qualifications, such as simple time invariant qualifiers, such as date of birth, gender or race, simple time varying qualifier, such as age, whose variation is proportionate to elapsed calendar time, complex qualifiers with several events temporally related in a defined manner, such as health conditions, or other relevant qualifications.

By assembling a cohort of patients and using the Time to Event analytic, further described herein, or other analytics, the system can obtain information related to quality of care, e.g., how well this particular clinic the managed patients (cohort) in their care to achieve specific outcomes, such as laboratory endpoints, hospitalization endpoints, emergency department visit endpoints, and mortality endpoints.

Figure 39:
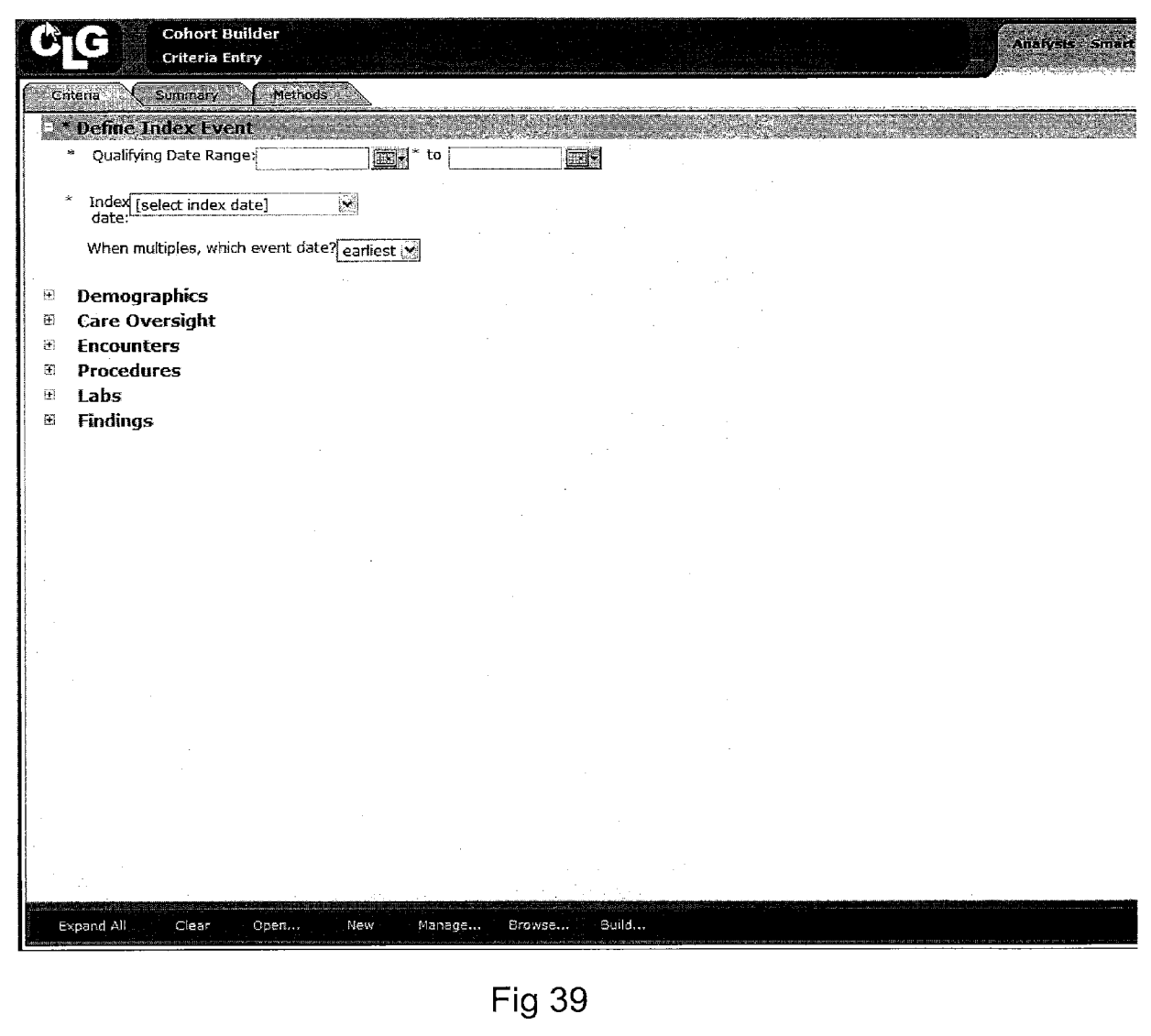

Referring to FIG. 39, which depicts a screen for entering information related to a cohort in the Cohort Builder. Each tab Main, Demographics, Encounter and Result refers to a screen which allows for data entry. In the Main screen, a new cohort can be created. Alternatively, a cohort can be uploaded, by selecting the Upload Cohort button and submitting information related to patient MRN and date. To create a new cohort, a Cohort Name is assigned to the cohort, such as mmg4diabetics9.5, or other name. The Enrollment Date Range information is entered, which is related to the time a patient was associated with a hospital or treatment. The Index Date is the date at which the quality of the outcome is assessed, e.g., a date where the patient's analysis begins. In general, the Index Date is centered on an event, such as inpatient admission or discharge, emergency department triage, clinic visit, particular lab test, or other event. Preferably, the Index Date is within the Enrollment Date Range. Text related to the cohort can be entered in a field titled Description.

The cohort can be saved and run to create the cohort to associate each patient's MRN and index or other relevant date. Each time the cohort is saved, the criteria entered for the cohort is re-run to obtain cohort members who meet the criteria at the time of the analysis. A browse function is obtained by selecting the Browse button, which generates a spreadsheet with a line listing of all the members of the cohort, their MRN, name, index date, date of birth, age, sex, race, ethnicity. This information is preferably security controlled and only available to those whose HIPAA credentials for this feature have been approved by the system operator.

The cohort builder can be used with the analytics further described herein. For example, the cohort builder can be used to share a cohort with other users.

Figure 40:
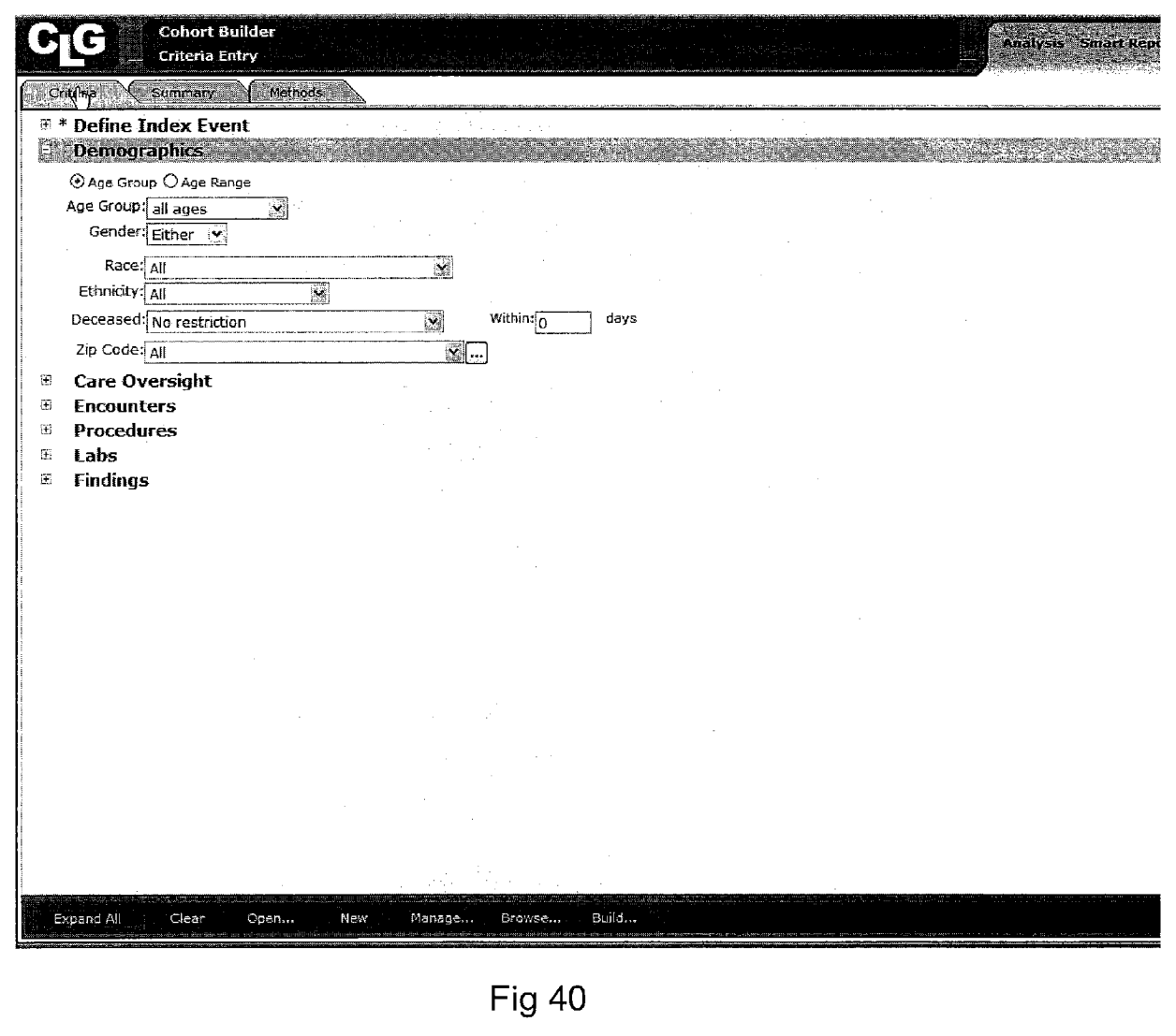

Referring to FIG. 40, a Demographics screen for the Cohort Builder can be obtained by selecting the Demographics tab on the Main screen (FIG. 39). The cohort created, e.g., on the Main screen of FIG. 39, can include demographic specific criteria, e.g., gender, age, race, ethnicity, death status, zip code. Criteria related to a deceased individual can include, for example, in house death deaths, extra hospital deaths, etc., or other place of death, and further specified or expanded by occurring within a certain number of days. In some cases, death information is obtained by matching patient's social security numbers to a national list of social security recorded deaths.

Figure 41:
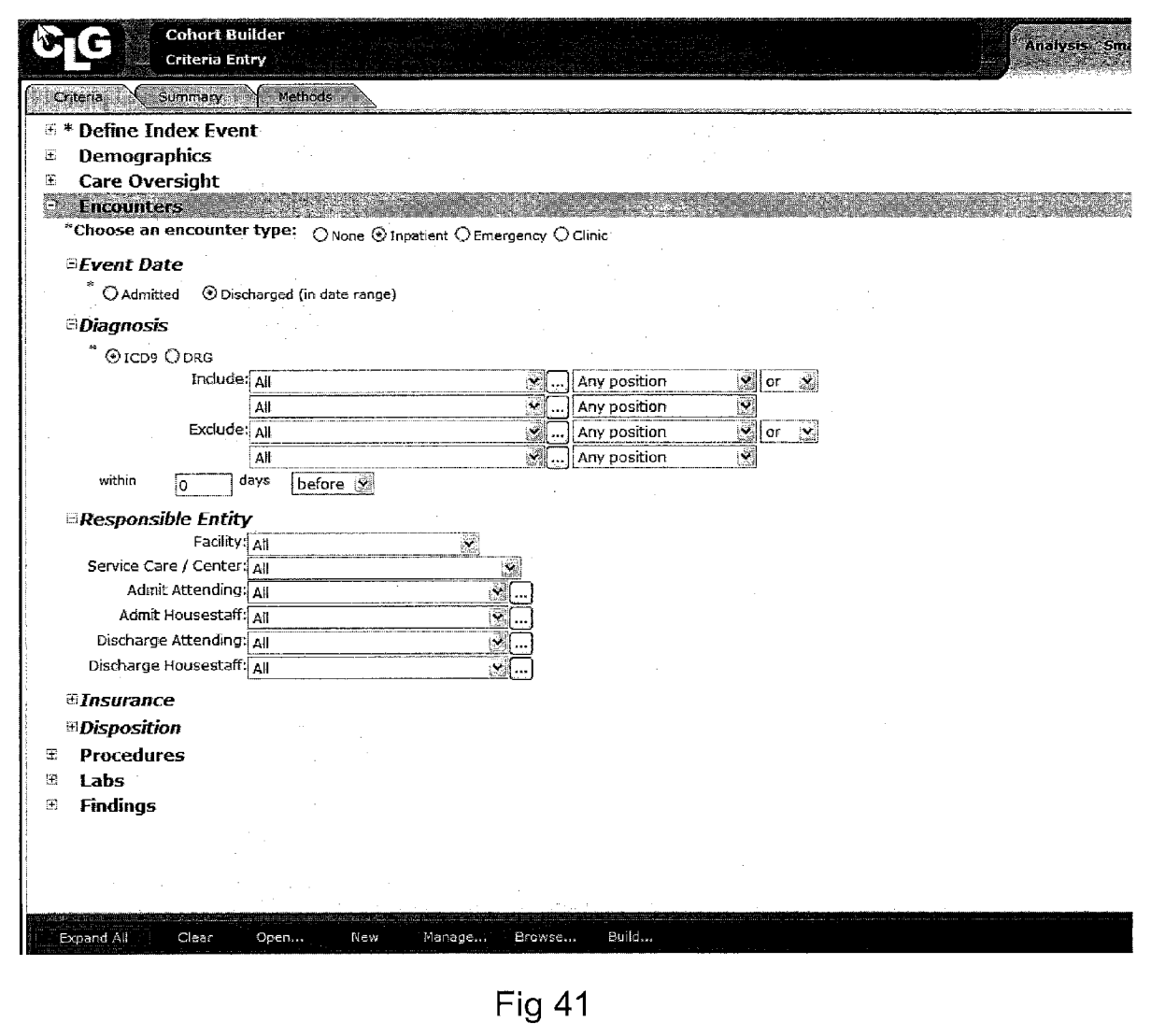

Referring to FIG. 41, which depicts an encounters screen that can be obtained by selecting the Encounters tab on the Main screen (FIG. 39), includes additional criteria for the cohort. The Encounter screen allows a user to add criteria related to the cohort and an activity, such as a hospital admission or discharge in association with a particular ICD-9 or DRG, an emergency department visit, clinic visit, or other activity. The Encounter Screen typically includes a General Section which permits specification of ICD-9 code. Additionally, information related to insurance line of business, for example, commercial, Medicaid, Medicare or all is added. The cohort can also include criteria as to whether the patient is an IPA insurance member. The Within field defines the relationship of the event in the main screen (FIG. 39), e.g., admission, laboratory test or other event, to the encounter in this screen, preferably measured in days. Additional criteria can also be entered related to inpatient discharges and admissions, emergency department activity, clinic activity or other activity.

Figure 42:
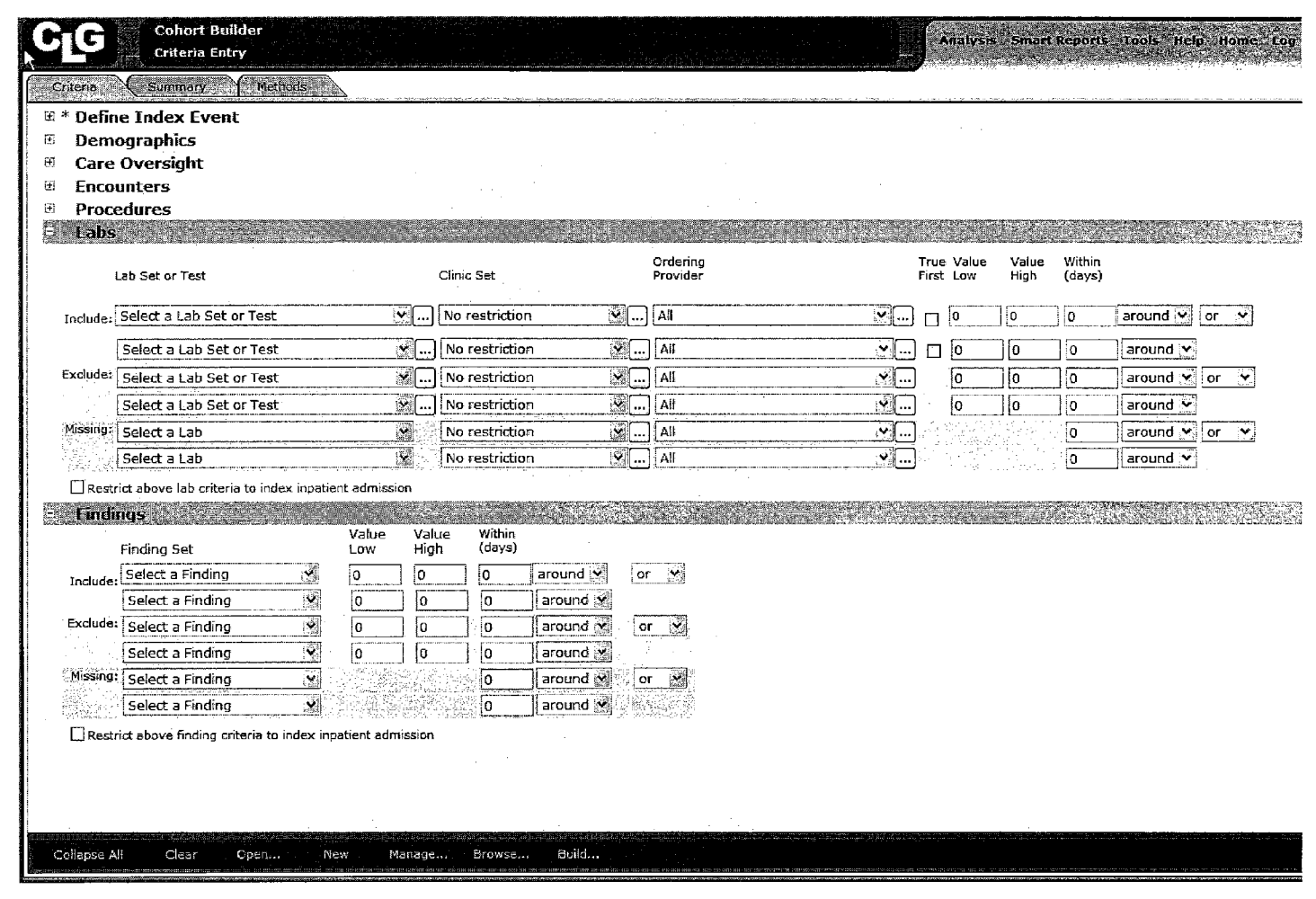
Figure 54:
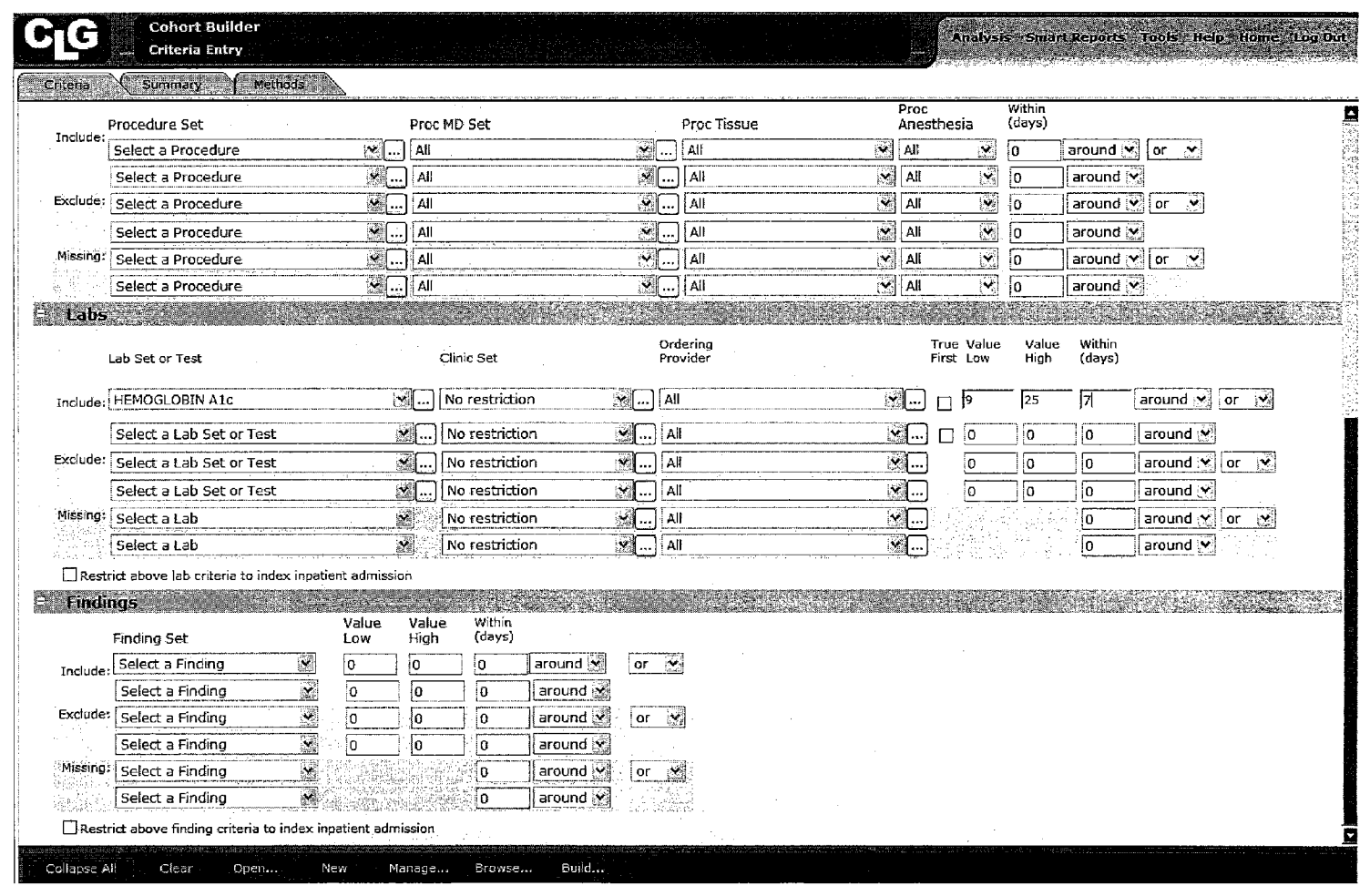

Referring to FIG. 42, a Results screen can be obtained by selecting the results tab from the main screen (FIG. 39). In the example shown in the screen of FIG. 42, a specific value range for HbA1c is selected ranging between 9.5 and 25 and will ignore any HbA1c lab event. A user can also include inclusion and exclusion criteria, and identify patients with missing values of a specific laboratory test. Additionally, the value range can be further specified to occur within a range of time. In some embodiments of a results screen (FIG. 54), certain findings such as patient condition information can be missing. The user can include inclusion and exclusion criteria and identify patients with missing findings.

In addition to the cohort builder utility, cohorts may be entered into the system using the upload cohort utility. A user inputs data related to a patient, such as MRN and index data into an excel spreadsheet or other document. The spreadsheet is uploaded to the system and named or defined as a cohort object. Templates may be used for the spreadsheet to facilitate data transfer from the spreadsheet to the system. This cohort may be used in the system together with analytics, such as time to event, ED visit, hospitalization, clinic visit, mortality, laboratory and smart reports.

Figure 55:
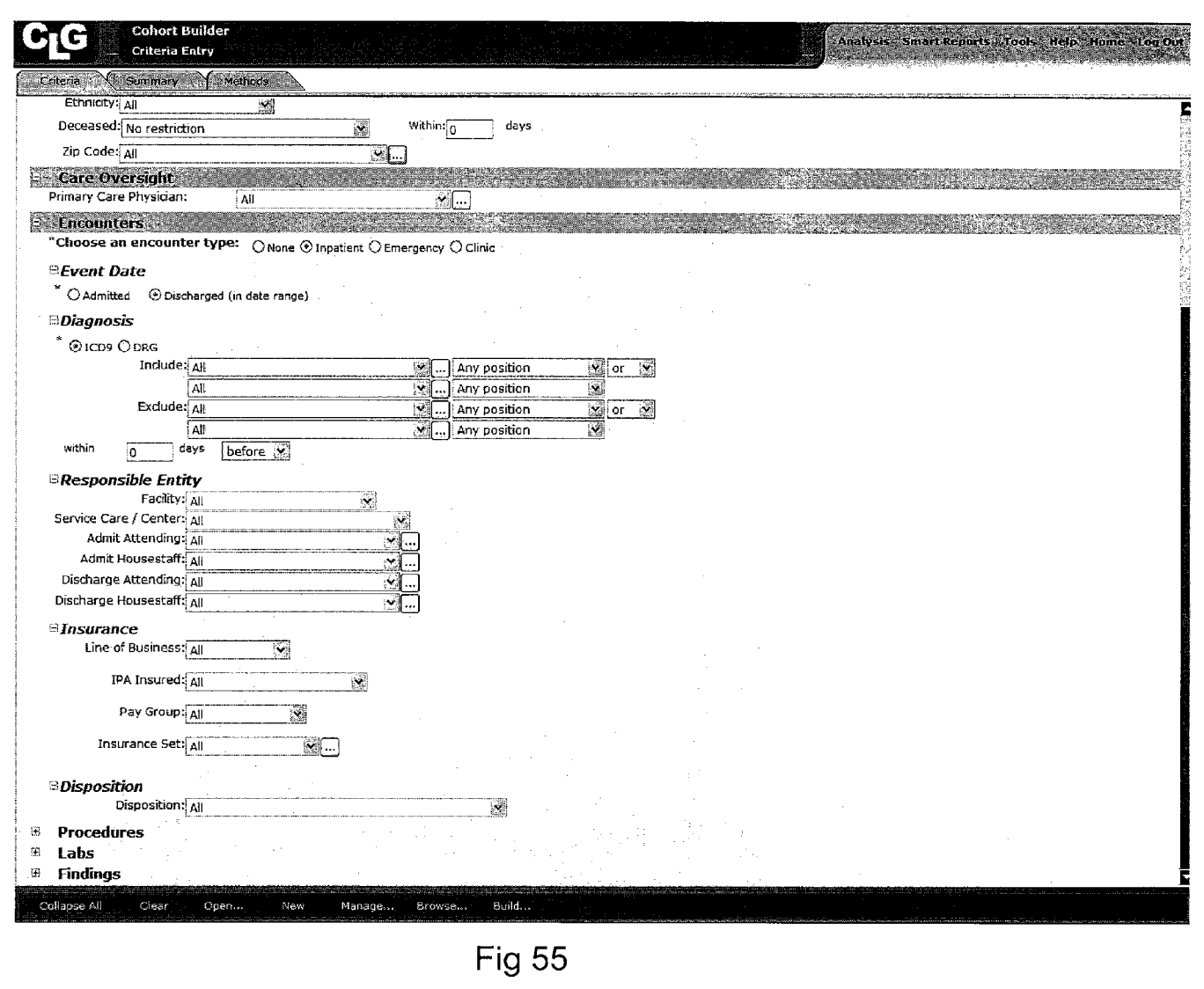

Cohort data can also be further restricted to patients having access to a particular physician or medical provider, for example, during a period of treatment or other interval of interest. The MD Sets in the Cohort Builder utility can be used to qualify a group of patients. In FIG. 55, which depicts an embodiment of the cohort builder encounters screen, a set of doctors, or individual medical providers, can be selected.

Cohort data can also be added indirectly, e.g., by using one or more of the analytics described herein. For example, data can be imported from a database or other data source, or entered in a data set, e.g., as described in connection with an analytic.

Figure 56:
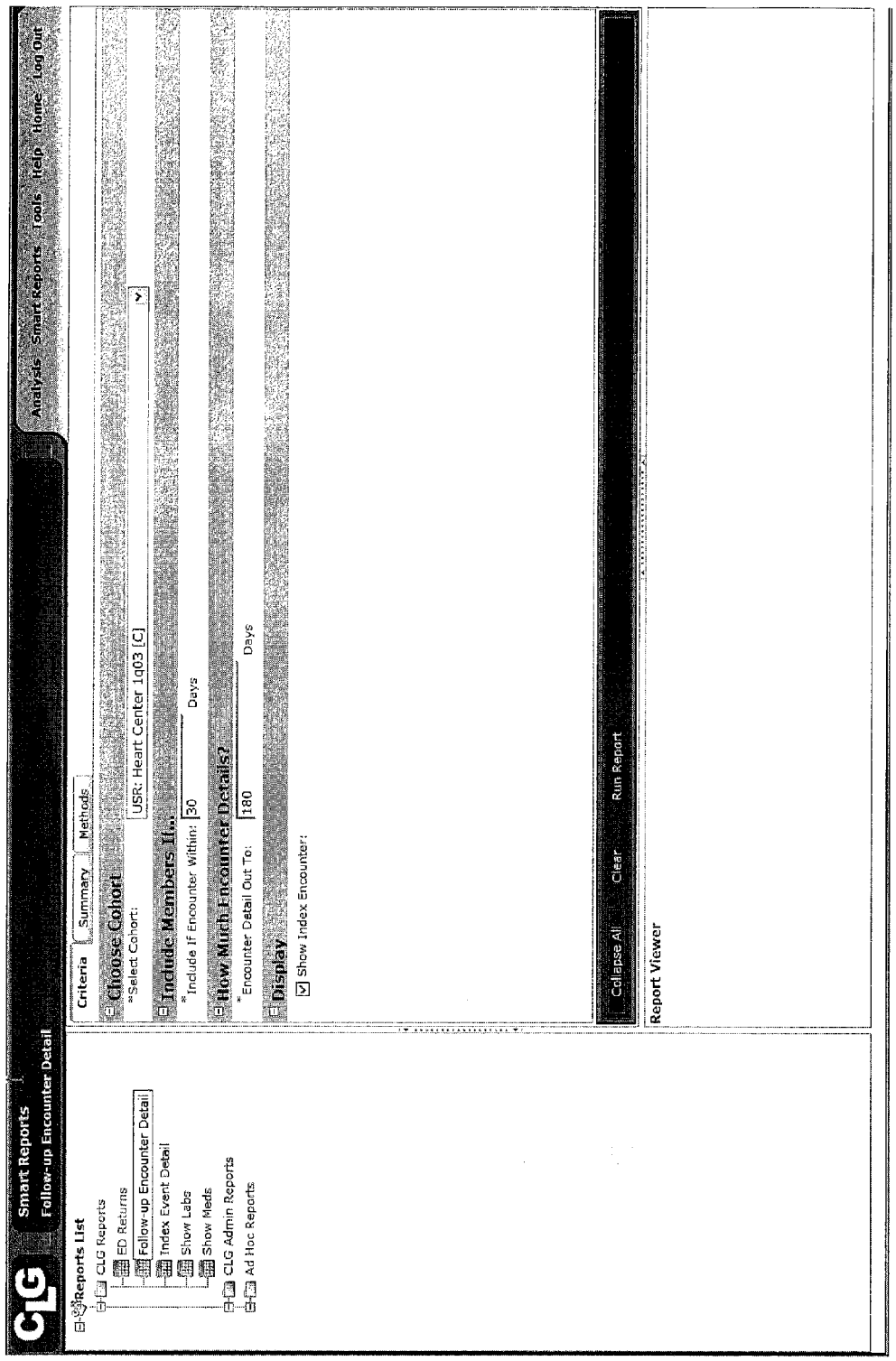
Figure 57:
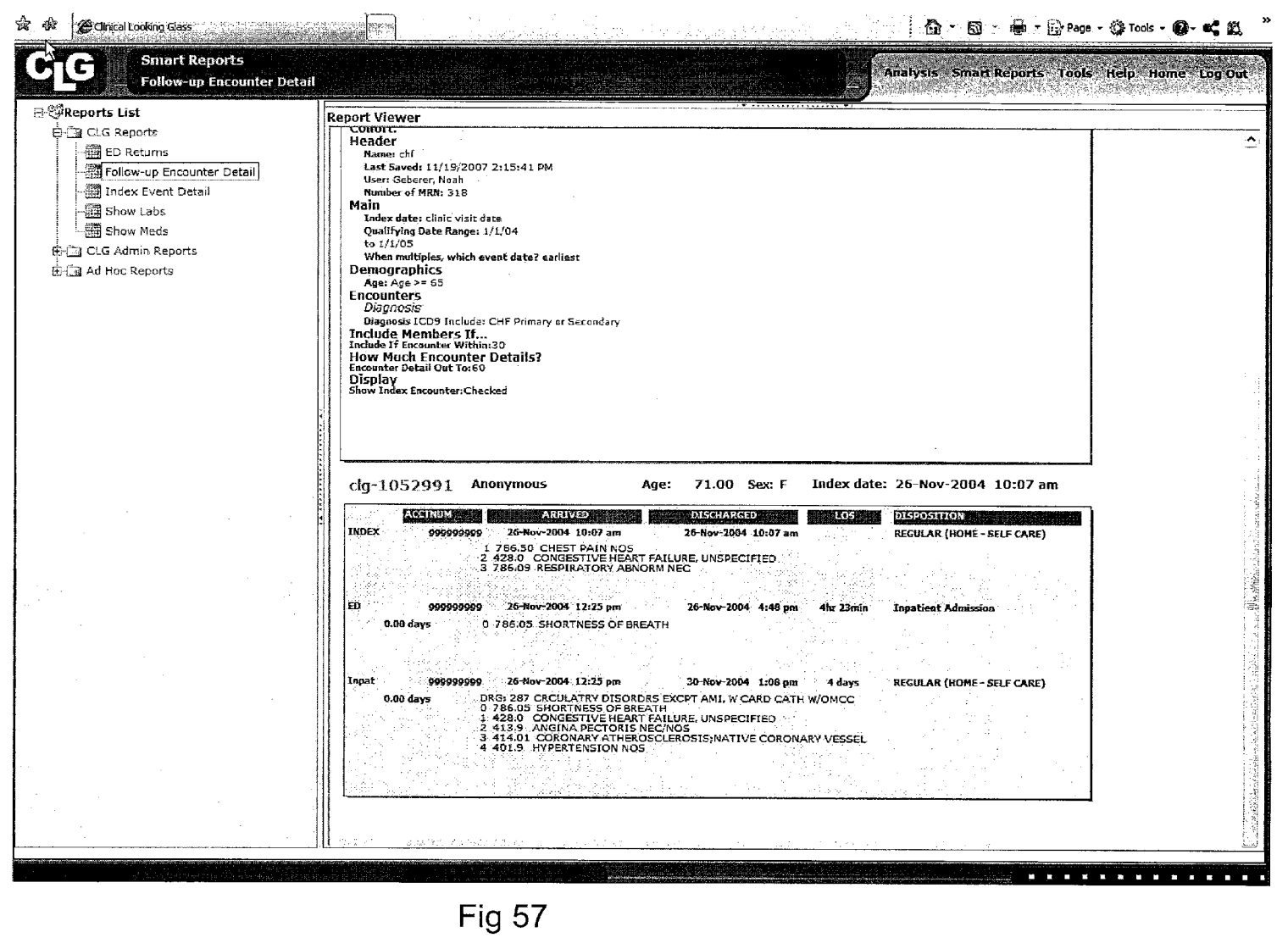

As described herein, reports are generated by the system providing on screen or hard copy information obtained by the system analytics and modules. Referring to FIG. 56, a cohort can be named and certain parameters entered to obtain follow up encounter detail. The encounter details can be for example, an emergency department (ED) visit or hospitalization event within a certain time period. In the embodiment shown in FIG. 56, the encounter detail is defined according to days. Selecting the run report button, a screen, such as the follow up encounter detail report depicted in FIG. 57, is obtained. The run report button and run report w/identifiers button are both provided in FIG. 56. Selecting the run report button provides a report that does not contain patient identifiers. Selecting the run report w/identifiers button provides reports including patient names and MRN numbers. Access to the identifier information is preferably limited to authorized users. The follow up encounter detail report includes for example, ICD-9 details of the ED visit or hospitalization for each patient selected for a follow up period. In preferred embodiments, the report is presented in adobe acrobat pdf format.

Figure 58:
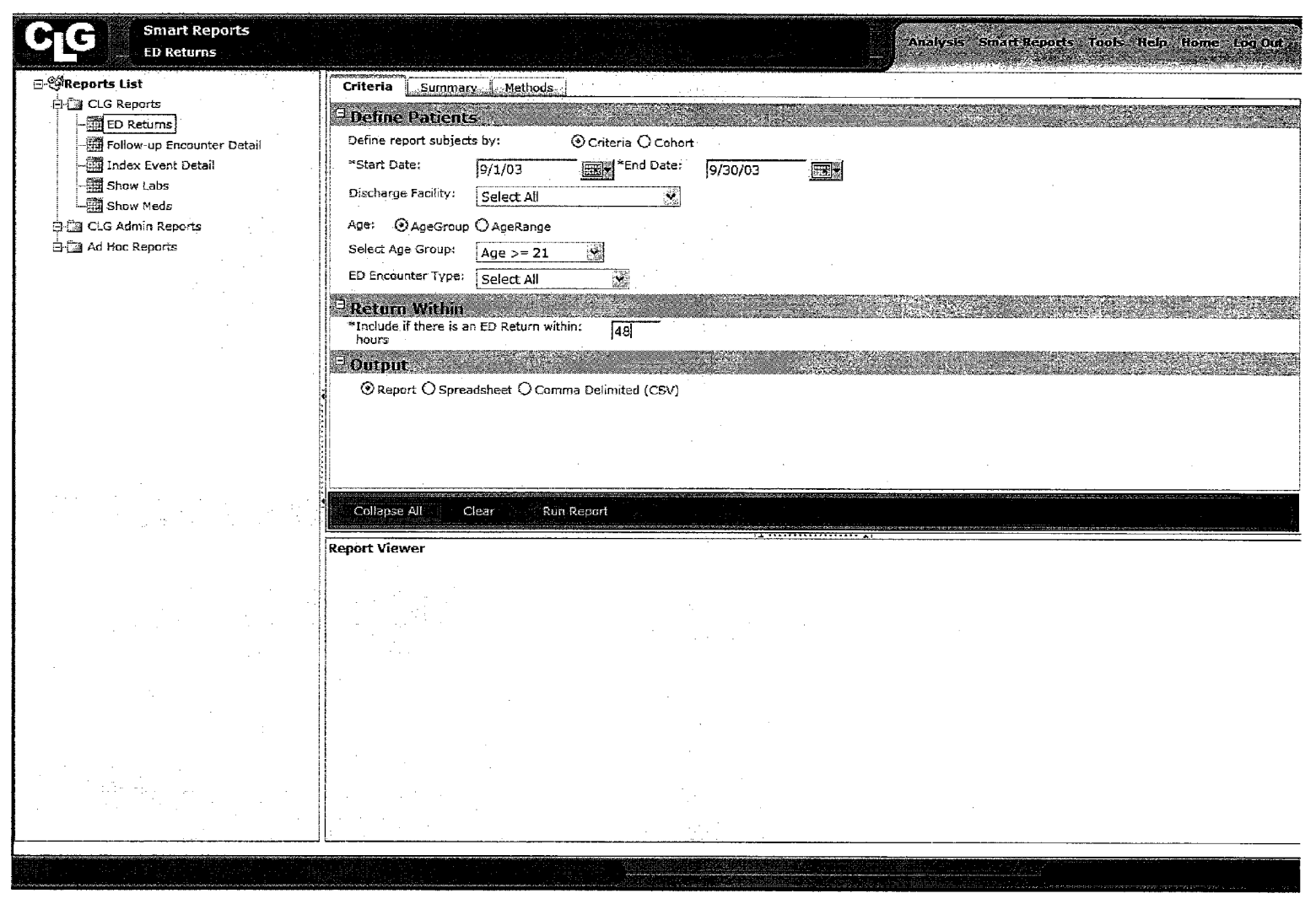
Figure 59:

Another report provided by the system is the ED Returns Report. This report allows the user to look at the quality of care of the emergency department by identifying those patients who have returned to the emergency department within a user definable period of time. The report information is restricted to the specific date range of ED discharge and permits restriction of discharge facility and age range, as shown in the fields of FIG. 58. Selecting the run report button of FIG. 58 provides the ED Returns report of FIG. 59. The ED Returns report includes ICD-9 details of the ED visit or hospitalization for each patient who returned to the ED within the specified time. In preferred embodiments, the report is output in adobe acrobat pdf file format.

Figure 60:
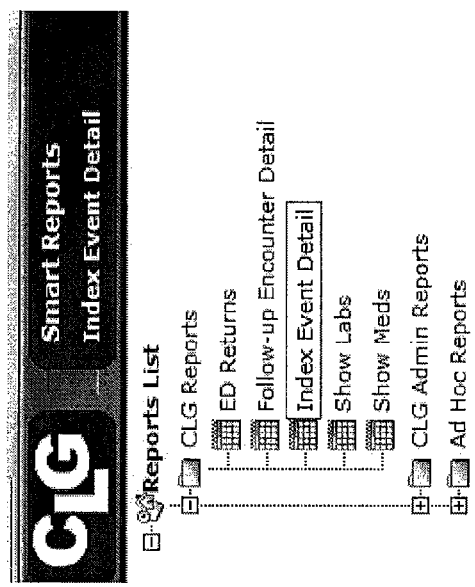
FIG. 60 depicts a screenshot of an analytic start page according to an embodiment of the invention.
Figure 61:
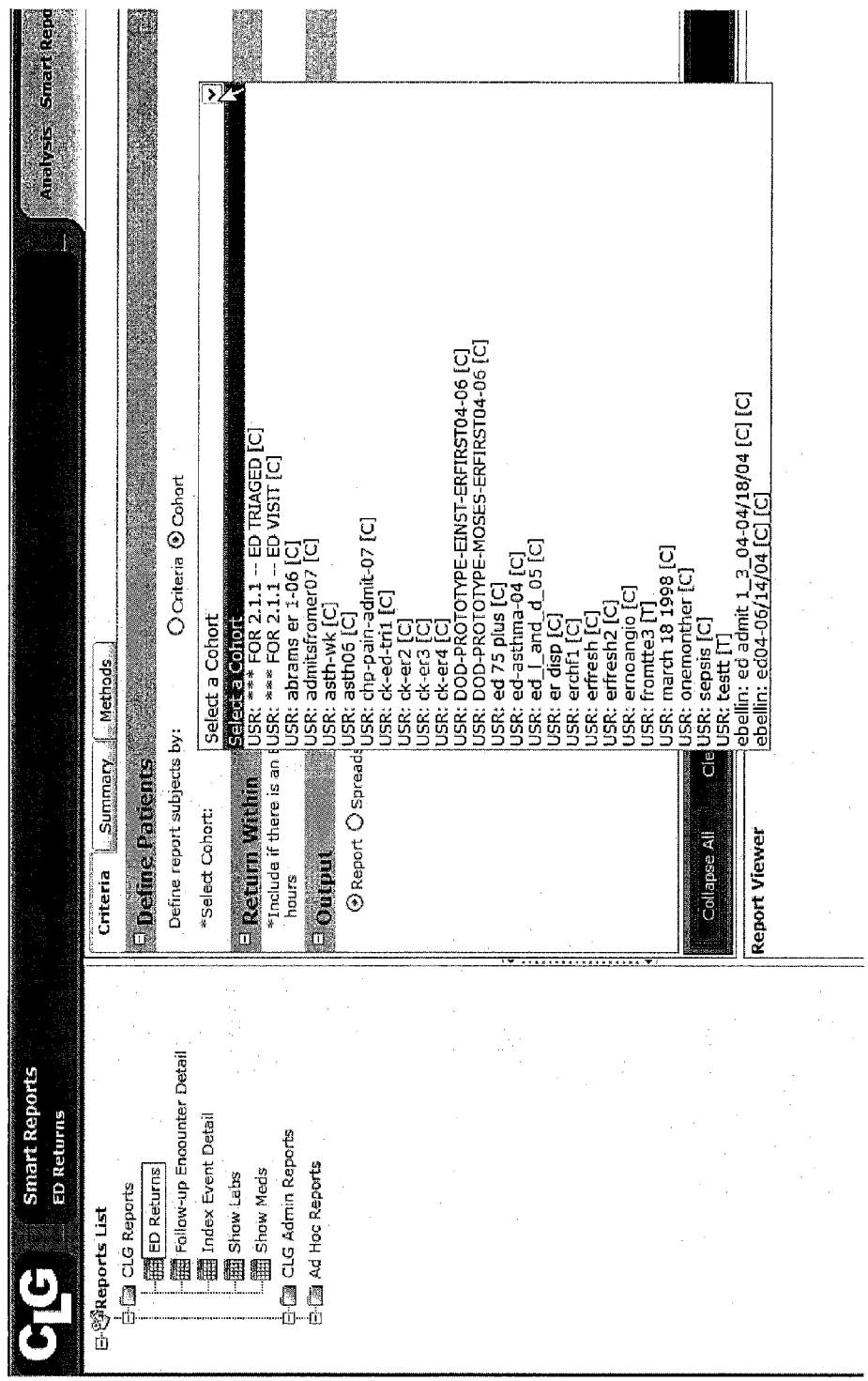
FIG. 61 depicts a reports selection screenshot according to an embodiment of the invention.

Another report provides Index Event Detail information. This report looks at the cohort chosen, identifies an index date and then displays the ICD-9s or DRGs appropriate to the index event, such as a hospitalization, emergency department visit, clinic visit, or other event. The report handles admission or discharge dates for the index date to yield the appropriate ICD-9s for the hospitalization. To obtain the report, Index Event Detail is selected from the Smart Reports menu, as shown in FIG. 60. The user can then select a cohort on which to run the report, from the screen depicted in FIG. 61. In preferred embodiments, the report is output in adobe acrobat pdf or Microsoft Excel file format.

Figure 62:
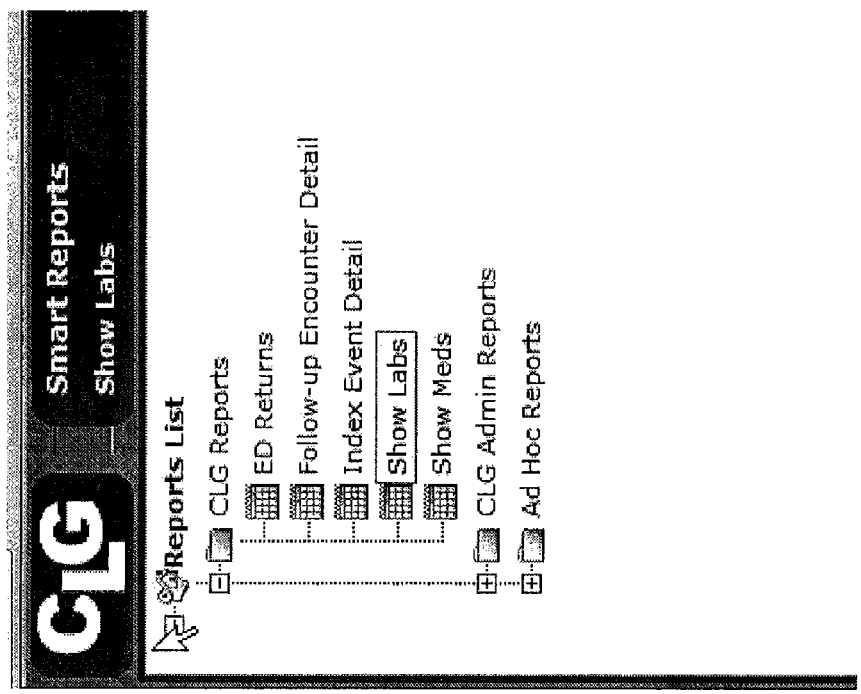
FIG. 62 depicts a screenshot of a selection page according to an embodiment of the invention.
Figure 63A:
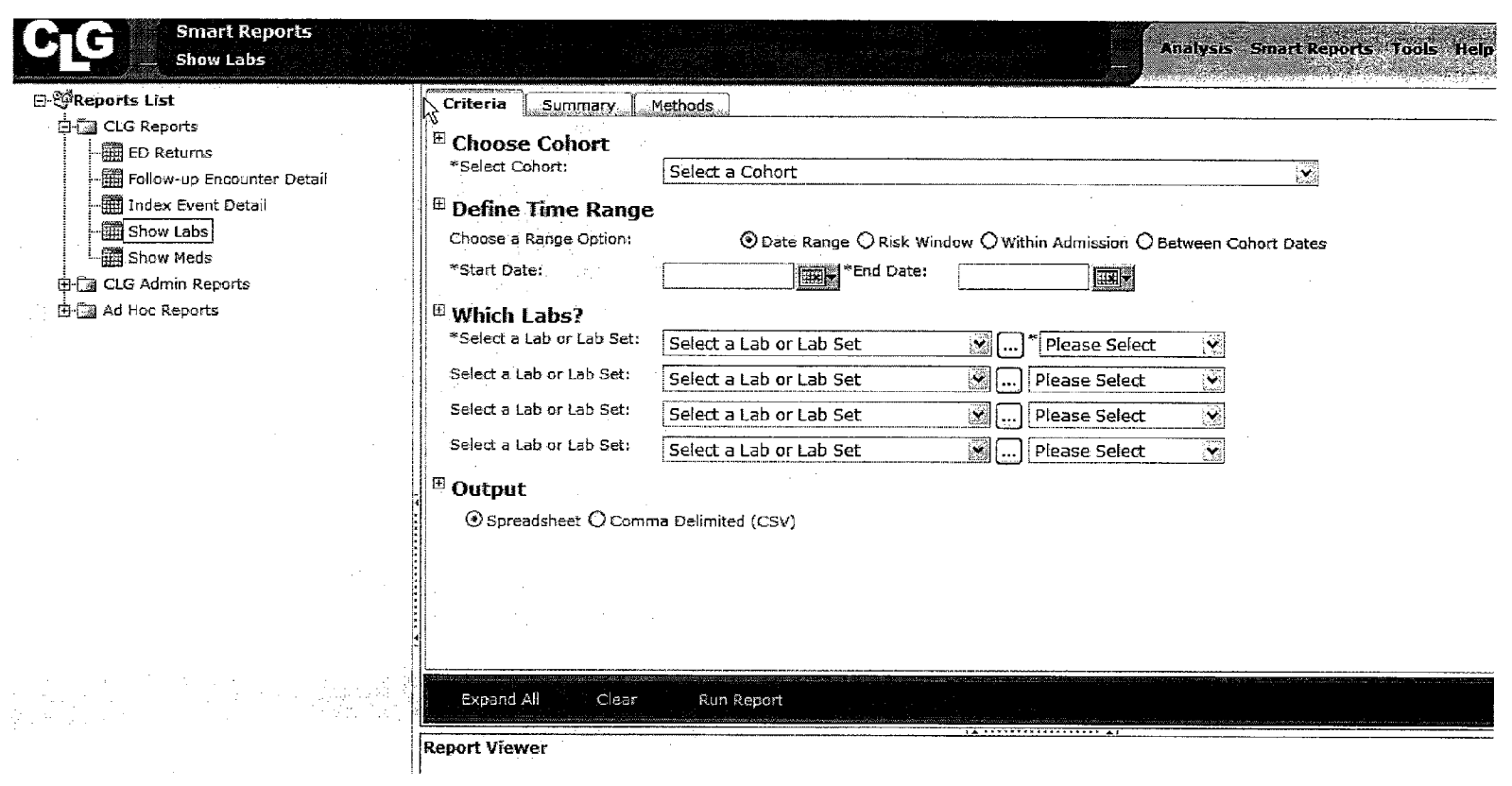
Figure 63B:
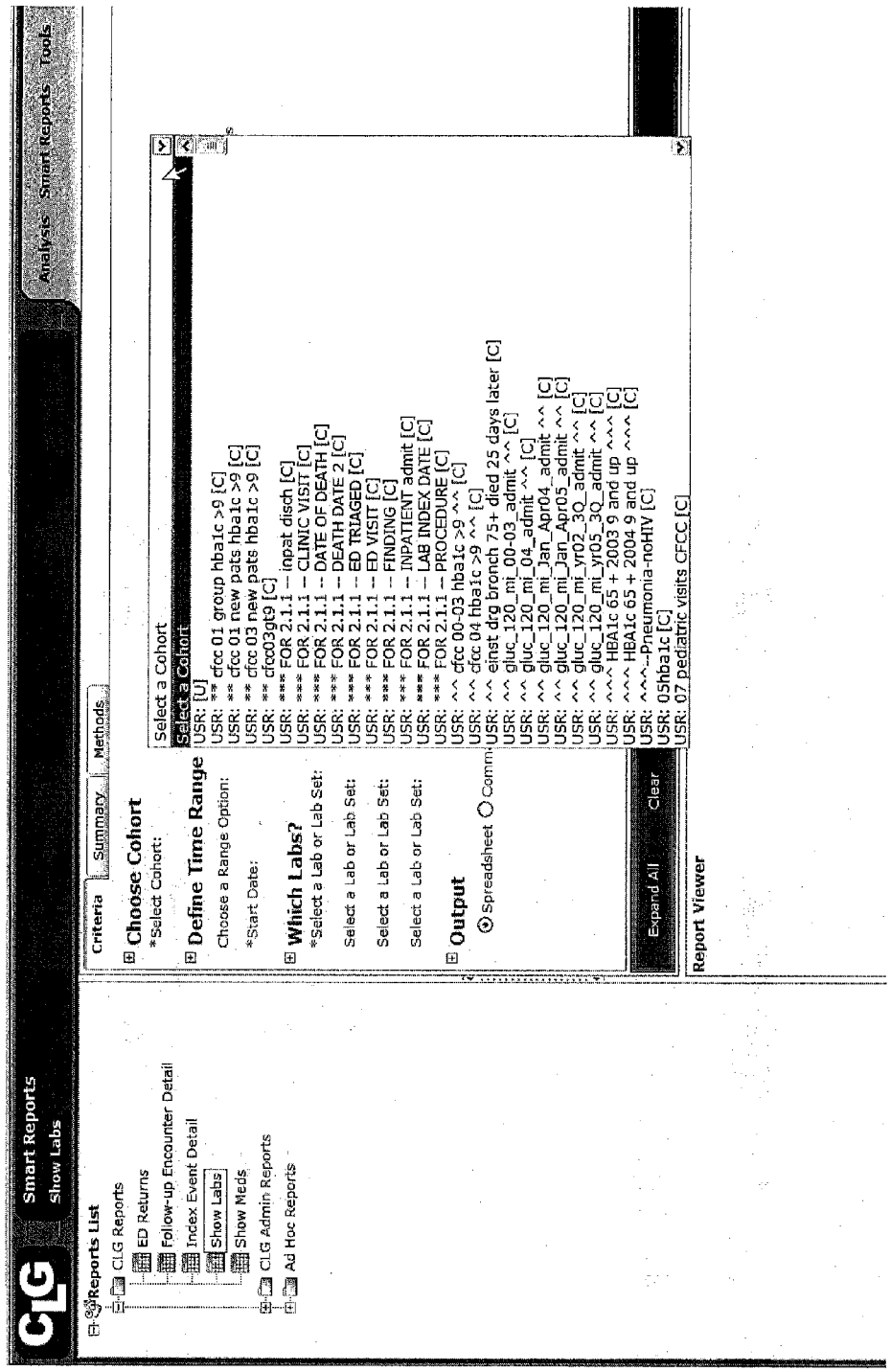

Yet another report provides laboratory values, in the Show Labs report. The Show Labs report provides laboratory values for a group of patients or a cohort. To obtain the Show Labs report, Show Labs is selected from the Smart Reports menu, as shown in FIG. 62. At the criteria entry screen for the Show Labs report, a cohort is selected, as shown in FIGS. 63A-B. A time range for the laboratory values is also selected in the criteria entry screen. The time range can be, for example, a date range, e.g. a calendar date range, risk window, which is a certain number of days on either side of an index date, within admission, which is within a specific hospitalization (this can be used when the cohort has as its index date the date of discharge from or admission to a hospital) or between cohort dates, which is the period of time for each patient defined as between the index date through therapeutic need end date. Finally, a laboratory test value is selected in the criteria entry screen, e.g. all, first, last, highest or lowest laboratory values. The output report is an excel spreadsheet, or other file format.

Time to Event

When a cohort has been built, as described herein, e.g., using Cohort Builder or from information input to a particular analytic, outcomes can be tracked, for example, by using the Time to Event Analytic, which is obtained by selecting the Time to Event button on the main screen (FIG. 4). The Time to Event Analytic provides the functionality to track outcome trajectory, e.g., cumulative incidence for achieving the outcome, incidence density of events with relative risk and risk difference comparisons between groups, or other events associated with groups or cohorts. Examples of target outcomes that are tracked include the following: Encounter, Result or Mortality. Encounters include, for example, a hospital admission, hospital discharge, emergency department visit, or clinic visit. The encounter can be further limited by specific ICD-9 code belonging to the encounter. Result includes, for example, a specific lab test result is achieved. Mortality indicates that a mortal event occurs. Generally, an index date is used, which is the date at which a patient qualifies as a member of the group. The Time to Event analytic uses the index date to calculate the elapsed time for each cohort member until date the cohort member achieves the target outcome or event.

Figure 43:
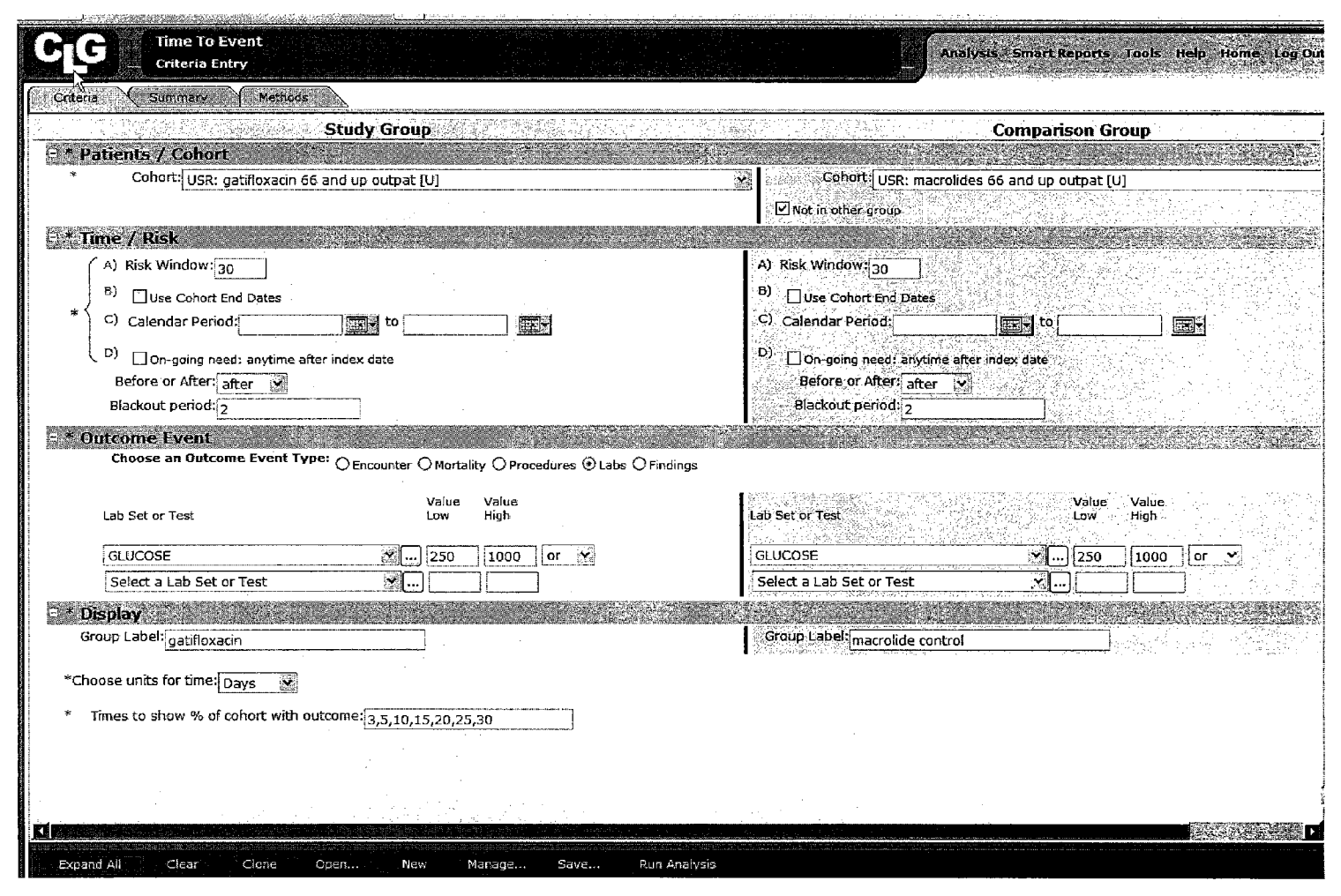

The Parameter Entry Screen, depicted in FIG. 43 is substantially similar to the Parameter Entry Screens described herein in reference to other analytics, and includes Target Events, e.g., Encounter, Results, Mortality, or other event. The parameter fields include cohort name, which is preferably a cohort previously created, e.g., using Cohort Builder. The risk window field is for parameters relating to the elapsed time from the index date of the members of the cohort object until time of event to be displayed on the graph. Any event that occurs after this time is deemed censored at the extreme of time on the graph display. The field titled Event After/Before/Around is for parameters related to the elapsed time calculated from the index time until the time after when the event occurred or the time before when the event occurred. The field titled Group Label is for labeling the group. Units for Time is a field for a parameter to set the measure of time, e.g., days or hours. The Time to show % of Cohort with outcome field is for setting time points at which a table will be constructed to display the cumulative percent of the population which has achieved the outcome of interest by the time selected. The not in other cohort check box is for eliminating patients in the comparison cohort who also appear in the study cohort, e.g., Group 2 cohort who appear in the Group 1 cohort. Exclusion generally requires a match of MRN or other patient identifier. Additional parameters include those discussed herein, e.g., comparison groups, ICD9 sets, Insurance, Inpatient, events, facilities, emergency department, and clinic visits.

Figure 44:
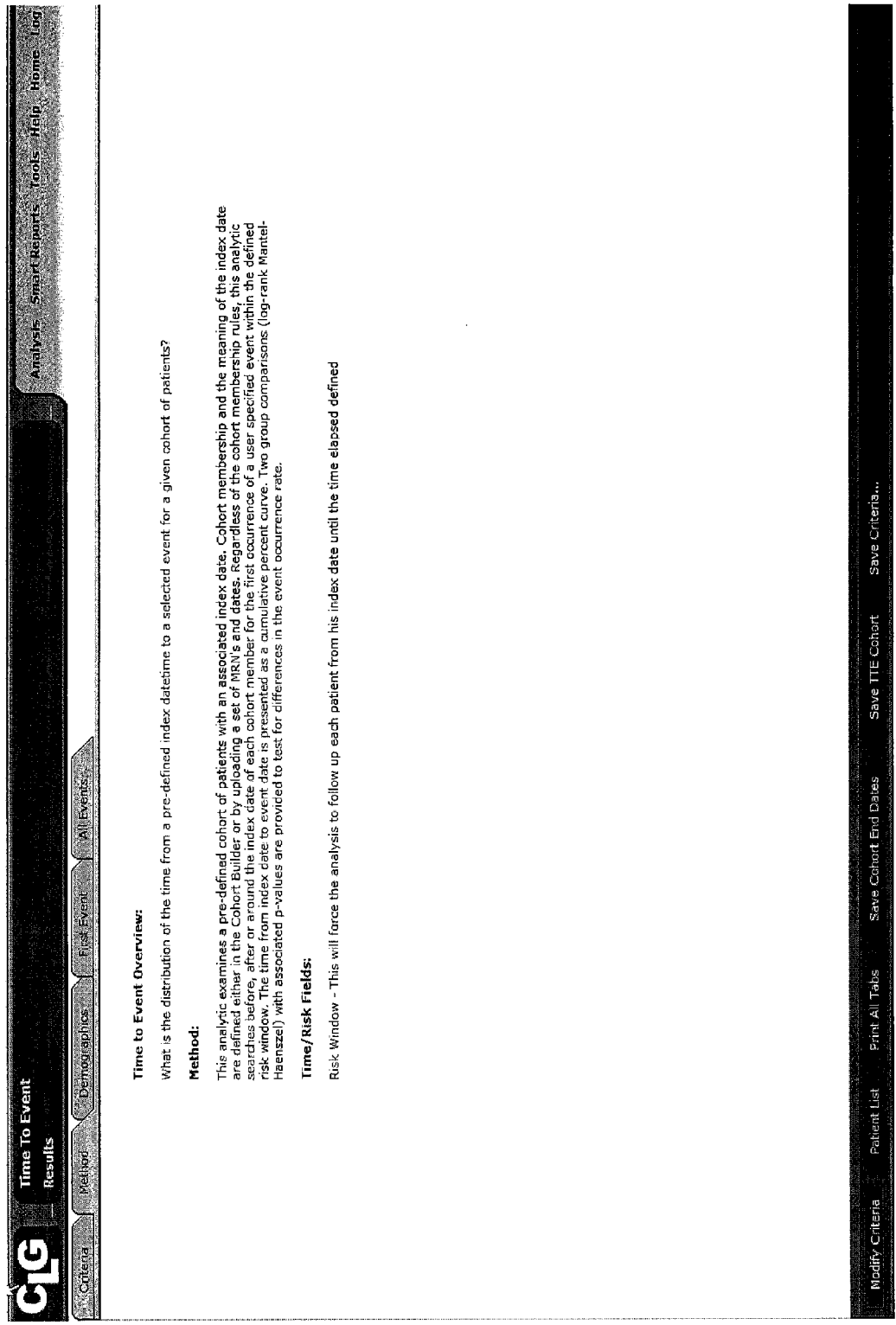
Figure 45A:
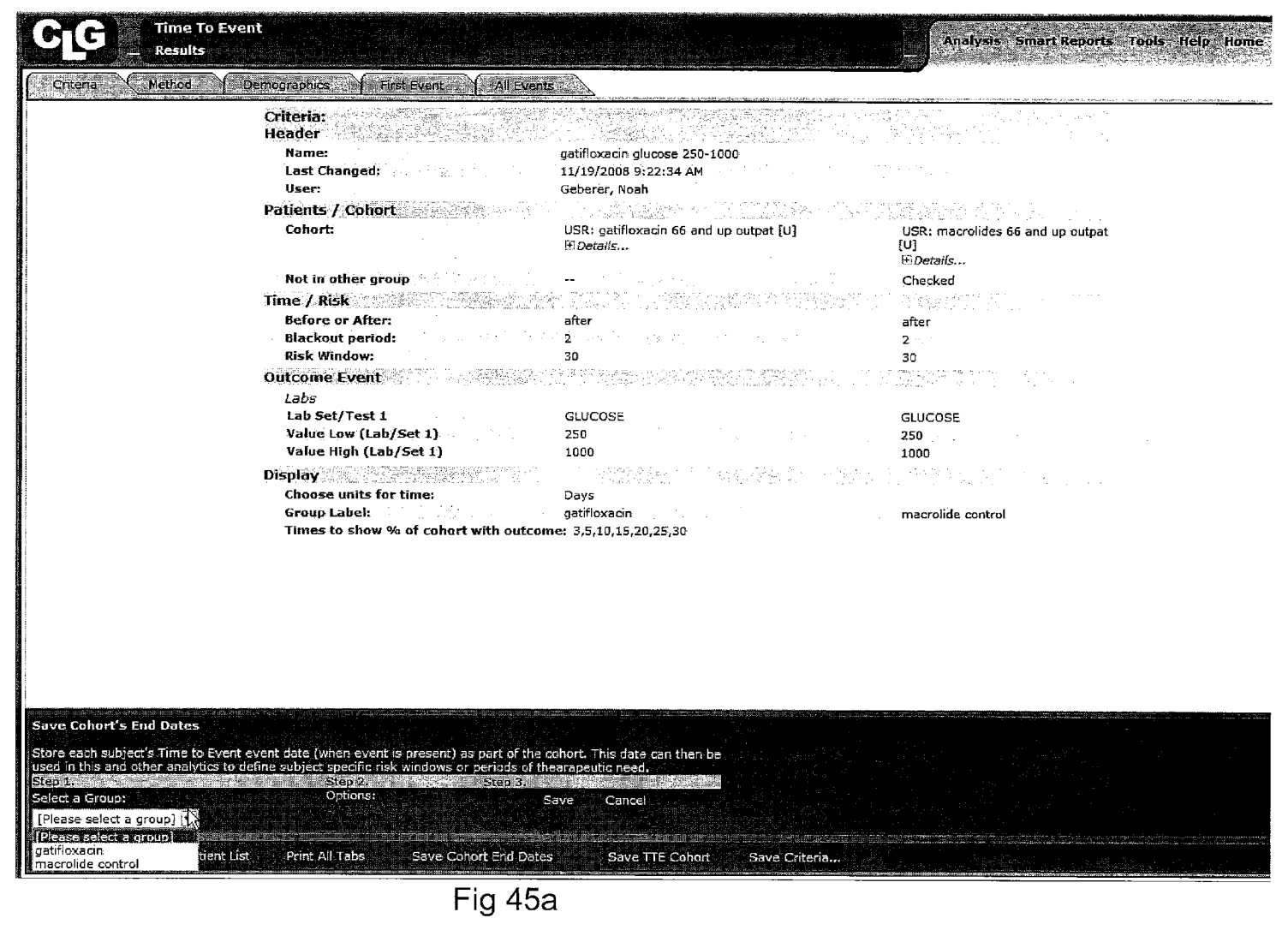
Figure 46:
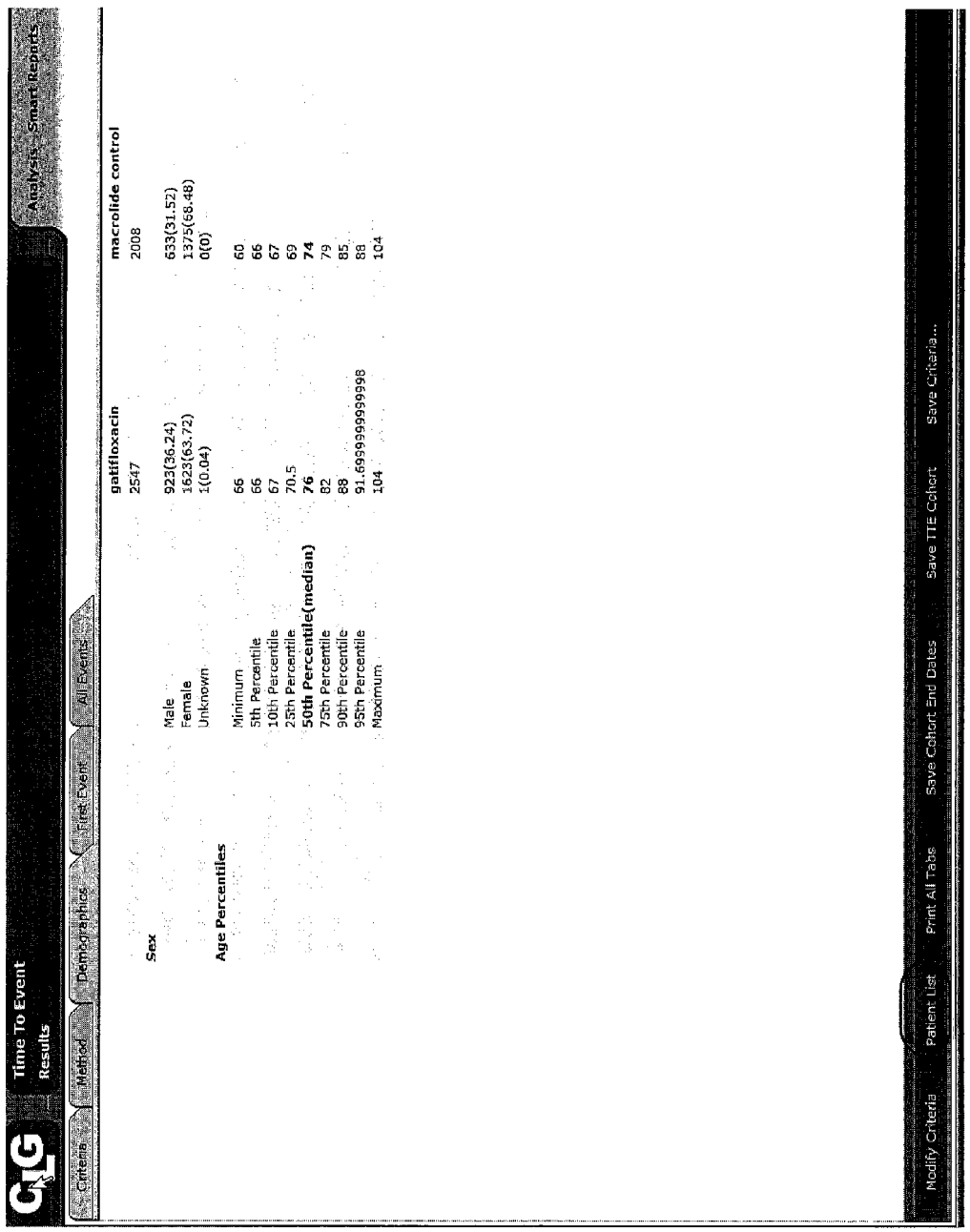
Figure 47:
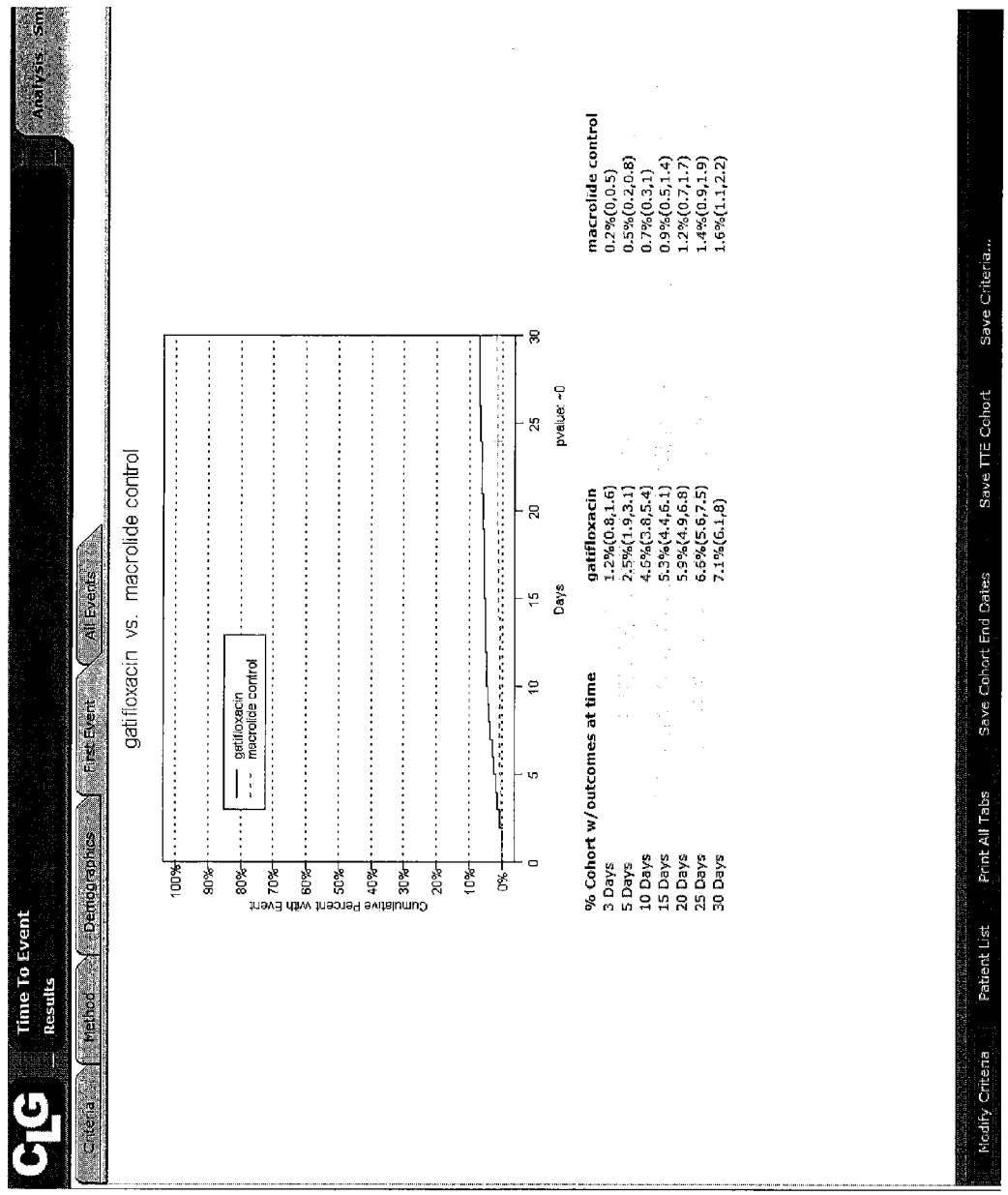

When the parameters are entered, the Time to Event Analytic is run by selecting the Run Analysis button (FIG. 43). The Results screens are obtained, FIGS. 44-47. The Method Screen (FIG. 44) summarizes the technique used by this analytic. The Results Method screen is presented in a substantially similar manner to the Results Method screen of the other analytics described herein. The Criteria screen (FIG. 45) is substantially similar to the criteria screens described herein in connection with the other analytics, and generally summarizes the criteria used to run the analytic. In addition, the Criteria screen provides buttons to "store event date" which, when selected leads to the screen shown in FIG. 45A. Storing an event date in relation to a cohort allows a user to store each subject's time to event event date (when the event is present, or an end date) as part of the cohort. This date can be used in the Time to Event Analytic or other analytic to define subject specific risk windows or periods of therapeutic need. Alternatively, storing an event date can be used to create a new cohort from subjects in the Time to Event Analytic who experienced an event. Storing the cohort end date provides the ability to follow a cohort to an end date. For example, a study of a cohort of patients with atrial fibrillation for adequate anticoagulation, the cohort can be studied from the time of a GI hemorrhage, or other diagnosis, to the time to discontinue anticoagulation. When the system is informed of a hospital admission related to a GI hemorrhage, the system would ignore any event and risk time accumulated after the end date.

Figure 52:
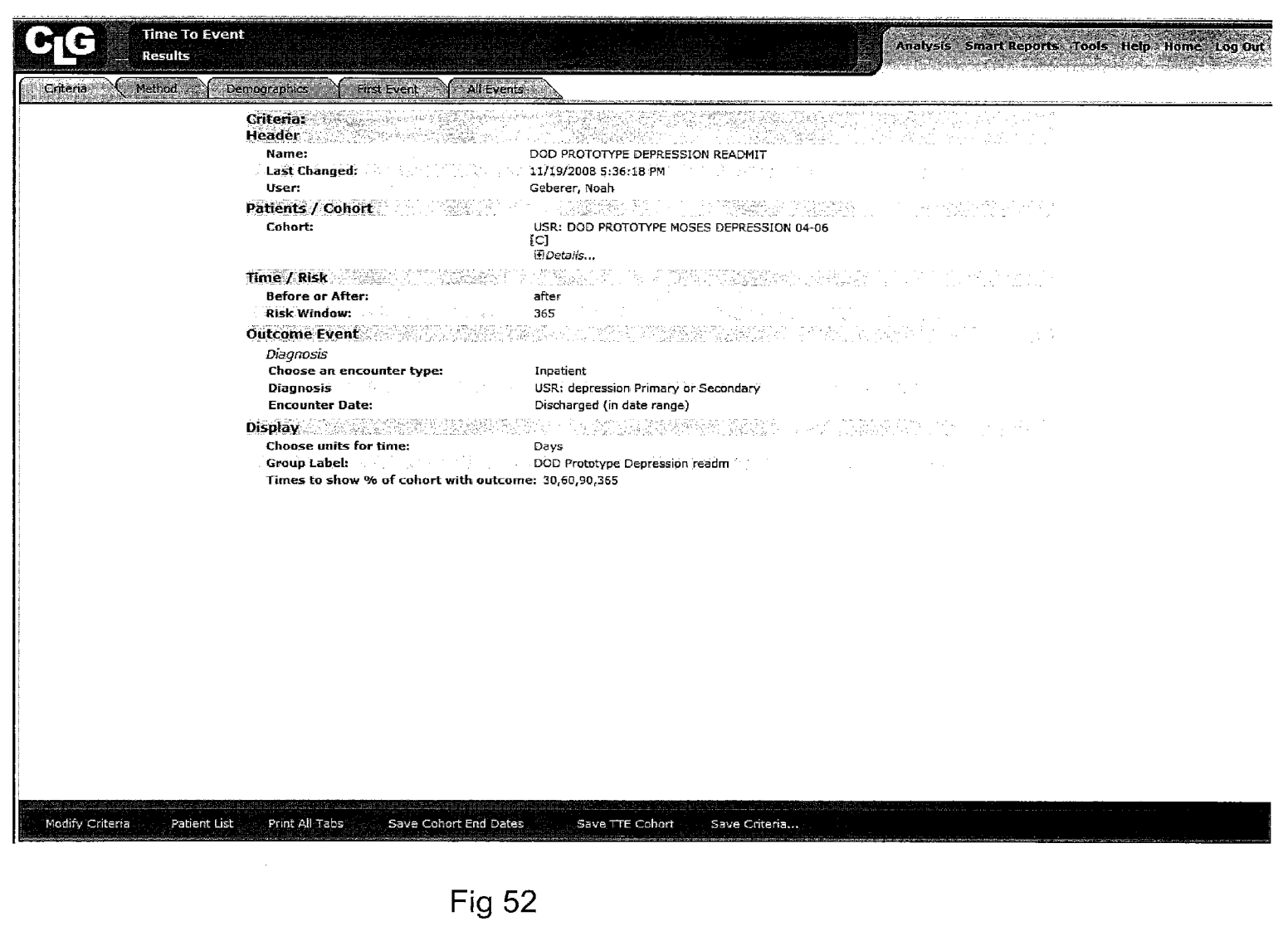
Figure 53:
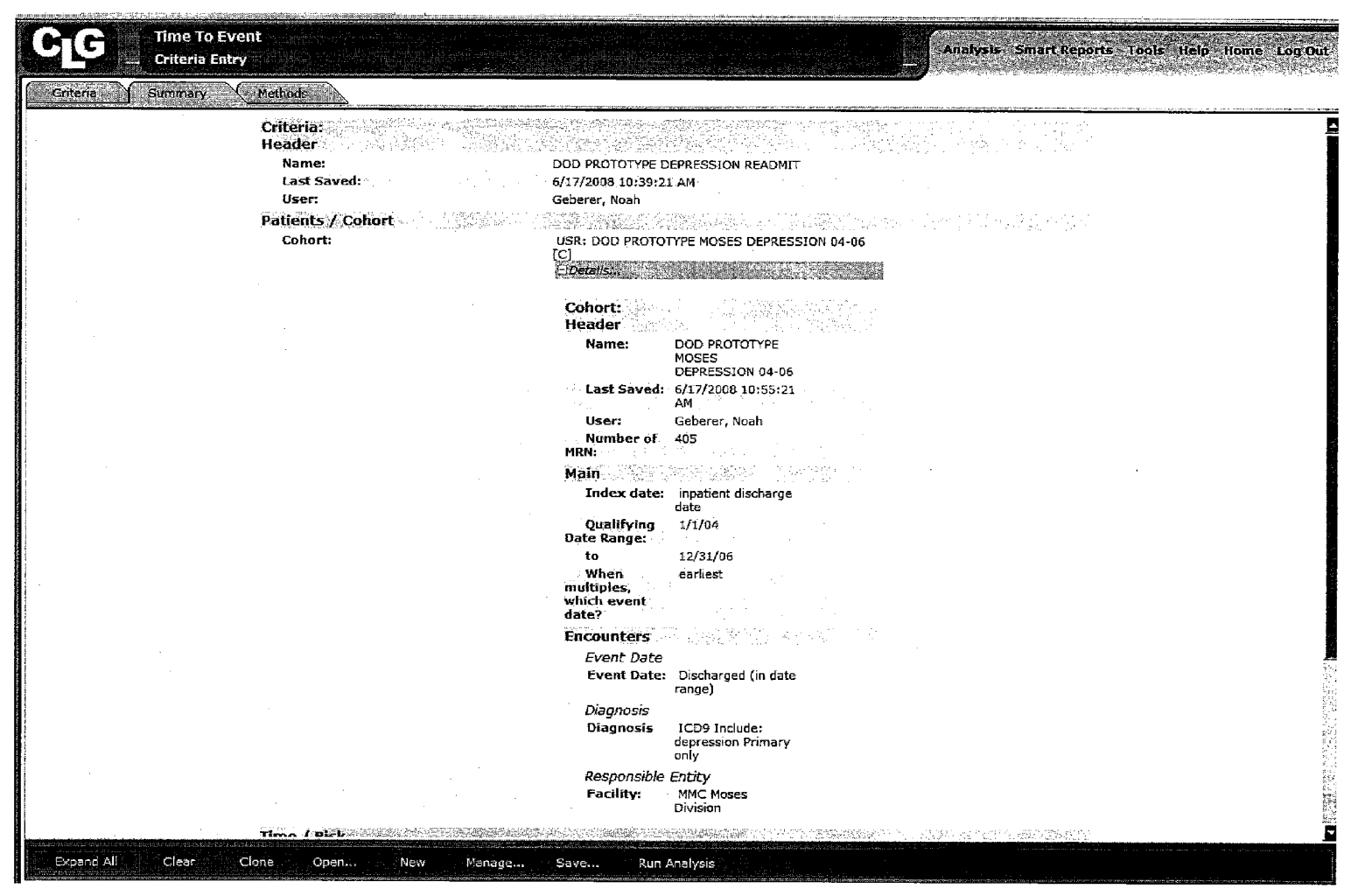

In another embodiment of the criteria screen (FIG. 52), a details button may be selected to obtain details related to the cohort, as shown in FIG. 53, such as name, author, number of members in the cohort, index event, date range, encounter or event. The Demographics screen (FIG. 46) is substantially similar to the demographics screen described herein in connection with the other analytics, and generally summarizes demographic information, e.g., gender and age distribution of the cohort used in the Time to Event analysis. The patient list containing information related to the cohort can be obtained by authorized persons by selecting the patient list button depicted on FIG. 46. The Outcomes screen (FIG. 47) depicts the cumulative percent incidence curve of the endpoint of interest in the Time to Event analysis. More specifically, groups are compared on the graph with a p-value calculated below the graph on the right. Below the graph is a summary table providing the cumulative incident proportion at 20, 60, 90, and 180 days as well as the 95% confidence interval. In some embodiments of the outcomes screen, the events can be separated into first event, target event and all events, or other events, where there is more than one event.

Ad Hoc Statistics

A binomial confidence interval calculator is provided which accepts a numerator count of success or failure and a denominator number of trials and yields a proportion and a confidence interval. This analytic permits a user to view group variables, time and censor variables to display a cumulative percent by group that achieved a desired endpoint by a certain time of interest, which, among other things, provides data summaries that are not overtly affected by outlier data points.

Event Canvas

According to a further embodiment, a system and user interface are provided where more complex clinical questions may be constructed and more detailed database queries may be performed. The user interface (and supporting software) are called "Event Canvas" in reference to the flexibility afforded the user in constructing query expressions, thus "drawing" on the canvas. Similarly, an interface (including an edit bar) where a user may define a wide variety of events for constructing a question is called a "palette" in this embodiment.

Figure 64:
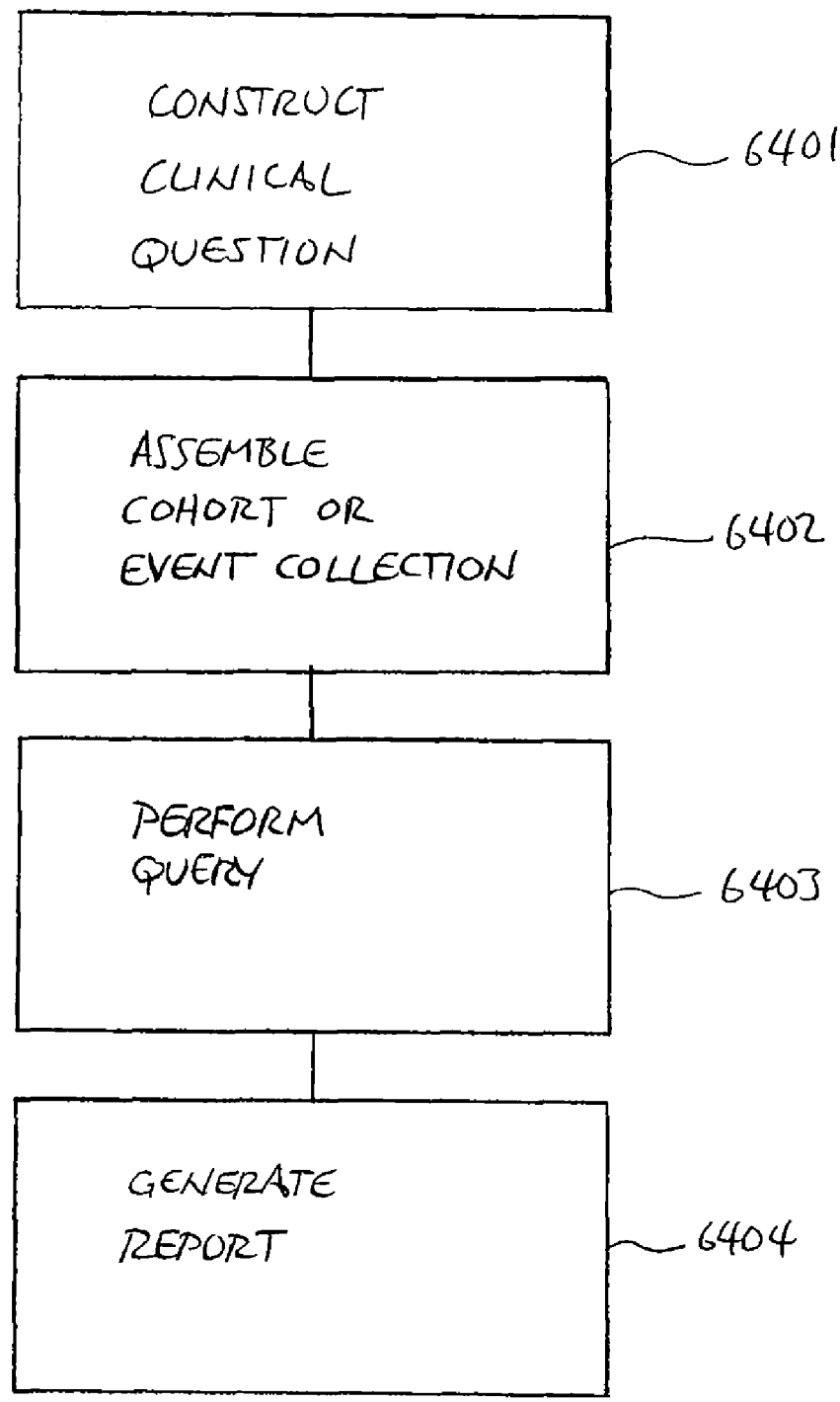
FIG. 64 shows a flowchart schematically illustrating a process for building a cohort or event collection to answer a clinical question, in accordance with an embodiment of the disclosure.

A flowchart schematically illustrating use of the Event Canvas is shown in FIG. 64. The user constructs a clinical question, which may include multiple event conditions and logical operators (step 6401). These conditions (qualifying events) and the user-defined logic are then used to assemble a cohort of patients or, alternatively, a collection of events (step 6402). As noted above, the events may be clinical events, administrative events, or a combination thereof. A query engine, described in more detail below, performs the database query (step 6403). A report responding to the original clinical question is then generated (step 6404); generating the report typically includes use of Web-based statistical services.

As an example, a user wishing to study a specific set of diabetic patients might construct the following clinical question: "Find diabetic patients over the past 10 years who have also had a high cholesterol lab result within 30 days of their diabetes diagnosis date but have not had any eye exams in 2006."

It will be appreciated that this question specifies multiple events (diabetes diagnosis, cholesterol lab test, eye exam) in restricted time periods (past 10 years, within 30 days, in 2006), linked by logical operators (in this case, AND and NOT). A patient (or patient record) qualifies to be included in the population of interest if that patient has those events in the record; the listed events are therefore termed "qualifying events."

An event may have several attributes associated therewith. For example, a "cardiac echo test" is an event with attributes such as: left ventricular ejection function, status of mitral valve, status of aortic valve, etc. The clinical question may also specify demographic attributes of the patient, such as age, race, gender, etc. The time or time period may be characterized as "when in" (e.g. during a specific calendar year, calendar month, etc.) or "within" (e.g. within 30 days of last hospital admission, after more than 1 year after discharge, etc.).

In this embodiment, complex qualifying events may be grouped together, with the group represented by a logical expression; the group may be manipulated on the event canvas in the same manner as a single event. In the above example, "diabetes diagnosis" may be viewed as a group with three qualifying events: (1) a recorded ICD-9 billing diagnosis, (2) Hemoglobin A1c value greater than 7 (indicating diabetes, as understood by those skilled in the art), or (3) a problem list record of diabetes. The user may decide that any one of these events would qualify a patient for inclusion in the population of interest. These three events, linked by the OR operator, would then be collected as a group; the first-occurring of the events for each patient would be taken as the qualifying event. More generally, in this embodiment a group is a collection of events joined by logical operators (AND, OR, NOT) from which a single representative event (with a corresponding date and time) is used to represent the group truth solution in further processing of statements on the event canvas. The user must choose which of the group's events' date/time will represent the group to the other logical expressions on the event canvas.

Figure 65:
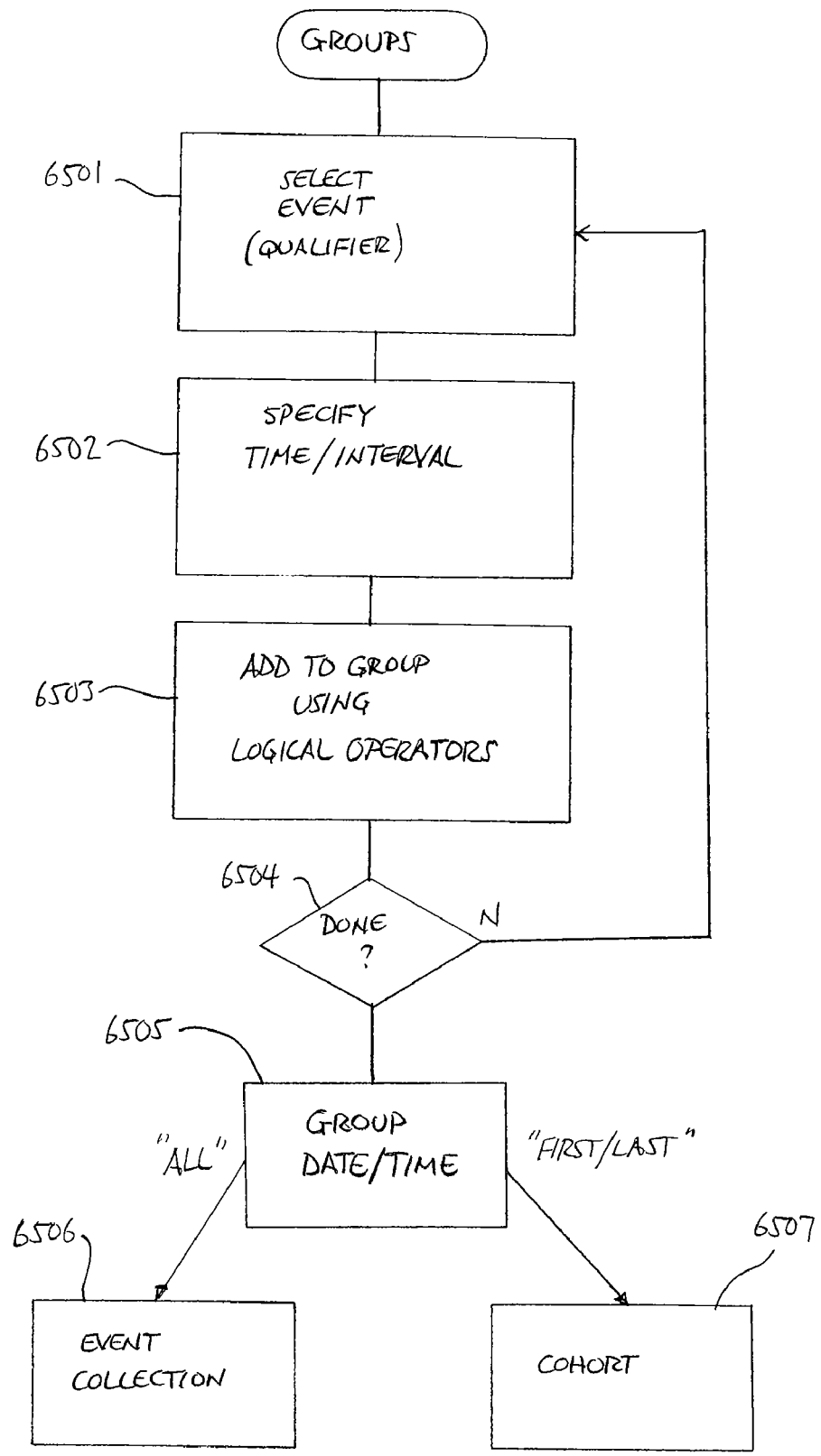
FIG. 65 shows a flowchart schematically illustrating a process for grouping qualifying events to define a cohort or event collection.

Steps in constructing a group of events are diagrammed in FIG. 65. The user selects an event (step 6501) and specifies a time or interval ("when" or "within") to be associated with that event (step 6502). Plural events are linked using logical operators (step 6503). After all the group's events are specified (step 6504), the user has the option of choosing "all events", "first event" or "last event" (step 6505). Choosing "all events" results in including patient records where all the events in the group's conditions are met. This may result in a patient record being included more than once; for example, the event "hospital admission in 2007" will have a patient record included twice if that patient was admitted to the hospital twice in 2007. This set of patient records is referred to herein as an "event collection" (step 6506). Choosing "first event" or "last event" results in including patient records where a given patient record is included only once. This set of patient records is referred to herein as a "cohort" (step 6507).

A description of a cohort built in response to the clinical question given above is shown in FIG. 66. The cohort may be given a name 6600. The three qualifying events 6601-6603 indicating diabetes are linked together with the OR operator 6604. The "diabetes diagnosis" criterion is combined with the "high cholesterol" and "no eye exam" criteria through the AND operator 6606. It is noteworthy that "high cholesterol" is not defined as an event in itself, but is instead expressed as a lab test result having a certain value (here, LDL>130), occurring in a specified time period using a WITHIN modifier 6608. The "no eye exams" criterion is defined by using the negation operator 6607 and a WHEN IN modifier 6609.

In accordance with the present disclosure, a user builds a cohort or event collection on the Event Canvas user interface, described more fully below.

Event Canvas: User Interface

Figure 67:
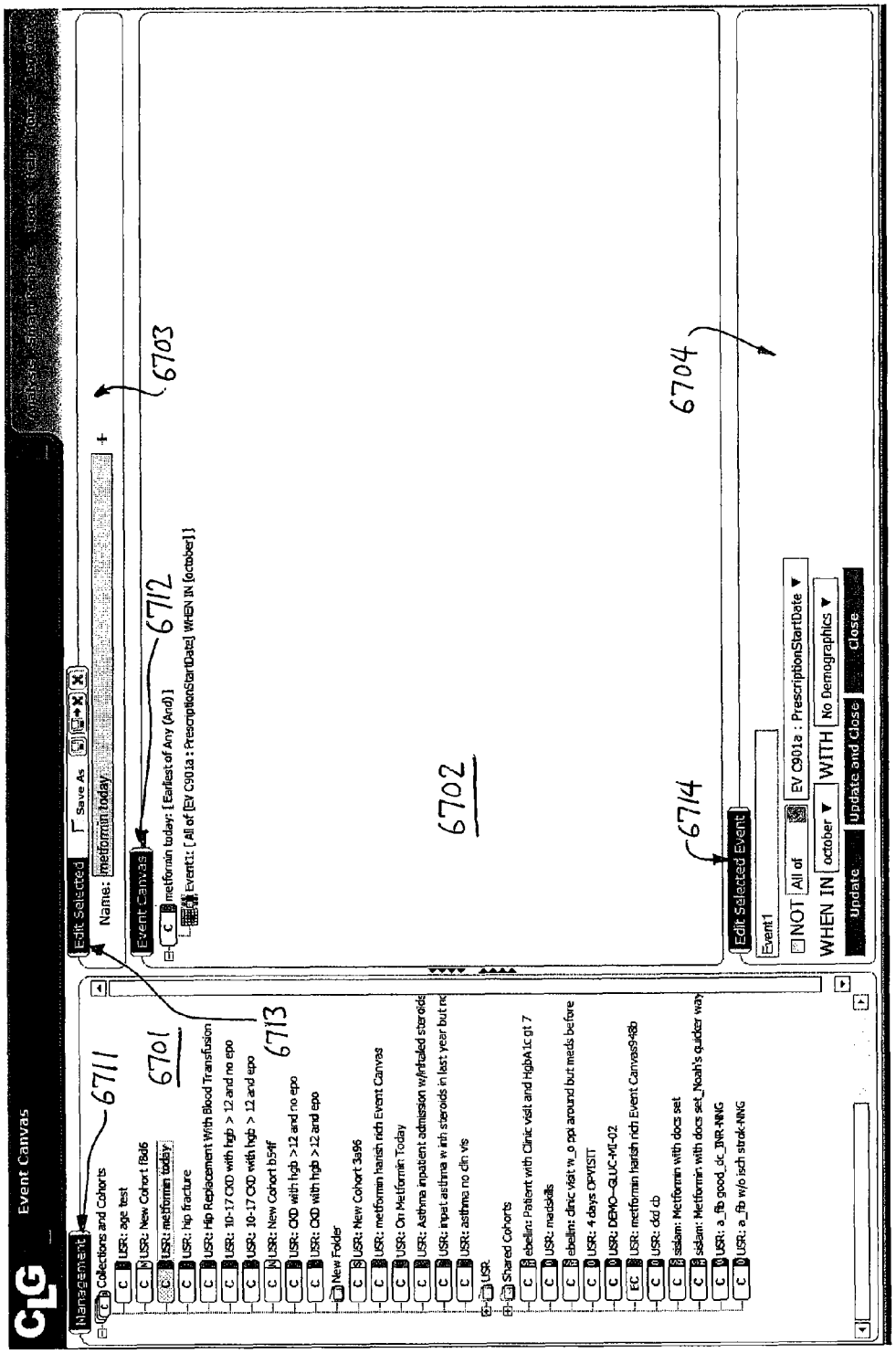
FIG. 67 shows a screenshot with an example of a user interface including an Event Canvas, in accordance with an embodiment of the disclosure.

A screenshot illustrating an embodiment of a user interface including the Event Canvas appears in FIG. 67. The screen in FIG. 67 is divided into four areas: a Management windowpane 6701, the Event Canvas 6702, a control bar 6703, and an edit bar 6704. In this embodiment, these areas have the identifiers Management, Event Canvas, Edit Selected, and Edit Selected Event 6711-6714 respectively.

As shown in FIG. 67, the Management windowpane 6701 has a directory of folders containing cohorts and event collections. In an embodiment, this windowpane is configured so that the user may activate a menu 6810 and sub-menu 6811 (see FIG. 68) to perform various tasks, including building a new cohort or event collection. As shown in FIG. 69A, this windowpane may also be configured so that selecting an item (e.g. clicking on the name of the item with a mouse) causes another menu 6910 to be displayed, from which a summary of the item may be ordered using a sub-menu 6911. FIG. 69B shows a directory entry in the windowpane for a cohort in this embodiment; the icon 6912 indicates a cohort. Similarly, as shown in FIG. 69C, the icon 6913 indicates an event collection.

Figure 70A:
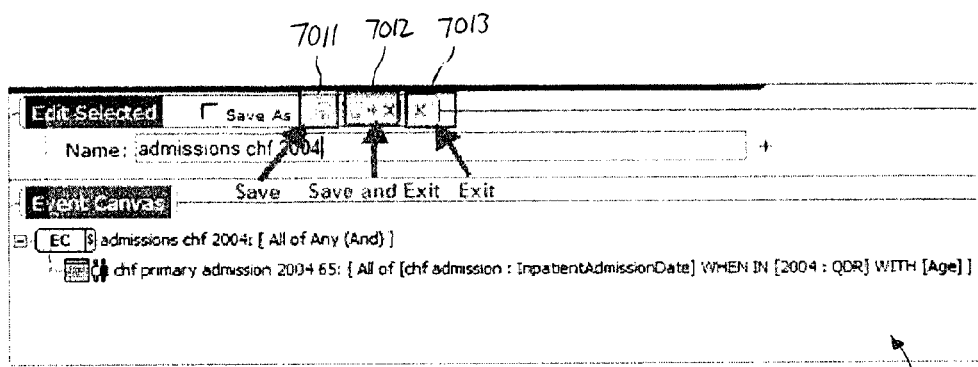
FIGS. 70A and 70B show screenshots detailing the control bar and edit bar, respectively, in the Event Canvas user interface of FIG. 67.

The control bar 6703 includes "Save", "Save and Exit" and "Exit" features for saving and/or closing work on the event canvas; these features are activated using suitable buttons 7011-7013 on the control bar, as shown in FIG. 70A.

Figure 70B:
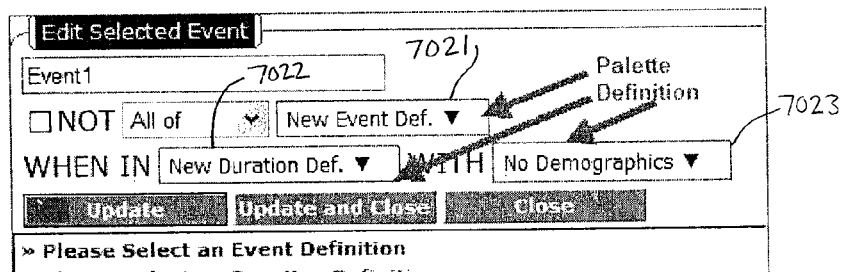

In an embodiment, the edit bar 6704 includes three drop-down windows 7021-7023, as shown in FIG. 70B. With windows 7021-7023, the user may enter into the definitional palettes for "painting" a cohort or event collection definition on the event canvas: window 7021 for the event definition palette, window 7022 for the duration definition palette, and window 7023 for the demographics palette.

Event Definition

Figure 71:
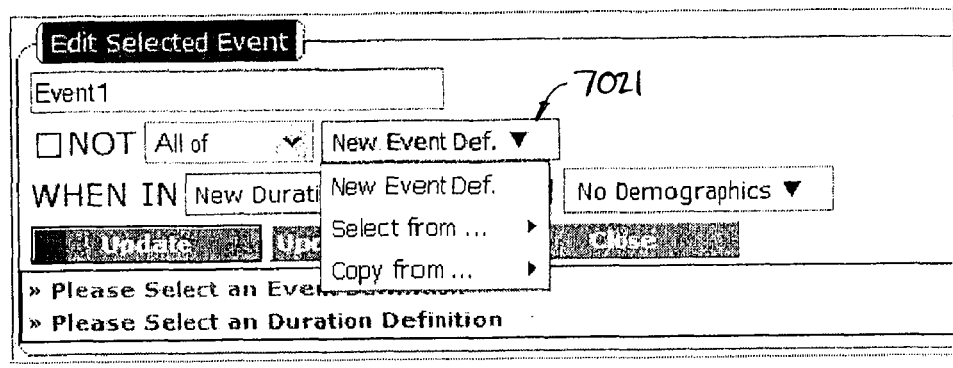
FIG. 71 illustrates a menu on the edit bar of FIG. 70A, providing entry to the Event Definition palette feature of the Event Canvas, in accordance with an embodiment of the disclosure.
Figure 72A:
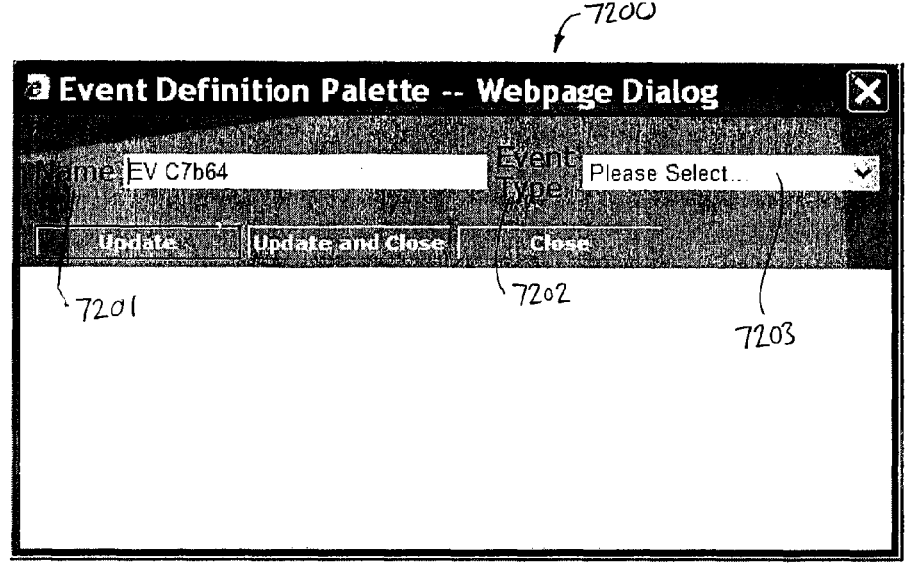
FIGS. 72A-72F illustrate use of the Event Definition palette to define events to be included in a cohort or event collection, in accordance with an embodiment of the disclosure.
Figure 72B:
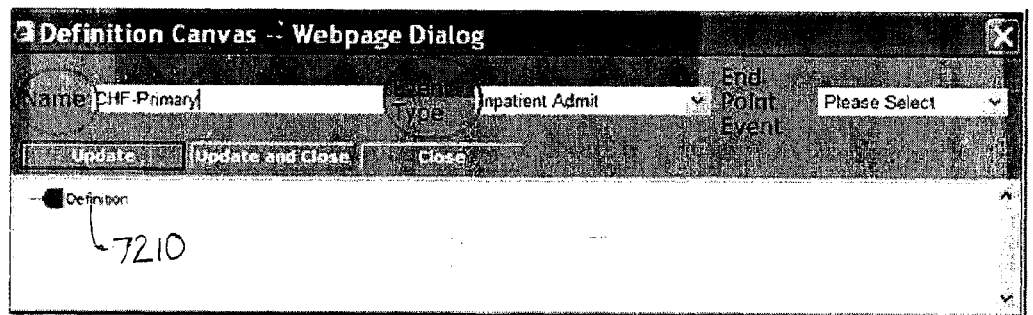

As discussed above, a query regarding a set of medical records is based on those records meeting certain conditions—that is, those patients for whom specified events are applicable. Each event must first be defined. From the edit bar 6704, the user may select "New Event Definition" from window 7021 (see FIG. 71). This selection opens the event definition palette 7200, as illustrated in FIG. 72A. The user enters the name 7201 of the event and selects the type 7202 of the event from a drop-down menu 7203 in the palette. When this basic information is entered, an icon 7210 for the event definition appears (FIG. 72B). At this stage of the event definition, all events of the basic type selected from menu 7203 are included in the definition.

Figure 72C:
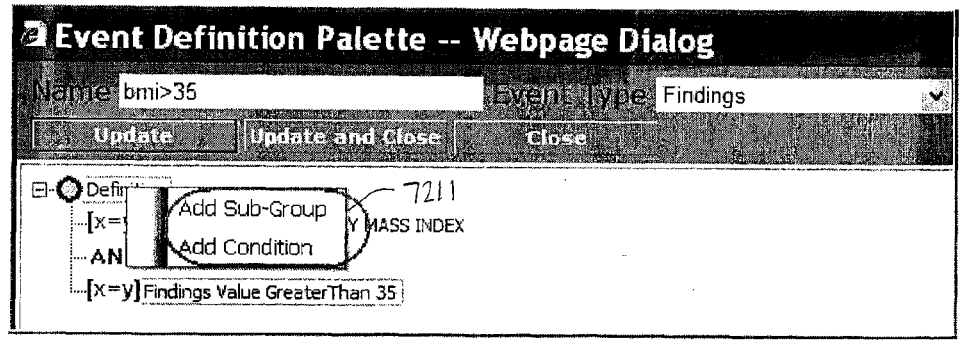
Figure 72:
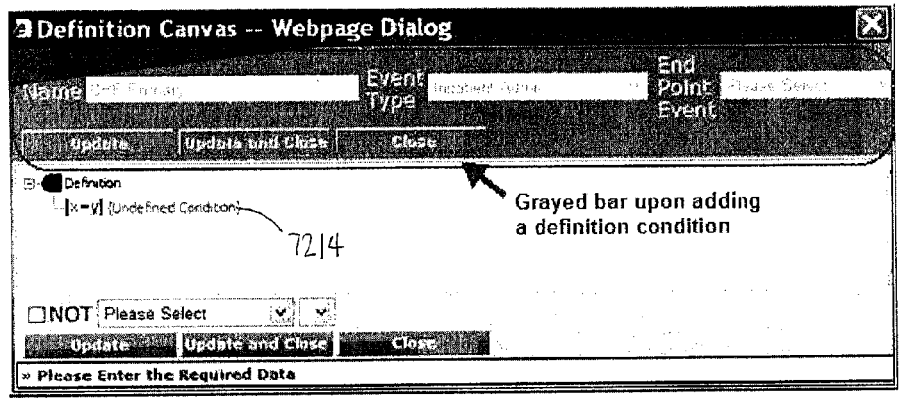
Figure 72E:
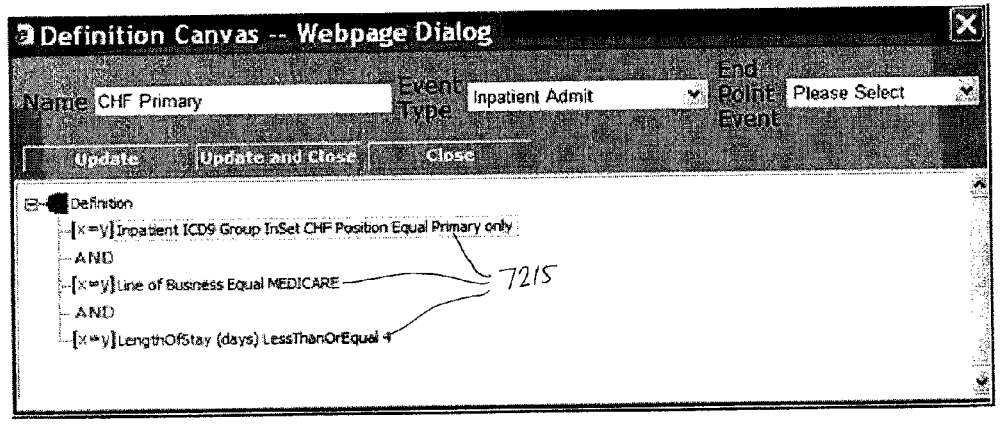

In this embodiment, a user wishing to define an event more precisely selects the definition on the palette (e.g. by clicking on the definition icon 7210), which causes a sub-menu 7211 to appear (see FIG. 72C). The user may then add one or more conditions to the event definition. Selecting "Add Condition" in sub-menu 7211 causes an icon 7214 for the (as-yet undefined) condition to appear, as shown in FIG. 72D. One or more conditions 7215, linked to each other by logical operators, may then be specified by entering on the definition canvas (see FIG. 72E). As shown in FIG. 72E, the event definition may have multiple conditions associated therewith, provided only that those conditions are logically consistent with the basic nature of the event. For example, as shown in FIG. 72E, an inpatient admission record may have associated conditions such as the ICD-9 diagnosis, length of stay, and line of business (e.g. congestive heart failure, less than or equal to 4 days, and Medicare, respectively). Alternatively, a condition on the event may be specified by choosing a particular event attribute 7216 on the edit bar 6704, as shown in FIG. 72F.

Figure 72F:
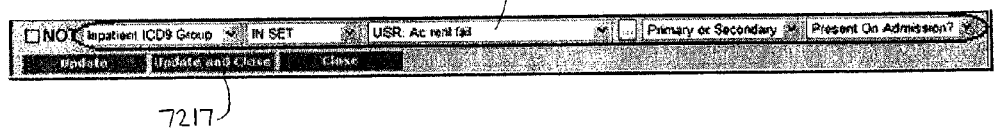

After all conditions on the event have been specified, the user updates and closes the event definition by selecting the "Update and Close" button 7217 on the edit bar (see FIG. 72F).

Figure 73A:
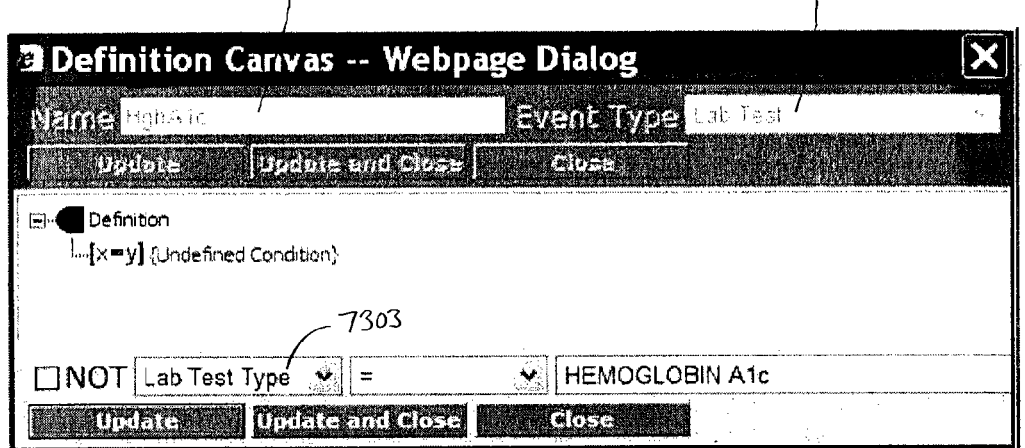
FIGS. 73A-73C show another example of use of the Event Definition palette.
Figure 73B:
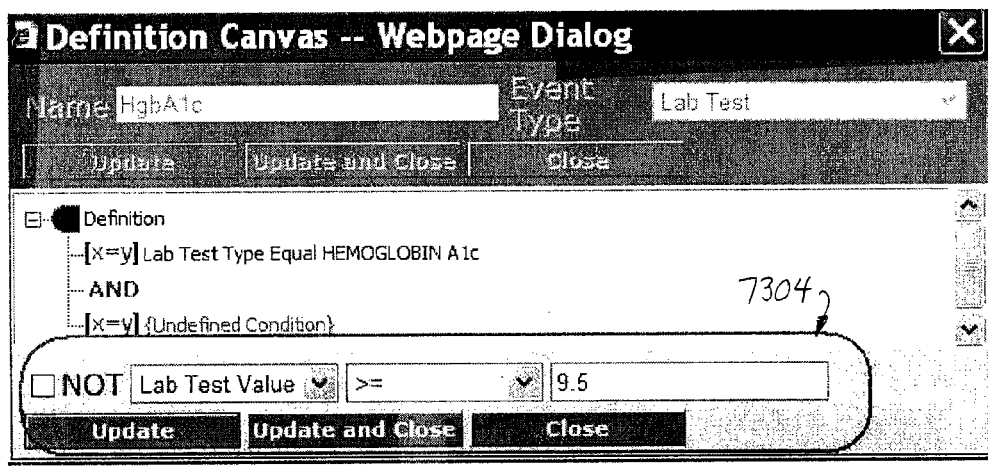
Figure 73C:
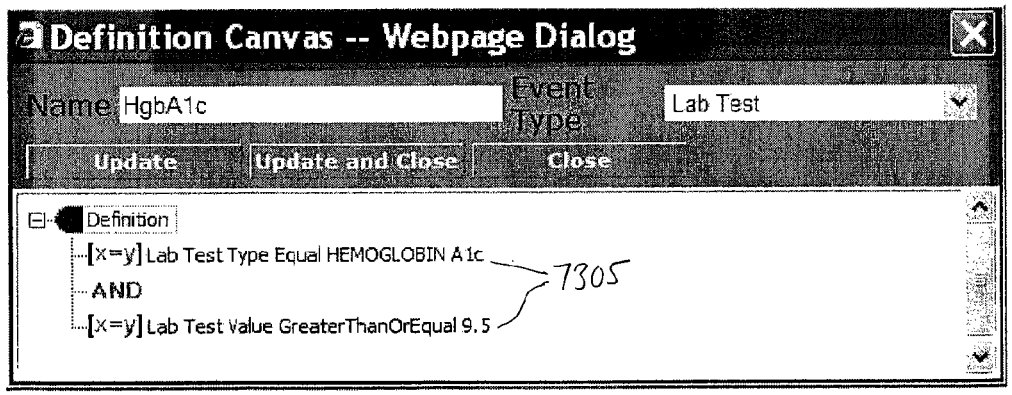

In another example, if the event type is a specific lab test, the event definition may refer to a value corresponding to a result of that test. FIG. 73A shows the definition canvas where a name 7301 "HgbA1c" has been entered for the event, and the event type 7302 is given as "Lab Test." A drop-down menu 7303 on the edit bar is used to specify the type of test. Another selection from menu 7303 permits the user to enter a specific value (or range of values) of test result as a condition 7304 on the event definition (see FIG. 73B). Conditions 7305, linked by the AND operator, thus are added to the event definition (FIG. 73C). It is possible for the user to enter an unreasonable or impossible value when selecting condition 7304, but this would result in an empty cohort or event collection being built.

Figure 74:
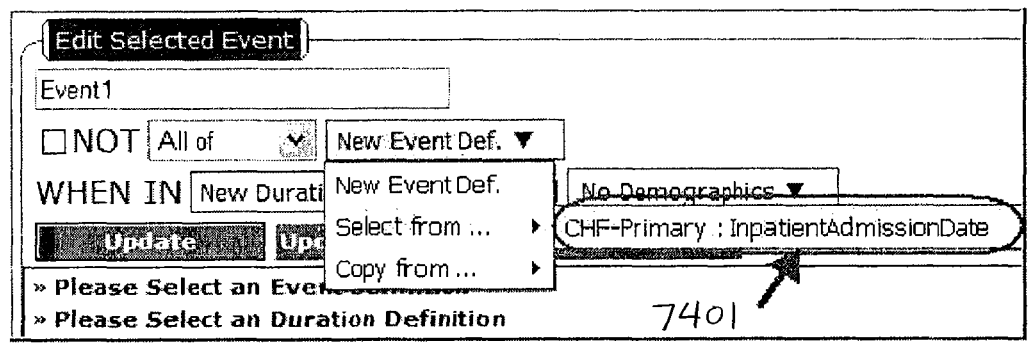
FIG. 74 illustrates the result of an event definition, as displayed on the edit bar of FIG. 71.
Figure 75:
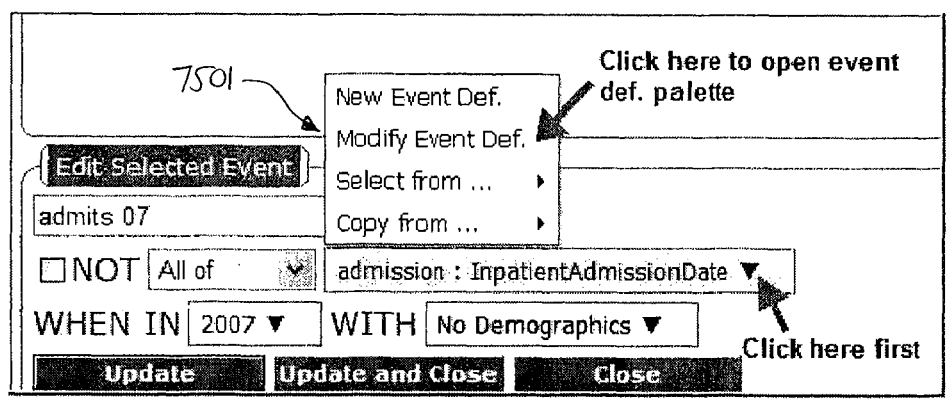
FIG. 75 illustrates another menu on the edit bar, permitting an event definition to be modified in accordance with an embodiment of the disclosure.

After all desired conditions on the event are entered, the user may update and close the event definition. This causes the name 7401 of the event to appear on the edit bar as an event which may be selected for further editing (see FIG. 74; compare with FIG. 71). An event definition, once selected, may then be modified by selecting (e.g. clicking on) the "Modify Event Definition" option in the drop-down menu of the edit bar (see FIG. 75). The user is then returned to the event definition palette.

Duration Definition

Figure 76A:
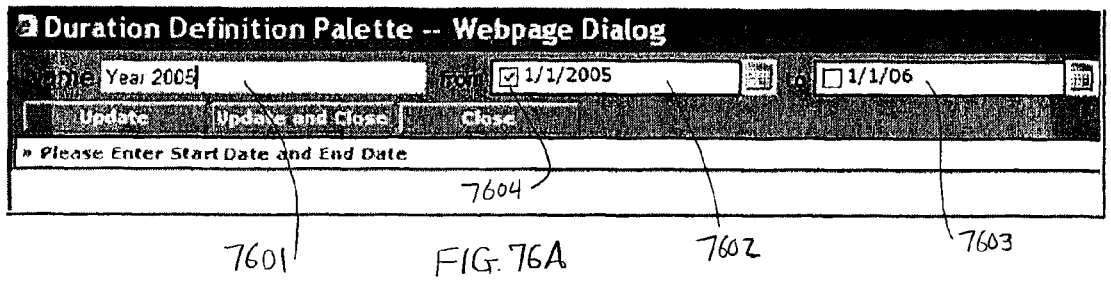
FIGS. 76A-76C illustrate use of the Duration Definition palette to add conditions to events to be included in a cohort or event collection, in accordance with an embodiment of the disclosure.

In an embodiment, selecting "New Duration Definition" 7022 in the edit bar 6704 causes the Duration Definition palette 7600 to be displayed (see FIG. 76A). This palette is used to add time-related criteria to an event. For example, a time interval may be given a name 7601, a start date 7602 and an end date 7603. In this embodiment, a check box 7604 is also provided, so that the user may specify whether the time interval includes or excludes the start/end date. As shown in FIG. 76A, "Year 2005" has start and end dates of Jan. 1, 2005 (inclusive) and Jan. 1, 2006 (exclusive), respectively.

Figure 76B:
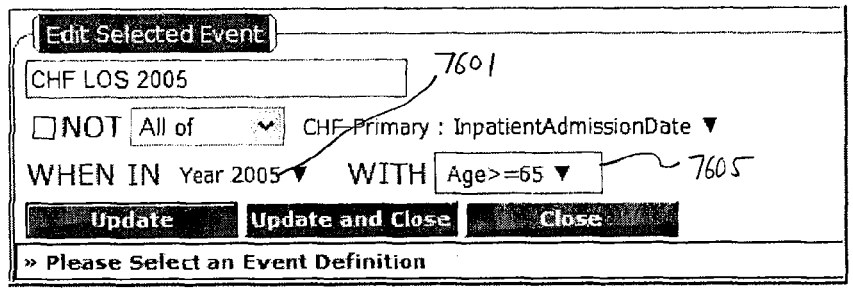
Figure 76C:
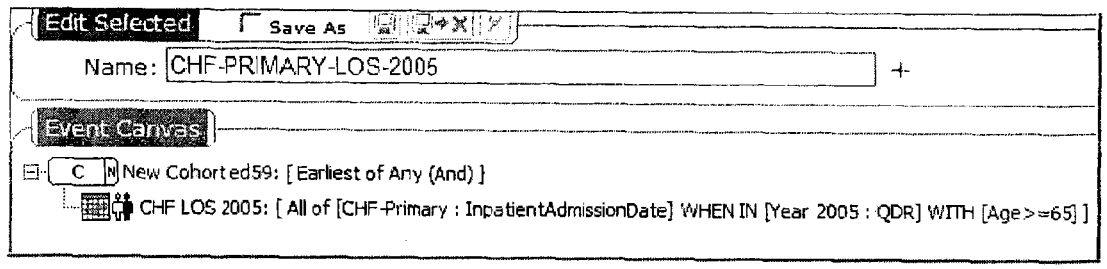

A defined event is thus specified to have occurred "when in" a particular time interval; the interval name 7601 is displayed in the edit bar, as shown in FIG. 76B. Additional criteria, such as a demographic condition 7605 (e.g. "Age greater than or equal to 65") may be entered using the edit bar. After the user updates and closes the event definition on the edit bar, the additional criterion is listed "with" the "when in" condition accompanying the event name on the Event Canvas, as shown in FIG. 76C.

Figure 77A:
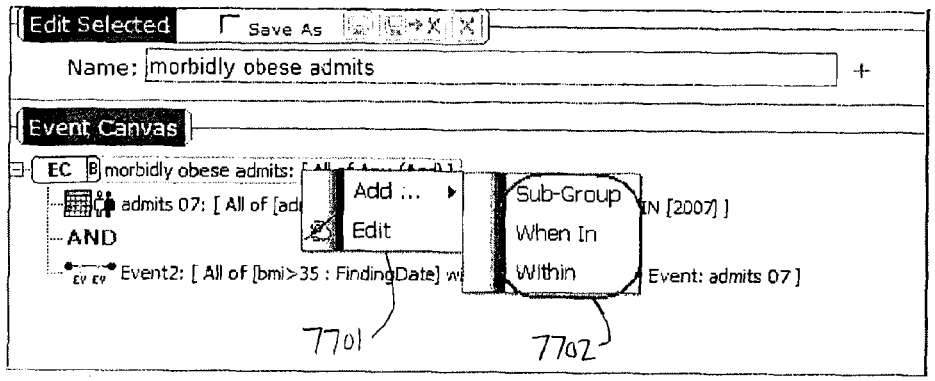
FIGS. 77A and 77B illustrate editing of an event collection definition to include WHEN IN and WITHIN conditions, in accordance with an embodiment of the disclosure.
Figure 77B:
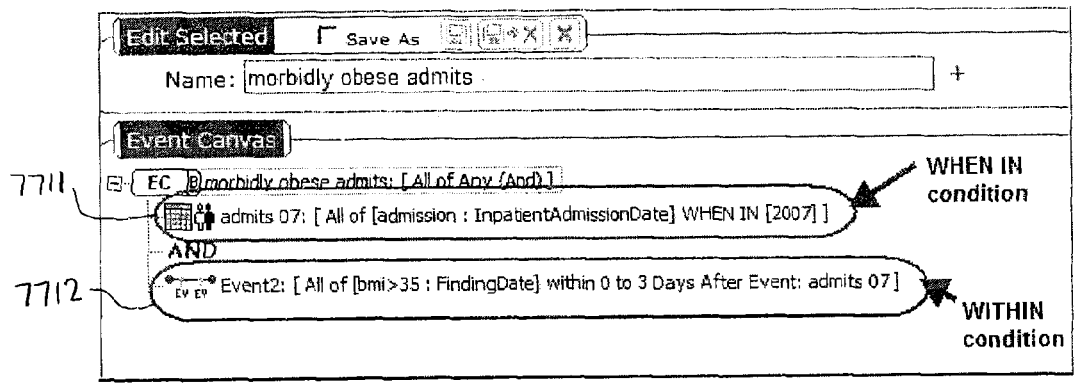

In an embodiment, the user may select an event definition by clicking on the icon associated with that definition on the Event Canvas, causing sub-menus 7701, 7702 to be displayed (see FIG. 77A). The user may then add a WHEN IN or WITHIN time condition, as shown in FIG. 77B. The WHEN IN condition 7711 may conveniently be indicated by a calendar symbol and the WITHIN condition indicated by a timeline symbol, as shown in FIG. 77B. The WHEN IN condition anchors the event to a specified range of dates. The WITHIN condition defines a duration and direction (forward or backward in time) relating one event to another. For example, as shown in FIG. 77B, the WITHIN condition 77B specifies an event target (BMI found to be greater than 35), a duration and direction (0 to 3 days after) and another event (a hospital admission in calendar 2007). A WITHIN condition may also be used to define a "blackout period" between two events. For example, specifying "2 to 3 days after" excludes events 0 days or 1 day after the target event.

Example: Cohort Build

In the following example, a physician wishes to identify the number of patients admitted over the course of a year who have a body-mass index (BMI) greater than 35, and the proportion of such patients relative to the total number admitted. Since a group of patients is to be identified, as opposed to a group of events, the physician (user) seeks to build a new cohort rather than a new event collection.

Figure 68:
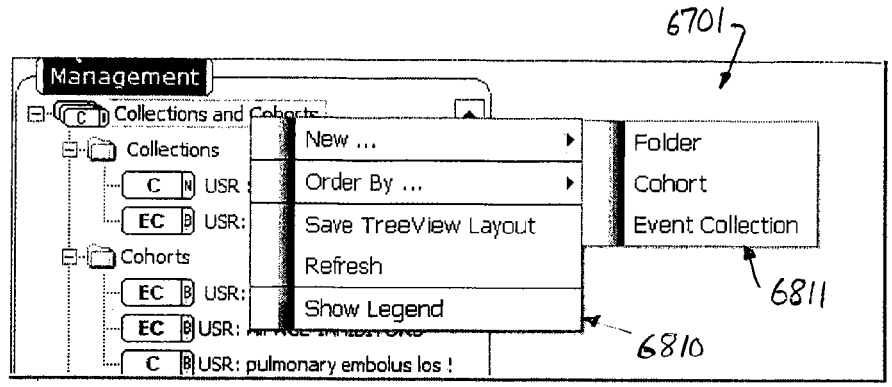
FIG. 68 shows a partial screenshot of the Management windowpane of the user interface of FIG. 67.
Figure 69A:
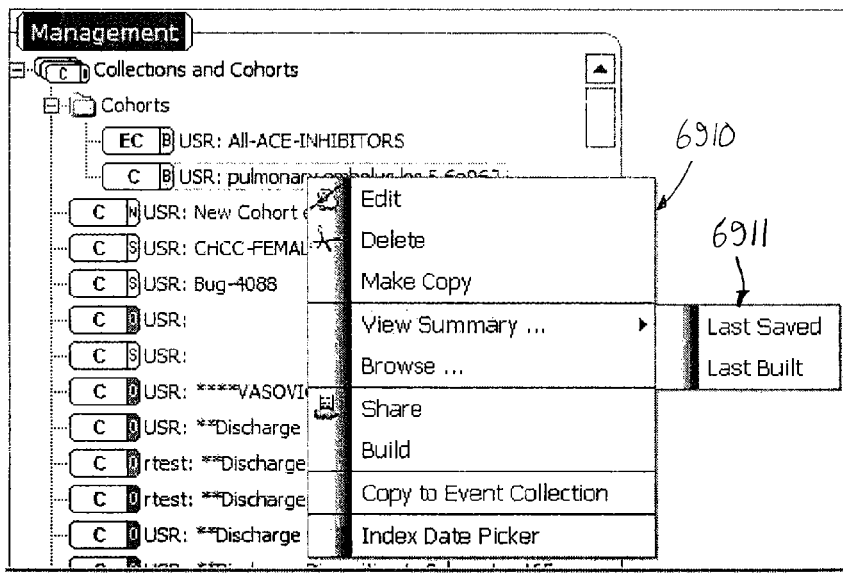
FIGS. 69A-69C illustrate menus and icons which may appear in the Management windowpane of FIG. 68.
Figure 69B:
Figure 69C:
Figure 78A:
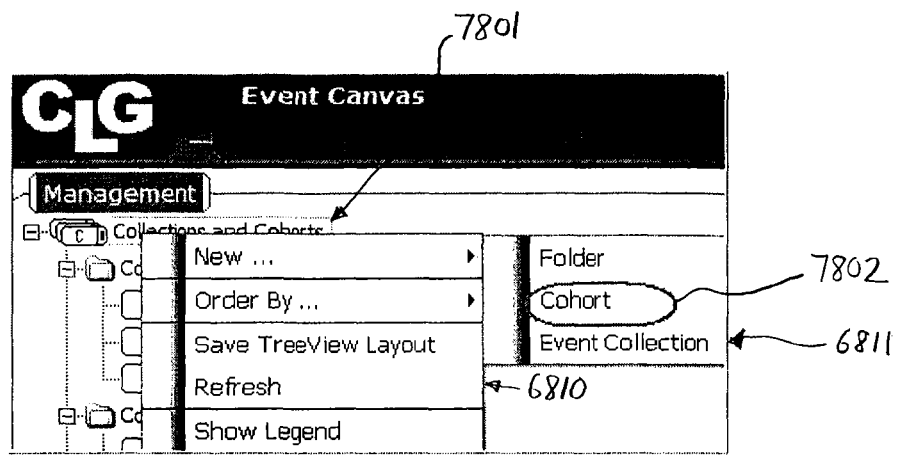
Figure 78B:
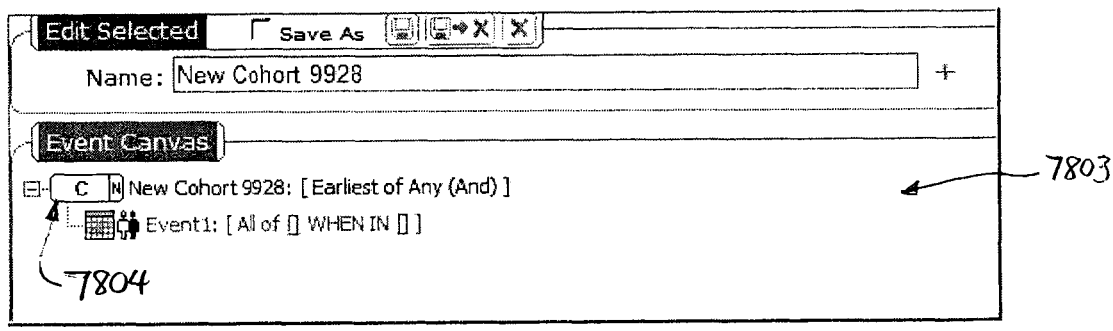

In the Management windowpane 6701, the user selects "Collections and Cohorts" 7801, causing menu 6810 to appear; selecting "New" causes sub-menu 6811 to appear (see FIG. 78A; compare FIG. 68). Selecting "Cohort" 7802 then opens an empty Event Canvas 7803 with a cohort icon 7804 labeled "New Cohort" (FIG. 78B). It is noteworthy that in defining a cohort, only the earliest event pertaining to a particular patient will be added to the cohort, thereby ensuring that a given patient is included only once.

Figures 78C, 78D:
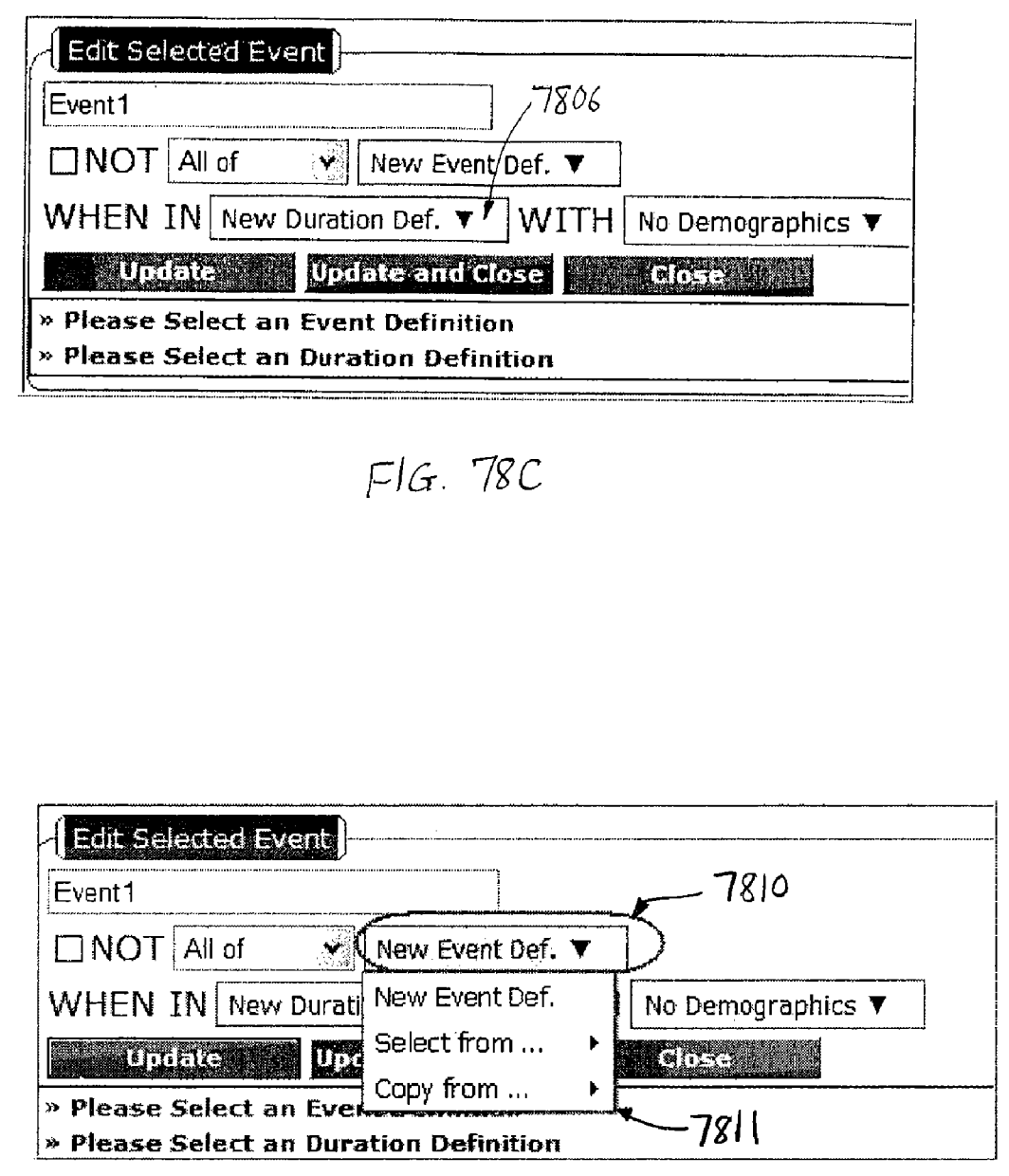
Figure 78E:
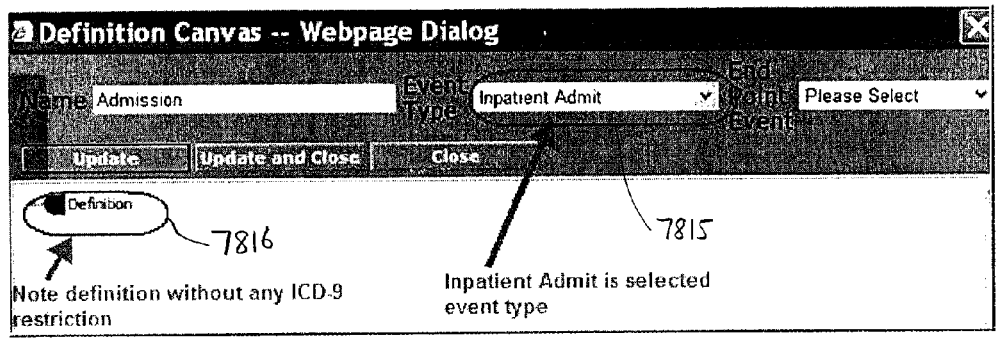

The user then proceeds to define the events for the cohort using the edit bar (FIG. 78C). Selecting "New Event Def." 7810 in the edit bar causes menu 7811 to be displayed (FIG. 78D). Selecting "New Event Def." in this menu opens the event definition palette (FIG. 78E). Choosing "Inpatient Admit" as an event type 7815 causes a "Definition" icon 7816 to be displayed for the event; at this point the event definition includes all inpatient admissions without restrictions.

Figure 78F:
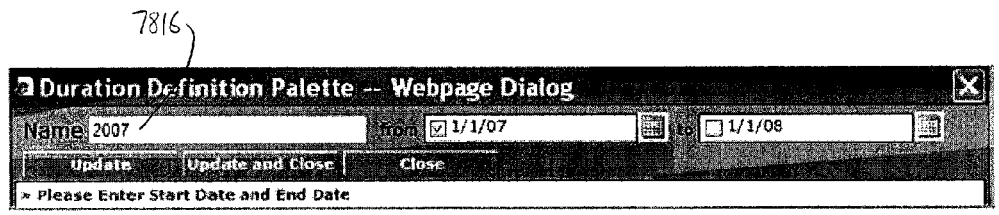
Figure 78G:
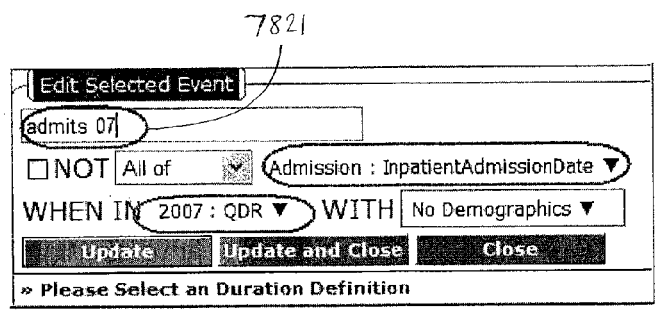

The user then returns to the edit bar and selects "New Duration Def." 7806 to open the duration definition palette (see FIGS. 78C and 78F). Choosing the duration definition name 7816 "2007" results in a duration condition being added to the event definition, namely "Jan. 1, 2007 inclusive to Jan. 1, 2008 exclusive" (see FIG. 78F). The user may then rename the selected event in the edit bar (e.g. the name 7821 "admits 07" as shown in FIG. 78G).

Figure 79D:
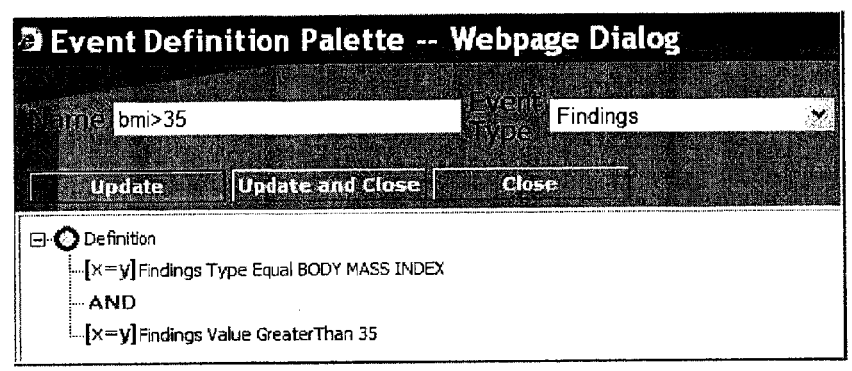
Figure 79E:
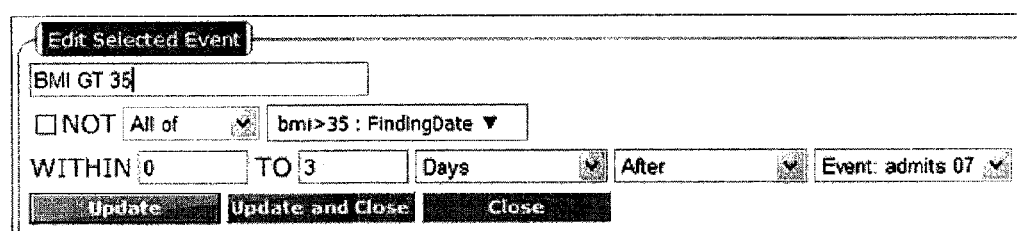
Figure 79F:
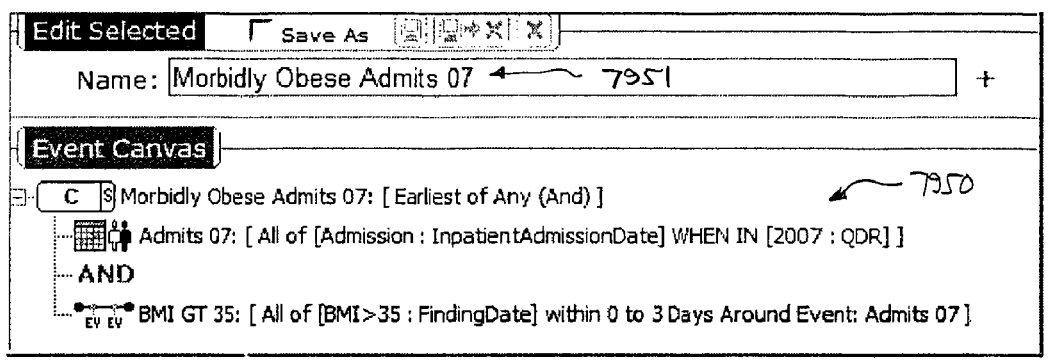

Selecting the cohort icon 7901 on the event canvas permits the user to rename the cohort using the control bar 6703. Here the new name chosen for the cohort is "morbidly obese admits" (FIG. 79A). The selected duration appears as a WHEN IN condition 7902 under the cohort icon on the event canvas. To add the condition "BMI>35", the user returns to the event definition palette and chooses "Findings" as an event type. This causes "Findings Type" to be displayed, with "BODY MASS INDEX" a selectable item in the drop-down menu for findings (FIG. 79B). To set a condition BMI>35, the user enters ">" and "35" in the appropriate fields (FIG. 79C). Selecting "Update and Close" results in the added condition appearing in the event definition (FIG. 79D). Finally, the user may select and edit the event to add a WITHIN condition, such as "finding of BMI>35 within 3 days of admission" (see FIG. 79E). Selecting "Update and Close" returns the user to the Event Canvas, where the completed definition 7950 of the cohort is displayed (FIG. 79F). A new and more descriptive cohort name 7951 is entered and updates on the event canvas.

Figure 80:
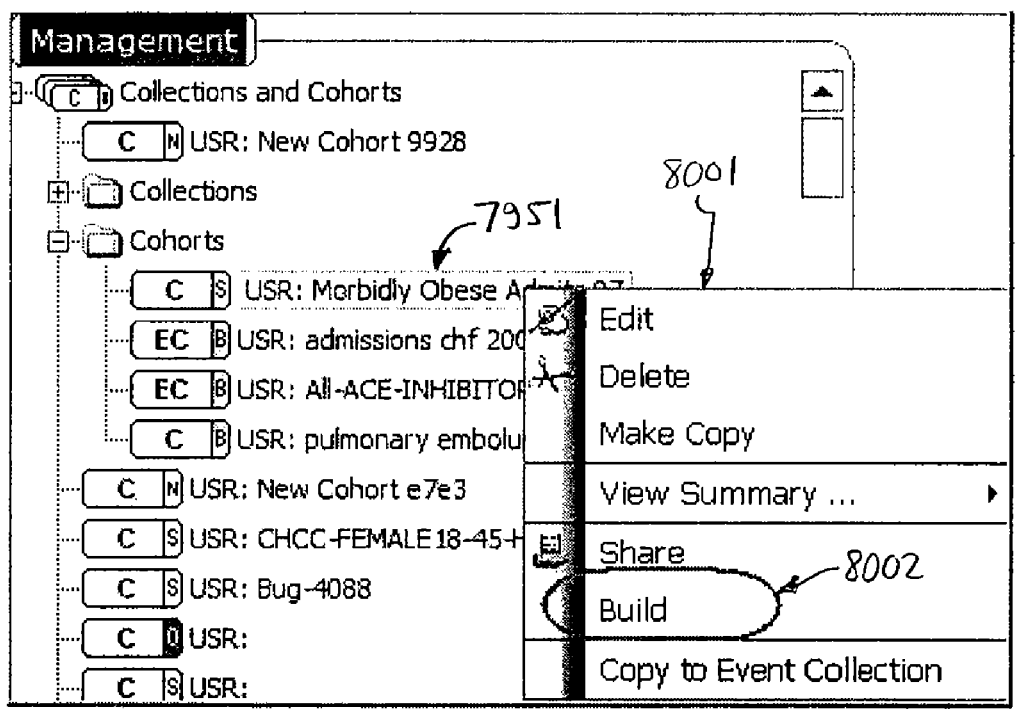
FIG. 80 shows a screenshot with the cohort of FIGS. 79A-79F listed in the Management windowpane, and a menu for use in building the cohort, in accordance with an embodiment of the disclosure.

At this point the user has defined a cohort named "Morbidly Obese Admits 07." This cohort is now ready to be built; that is, the system may be caused to search patient records for patients meeting the criteria for the cohort. The user returns to the Management pane and selects the cohort by name, thereby causing menu 8001 to be displayed (FIG. 80). The user then selects the "Build" option 8002.

Figure 81A:
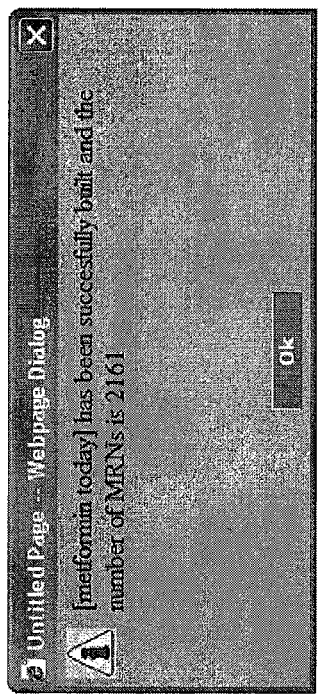
FIGS. 81A-81C illustrate results of the cohort build process using the Event Canvas, in accordance with an embodiment of the disclosure.

The system proceeds to search all patient records meeting the criteria, and returns a message 8100 informing the user of the number of medical record numbers (MRNs) in the cohort. In this example, there are 1,386 patients (FIG. 81A).

Figure 81B:
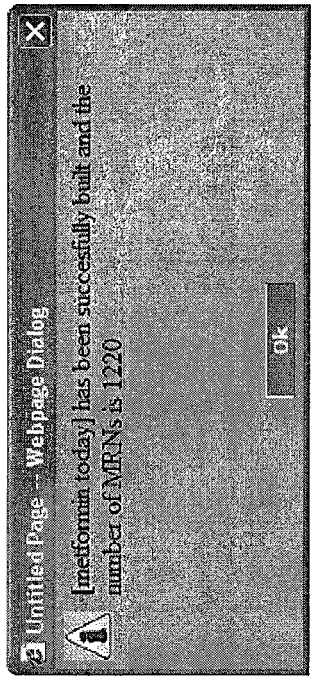
Figure 81C:
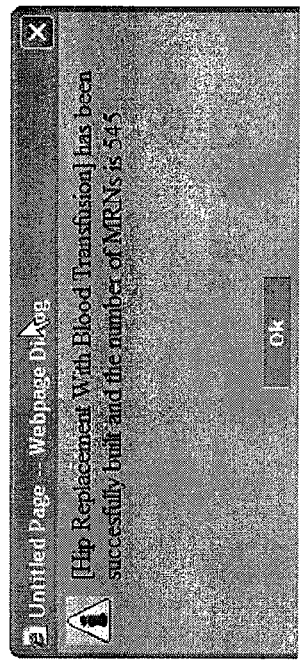

To compare this cohort with all admitted patients whose BMI was measured, the user may easily modify the cohort definition, e.g. replace "BMI>35" with "BMI>10" and build the cohort anew. (A BMI for an individual, if measured at all, must reasonably exceed 10). The result of this example—8, 273 patients—is shown in FIG. 81B. Finally, in order to compare these results with the total number of admitted patients during the same time period, the user may modify the cohort definition by removing BMI as a condition, and again build the cohort. The result of this example—8,364 patients—is shown in FIG. 81C. The user can then conclude that 8273/48364 or 17.1% of the admitted patient population had their BMI measured, and of those patients, 1386/8273 or 16.8% were morbidly obese.

Event Canvas: Additional Embodiments

It will be appreciated that the Event Canvas, an embodiment of which is described above, permits a user to construct complex clinical queries. In particular, a user may define groups of qualifying events, linked using logical operators, at any level of complexity. It is noteworthy that a group, once defined, may be used in multiple inquiries. In an embodiment, the Event Canvas is implemented using AJAX technology, so that data may be fetched efficiently from the various databases.

Cohorts and event collections built with the Event Canvas may be used in a variety of analytics, including but not limited to those detailed herein. In particular, a cohort built with the Event Canvas may be effectively used in the Time to Event analytic and the Quality Duration Calculator described above.

Query Engine

Figure 82:
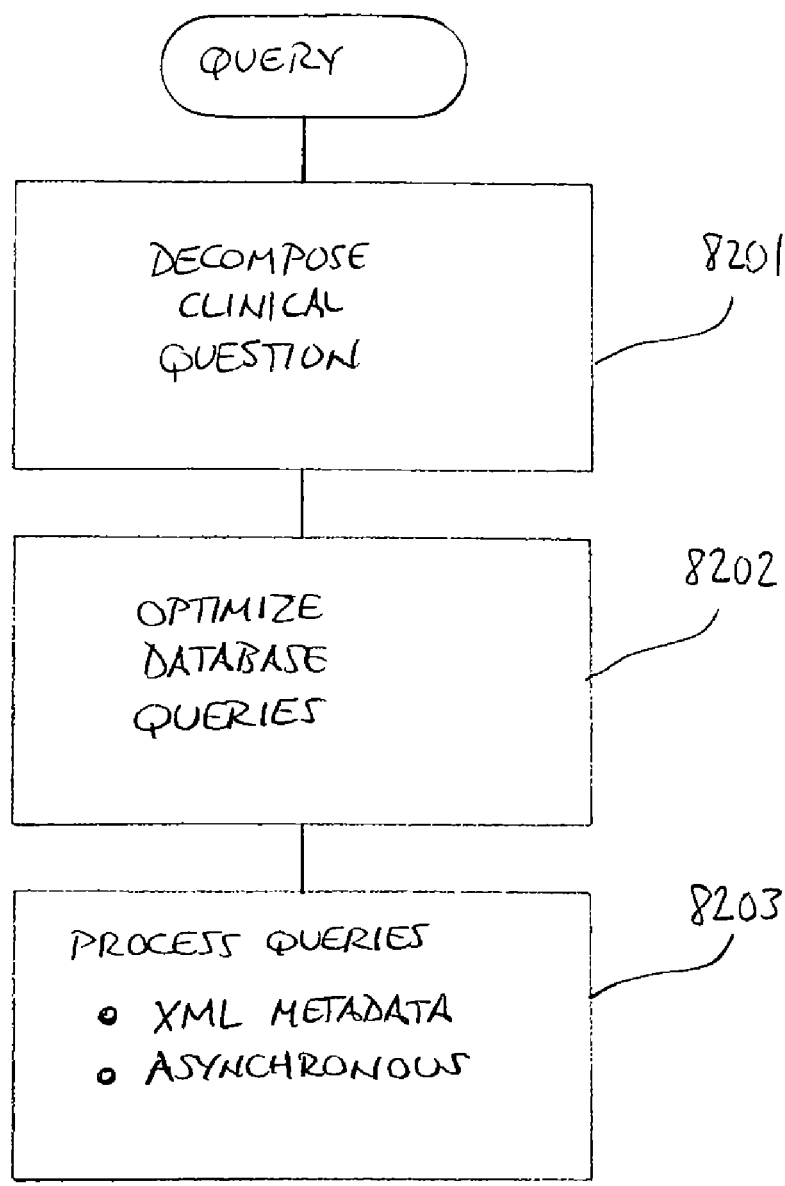
FIG. 82 shows a flowchart schematically illustrating a process for processing database queries to answer a clinical question, in accordance with an embodiment of the disclosure.

FIG. 82 schematically illustrates steps in a process for executing database queries to obtain answers to the user's clinical questions, in accordance with an embodiment of the disclosure. A query engine, which may be resident on server 36, decomposes the user's clinical question (step 8201) into multi-threaded database queries. These database queries are optimized for performance (step 8202). This permits retrieval of data from multiple data sources such as database 32 or other sources available on the network 30. The queries are processed (step 8203) preferably using XML metadata and asynchronously in small batches.

HIPAA Challenge

In a further embodiment of the disclosure, the server 36 is configured so that administrators may maintain profiles of users. In particular, a user profile may include information regarding whether the user has permission (e.g. from an institutional review board) to view patient identifiers. When a user seeks to run a report showing patient identifiers, the HIPAA Challenge software (preferably resident on server 36) causes a dialog box to be displayed on the user's display 18. The user is then required to explain his request for access to the identifiers. No patient identifiers are provided in the reports without a challenge and an explanation being logged by the user. Instances of HIPAA challenges may themselves be logged, so that such report requests may easily be tracked and audited.

Help and Collaboration Tools

In an additional embodiment, the server 36 is configured to provide online user manuals and streaming video to instruct and guide users. The server may also be configured to support a forum of users communicating over network 30. In particular, each user may be invited to start a blog relating to his experiences using the system.

Systems and modules described herein may comprise software, firmware, hardware, or any combination(s) of software, firmware, or hardware suitable for the purposes described herein. Software and other modules may reside on servers, workstations, personal computers, computerized tablets, PDAs, and other electronic devices suitable for the purposes described herein.

Software and other modules may be accessible via local memory, via a network, via a browser or other application in an ASP context, or via other means suitable for the purposes described herein. Data structures described herein may comprise computer files, variables, programming arrays, programming structures, or any electronic information storage schemes or methods, or any combinations thereof, suitable for the purposes described herein. User interface elements described herein may comprise elements from graphical user interfaces, command line interfaces, and other interfaces suitable for the purposes described herein. Screenshots presented and described herein can be displayed differently as known in the art to input, access, change, manipulate, modify, alter, and work with information.

While the invention has been described and illustrated in connection with preferred embodiments, many variations and modifications as will be evident to those skilled in this art may be made without departing from the spirit and scope of the invention, and the invention is thus not to be limited to the precise details of methodology or construction set forth above as such variations and modification are intended to be included within the scope of the invention.

We claim:

1. A method, executed on a computing device, for facilitating management of patient care, the method comprising:
   building a cohort or event collection of interest by performing a series of steps, including
      receiving in the computing device data defining one or more events relating to the cohort or event collection, where each of the events is applicable to a plurality of patient records;
      receiving in the computing device data specifying logical relationships between the one or more events;
      composing a logical expression including the one or more events in accordance with the relationships, where the logical expression relates to a clinical question of a user;
      receiving in the computing device data specifying a limiting condition on the logical expression, said specified limiting condition including
         at least one calendar time period relating to at least one of the one or more events, and
         one of inclusion and exclusion of at least one of the one or more events within a time interval, said at least one event having a specified temporal relationship to a start time or to another event;
   accessing a computer-readable memory storing a database of patient records;
   identifying patient records in the database consistent with the logical expression;
   including in a set of patient records, for each patient having at least one of said identified patient records consistent with the logical expression, either
      only one of said identified patient records for each patient, said set of patient records then being characterized as a cohort, or
      all of said identified patient records for each patient, said set of patient records then being characterized as an event collection, and
   labeling said set of patient records as a cohort or an event collection;
   performing a query on said set of patient records for the cohort or event collection to yield a query result, the query including the clinical question; and
   generating a report including the query result,
   wherein
      said defining is performed via a first portion of a user interface executing on said computing device affording a user access to data for defining the events,
      the limiting condition is specified via a second portion of the user interface, and
      the label of the cohort or event collection is displayed on a third portion of the user interface, affording the user access to a definition of the cohort or event collection.

2. The method according to claim 1, wherein the logical expression includes a demographic criterion relating to the plurality of patient records, the demographic criterion being a limiting condition on the logical expression.

3. The method according to claim 1, wherein an event is characterized as a diagnosis, a hospital admission or a laboratory test.

4. The method according to claim 1, wherein the event is defined as occurring during the at least one specified calendar time period, the limiting condition being characterized as a WHEN IN condition.

5. The method according to claim 1, wherein the at least one specified calendar time period is a time period between a first event and a second event, the limiting condition being characterized as a WITHIN condition.

6. The method according to claim 1, further comprising performing statistical calculations relating to the query result; and
including results of said calculations in the report.

7. The method according to claim 1, further comprising:
displaying to the user a challenge to provide an explanation for the query, to ensure compliance with the Health Insurance Portability and Accountability Act (HIPAA).

8. A user interface, displayed on a display device, for organizing a query related to patient care, the query including a clinical question, the user interface comprising:
a first portion configured to display user definitions of
one or more events relating to a cohort or event collection of interest and applicable to a plurality of patient records, and
a logical expression including the one or more events and relating to the clinical question;
a second portion configured to display a user-specified limiting condition on the logical expression, said specified limiting condition including
at least one calendar time period relating to at least one of the one or more events, and
one of inclusion and exclusion of at least one of the one or more events within a time interval, said at least one event having a specified temporal relationship to a start time or to another event; and
a third portion configured to display a user-specified label of at least one set of patient records, the label indicating that the set is either a cohort or an event collection,
wherein the at least one set of patient records is identified based on at least the logical expression and the limiting condition on the logical expression; and
wherein
an event collection includes all patient records consistent with the logical expression, and
a cohort includes, for a given patient, only one patient record consistent with the logical expression.

9. The user interface according to claim 8, wherein the second portion is configured to display a user-specified demographic criterion relating to the plurality of patient records, the demographic criterion being a limiting condition on the logical expression.

10. The user interface according to claim 8, wherein an event is characterized as a diagnosis, a hospital admission or a laboratory test.

11. The user interface according to claim 8, wherein the event is defined as occurring during the at least one user-specified calendar time period, the limiting condition being characterized as a WHEN IN condition.

12. The user interface according to claim 8, wherein the at least one user-specified calendar time period is a time period between a first event and a second event, the limiting condition being characterized as a WITHIN condition.

13. The user interface according to claim 8, wherein a user orders a new cohort or a new event collection via the third portion of the user interface.

14. A system for evaluating patient care, comprising:
a user input device and display;
a database of patient data; and
a server configured to
provide a user interface accessible by the user at the user input device, the user interface having
a first portion configured to display user definitions of
one or more events relating to a cohort or event collection of interest and applicable to a plurality of patient records, and a logical expression including the one or more events and relating to a clinical question of the user;
a second portion configured to display a user-specified limiting condition on the logical expression, said specified limiting condition including
at least one calendar time period relating to at least one of the one or more events, and
one of inclusion and exclusion of at least one of the one or more events within a time interval, said at least one event having a specified temporal relationship to a start time or to another event; and
a third portion configured to display a user-specified label of at least one set of patient records, the label indicating that the set is either a cohort or an event collection, wherein an event collection includes all patient records consistent with the logical expression, and a cohort includes, for a given patient, only one patient record consistent with the logical expression,
wherein the at least one set of patient records is identified based on at least the logical expression and the limiting condition on the logical expression;
provide access to the database of patient data,
perform a query on the patient data for the cohort or event collection to yield a query result, the query including the clinical question, and
generate a report including the result of the query, in accordance with a request from the user.

15. The system according to claim 14, wherein the logical expression includes a demographic criterion relating to the plurality of patient records, the demographic criterion being a limiting condition on the logical expression.

16. The system according to claim 14, wherein an event is characterized as a diagnosis, a hospital admission or a laboratory test.

17. The system according to claim 14, wherein the event is defined as occurring during the at least one user-specified calendar time period, the limiting condition being characterized as a WHEN IN condition.

18. The system according to claim 14, wherein the at least one user-specified calendar time period is a time period between a first event and a second event, the limiting condition being characterized as a WITHIN condition.

19. The system according to claim 14, wherein the server is configured to
perform statistical calculations relating to the query result; and
include results of said calculations in the report.

20. The system according to claim 14, wherein the server is configured to display to the user a challenge to provide an explanation for the query, to ensure compliance with the Health Insurance Portability and Accountability Act (HIPAA).

* * * * *

UNITED STATES PATENT AND TRADEMARK OFFICE
CERTIFICATE OF CORRECTION

| | | |
|---|---|---|
| PATENT NO. | : 7,917,376 B2 | Page 1 of 1 |
| APPLICATION NO. | : 12/209434 | |
| DATED | : March 29, 2011 | |
| INVENTOR(S) | : Eran Bellin et al. | |

It is certified that error appears in the above-identified patent and that said Letters Patent is hereby corrected as shown below:

On the title page, at (63) Related U.S. Application Data, "Pat. No. 7,737,477" should read -- Pat. No. 7,734,477 --.

Column 1, line 9, "No. 7,737,477" should read -- No. 7,734,477 --.

Signed and Sealed this
Tenth Day of May, 2011

David J. Kappos
*Director of the United States Patent and Trademark Office*